United States Patent [19]
Black et al.

[11] Patent Number: 6,057,319
[45] Date of Patent: May 2, 2000

[54] 3,4-DIARYL-2-HYDROXY-2,5-DIHYDROFURANS AS PRODRUGS TO COX-2 INHIBITORS

[75] Inventors: Cameron Black, Pointe Claire; Serge Leger, Dollard Des Ormeaux; Petpiboon Prasit, Kirkland; Zhaoyin Wang, Pierrefonds; Pierre Hamel, Laval; Yongxin Han, Kirkland; Gregory Hughes, Bridgewater, all of Canada

[73] Assignee: Merck Frosst Canada & Co., Kirkland, Canada

[21] Appl. No.: 09/068,139

[22] PCT Filed: Oct. 29, 1996

[86] PCT No.: PCT/CA96/00717

§ 371 Date: Oct. 2, 1998

§ 102(e) Date: Oct. 2, 1998

[87] PCT Pub. No.: WO97/16435

PCT Pub. Date: May 9, 1997

Related U.S. Application Data

[60] Provisional application No. 60/008,074, Oct. 30, 1995.

[51] Int. Cl.[7] .................. A61K 31/53; A61K 31/415; C07D 213/06; C07D 253/08; C07D 261/04

[52] U.S. Cl. .................. 514/242; 514/249; 514/277; 514/363; 514/364; 514/381; 514/398; 549/65; 549/474; 546/251; 544/183; 544/239; 558/409; 548/127; 548/132; 548/182; 548/229; 548/243; 548/251

[58] Field of Search .................. 514/462, 471, 514/472, 473, 242, 249, 277, 363, 364, 381, 398, 407; 549/331, 476, 479, 480, 65, 474; 564/91; 568/28, 30, 31, 32, 33; 558/409; 546/251; 544/183, 239

[56] References Cited

U.S. PATENT DOCUMENTS 5,698,584 12/1997 Black et al. .................. 514/462

*Primary Examiner*—Johann Richter
*Assistant Examiner*—Ebenezer Sackey
*Attorney, Agent, or Firm*—Richard C. Billups; David L. Rose

[57] ABSTRACT

The invention encompasses the novel compound of formula (I) useful in the treatment of cyclooxygenase-2 mediated diseases. The invention also encompasses certain pharmaceutical compositions for treatment of cyclooxygenase-2 mediated diseases comprising compounds of formula (I).

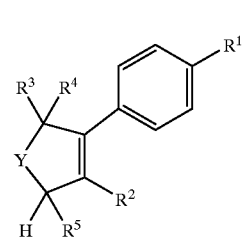

(I)

20 Claims, No Drawings

3,4-DIARYL-2-HYDROXY-2,5-DIHYDROFURANS AS PRODRUGS TO COX-2 INHIBITORS

This application claims benefit from provisional application Ser. No. 60/008,074 filed Oct. 30, 1995.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is manly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effort on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of cyclooxygenase-2 inhibitors is given in an article by John Vane, *Nature*, Vol. 367, pp. 215–216, 1994, and in an article in *Drug News and Perspectives,* Vol. 7, pp. 501–512, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I. These compounds are prodrugs of compounds which inhibit COX-2 selectively over COX-1. The prodrugs are converted in vivo to the selective inhibitors.

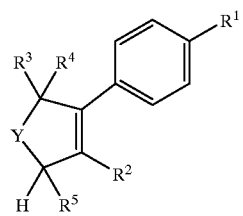

The invention also encompasses certain pharmaceutical compositions for treatment of cyclooxygenase-2 mediated diseases comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I

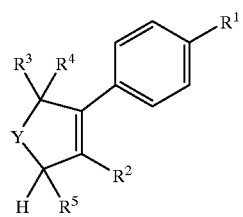

or a pharmaceutically acceptable salt thereof wherein:

Y is selected from the group consisting of
- (a) $C(R^6)(R^7)$,
- (b) O,
- (c) S, and
- (d) C=O;

$R^1$ is selected from the group consisting of
- (a) $S(O)_2CH_3$,
- (b) $S(O)_2NHR^8$,
- (c) $S(O)_2NHC(O)CF_3$,
- (d) $S(O)(NH)NH_2$,
- (e) $S(O)(NH)NHC(O)CF_3$,
- (f) $P(O)(CH_3)NH_2$,
- (g) $P(O)(CH_3)_2$, and
- (h) $C(S)NH_2$;

$R^2$ is selected from the group consisting of
- (a) $NR^{10}R^{11}$,
- (b) $SR^{11}$,
- (c) $OR^{11}$,
- (d) $R^{11}$,
- (e) C1–10alkenyl,
- (f) C1–10alkynyl,
- (g) unsubstituted, mono-, di-, tri- or tetra-substituted $C_3$–$C_{10}$cycloalkenyl wherein the substituents are independently selected from the group consisting of
  - (1) halo, (2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl—$CO_2$—$R^{12}$;
(13) benzyloxy,
(14) —O—$(C_{1-10}$alkyl)—$CO_2R^{12}$, and
(15) —O—$(C_{1-10}$alkyl)—$NR^{12}R^{13}$;

(h) a mono-, di-, tri- or tetra-substituted heterocycloalkyl group of 5, 6 or 7 members or a benzoheterocycle wherein said heterocycloalkyl or benzoheterocycle contains 1 or 2 heteroatoms selected from O, S, or N and optionally contains a carbonyl group or a sulfonyl group, and wherein said substituents are independently selected from the group consisting of
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-10}$alkyl;

(i) styryl or mono or di-substituted styryl wherein the substituent are independently selected from the group consisting of
(1) halo,
(2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl—$CO_2$—$R^{12}$;
(13) benzyloxy,
(14) —O—$(C_{1-10}$alkyl)—$CO_2R^{12}$, and
(15) —O—$(C_{1-10}$alkyl)—$NR^{12}R^{13}$;

(j) phenylacetylene or mono- or di-substituted phenylacetylene wherein the substituents are independently selected from the group consisting of
(1) halo,
(2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl—$CO_2$—$R^{12}$,
(13) benzyloxy,
(14) —O—$(C_{1-10}$alkyl)—$CO_2R^{12}$,
(15) —O—$(C_{1-10}$alkyl)—$NR^{12}R^{13}$, (k) $C_{1-10}$fluoroalkenyl, and
(l) mono- or di-substituted bicyclic heteroaryl of 8, 9 or 10 members, containing 2, 3, 4 or 5 heteroatoms, wherein at least one heteroatom resides on each ring of said bicyclic heteroaryl, said heteroatoms independently selected from O, S and N and said substituents are independently selected from the group consisting of
(1) hydrogen,
(2) halo,
(3) $C_{1-10}$alkyl,
(4) $C_{1-10}$alkoxy,
(5) $C_{1-6}$alkylthio,
(6) CN,
(7) $C_{1-6}$fluoroalkyl, including $CF_3$,
(8) $N_3$,
(9) —$C(R^5)(R^6)$—OH,
(10) —$C(R^5)(R^6)$—O—$C_{1-10}$alkyl;

$R^3$ is hydrogen, $C_{1-10}$alkyl, $CH_2OR^8$, CN, $CH_2CN$, or $C_{1-6}$fluoroalkyl, F, $CONR^8_2$, unsubstituted or mono- or di-substituted phenyl, unsubstituted or mono or di-substituted benzyl, unsubstituted or mono- or di-substituted heteroaryl, unsubstituted or mono or di-substituted heteroaryl methyl, wherein the substituents are independently selected from the group consisting of
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-10}$alkyl;

$R^3$ is hydrogen, $C_{1-10}$alkyl, $CH_2OR^3$, CN, $CH_2CN$, or $C_{1-6}$fluoroalkyl, F, $CONR^8_2$, unsubstituted or mono- or di-substituted phenyl, unsubstituted or mono or di-substituted benzyl, unsubstituted or mono- or di-substituted heteroaryl, unsubstituted or mono or di-substituted heteroarylmethyl, wherein the substituents are independently selected from the group consisting of
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-10}$alkyl;

$R^4$ is
(a) hydrogen,
(b) $C_{1-10}$alkyl,
(c) $C_{1-10}$alkoxy,
(d) $C_{1-10}$alkylthio,
(e) —OH,
(f) —$OCOR^8$,
(g) —SH,
(h) —$SCOR^8$,
(i) —$OCO_2R^9$,
(j) —$SCO_2R^9$,
(k) $OCONR^8_2$,
(l) $SCONR^8_2$,
(m) $C_{3-10}$cycloalkoxy, and
(n) $C_{3-10}$cycloalkylthio, or $R^3$ and $R^4$ together with the carbon to which they are attached form a monocyclic ring of 3, 4, 5, 6, or 7 members which ring optionally contains one or two heteroatoms selected from O, S or N;

$R^5$ is selected from the group consisting of
  (a) $OR^{17}$,
  (b) $SR^{18}$,
  (c) $NR^{17}R^{18}$,
  (d) $NHS(O)_2R^{18}$,
  (e) $S(O)R^{18}$,
  (f) $S(O)_2R^{18}$,
  (g) $S(O)_2NR^{17}_2$,
  (h) $OP(O)(OR^{16})_2$;

$R^6$ and $R^7$ are independently
  (a) hydrogen,
  (b) unsubstituted or mono- or di-substituted phenyl or unsubstituted or mono- or di-substituted benzyl or unsubstituted or mono- or di-substituted heteroaryl or mono- or di-substituted heteroarylmethyl, wherein said substituents are independently selected from the group consisting of:
    (1) halo,
    (2) $C_{1-10}$alkyl,
    (3) $C_{1-10}$alkoxy,
    (4) $C_{1-10}$alkylthio,
    (5) CN,
    (6) $CF_3$,
    (7) $N_3$,
    (8) —$C(R^{14})(R^{15})$—OH, and
    (9) —$C(R^{14})(R^{15})$—O—$C_{1-10}$alkyl, and
  (c) $C_{1-10}$alkyl, $CH_2OR^8$, CN, $CH_2CN$, $C_{1-10}$fluoroalkyl, $CONR^8_2$, F or $OR^8$,
or $R^6$ and $R^6$ together with the carbon to which they are attached form a saturated monocyclic carbon ring of 3, 4, 5, 6 or 7 atoms;

each $R^8$ is independently selected from the group consisting of
  (a) hydrogen and
  (b) $R^9$;

each $R^9$ is independently selected from the group consisting of
  (a) $C_{1-10}$alkyl,
  (b) —$C_{1-10}$alkyl—$CO_2H$,
  (c) $C_{1-10}$alkyl—$NH_2$,
  (d) phenyl or mono-, di- or tri-substituted phenyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
  (e) benzyl or mono-, di- or tri-substituted benzyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
  (f) $C_{3-10}$cycloalkyl,
  (g) $C_{1-10}$alkanoyl, and
  (h) benzoyl or mono-, di-, or trisubstituted benzoyl wherein the substituents are independently selected from halo, $C_{1-10}$alkyl, $C_{1-10}$alkoxy, $C_{1-10}$alkylthio, $C_{1-10}$alkyl$CO_2H$, —$C_{1-10}$aklyl$NH_2$, CN, $CO_2H$ and $CF_3$, each $R^{10}$ is independently selected from the group consisting of
  (a) hydrogen and
  (b) $R^{11}$;

$R^{11}$ is selected from the group consisting of
  (a) $C_{1-10}$alkyl,
  (b) $C_{3-10}$cycloalkyl,
  (c) unsubstituted, mono-, di- or tri-substituted phenyl or naphthyl wherein the substituents are independently selected from the group consisting of
    (1) halo,
    (2) $C_{1-10}$alkoxy,
    (3) $C_{1-10}$alkylthio,
    (4) CN,
    (5) $CF_3$,
    (6) $C_{1-10}$alkyl,
    (7) $N_3$,
    (8) —$CO_2H$,
    (9) —$CO_2$—$C_{1-10}$alkyl,
    (10) —$C(R^{12})(R^{13})$—OH,
    (11) —$C(R^{12})(R^{13})$—O—$C_{1-4}$alkyl,
    (12) —$C_{1-6}$alkyl—$CO_2$—$R^{12}$,
    (13) benzyloxy,
    (14) —O—$(C_{1-10}$alkyl$)$—$CO_2R^{12}$, and
    (15) —O—$(C_{1-10}$alkyl$)$—$NR^{12}R^{13}$,
  (d) unsubstituted, mono-, di- or tri-substituted heteroaryl wherein the heteroaryl is a monocyclic aromatic ring of 5 atoms, said rings having one hetero atom which is S, O, or N, and optionally 1, 2, or 3 additional N atoms; or said heteroaryl atom which is N, and optionally 1, 2, or 3 additional N atoms, and wherein said substituents are independently selected from the group consisting of
    (1) halo,
    (2) $C_{1-10}$alkyl,
    (3) $C_{1-10}$alkoxy,
    (4) $C_{1-10}$alkylthio,
    (5) CN,
    (6) $CF_3$,
    (7) $N_3$,
    (8) —$C(R^{12})(R^{13})$—OH, and
    (9) —$C(R^{12})(R^{13})$—O—$C_{1-10}$alkyl;
  (e) unsubstituted, mono- or di-substituted benzoheterocycle in which the benzoheterocycle is a 5, 6, or 7-membered ring which contains 1 or 2 heteroatoms independently selected from O, S, or N and optionally a carbonyl group or a sulfonyl group, wherein said substituents are selected from the group consisting of
    (1) halo,
    (2) $C_{1-10}$alkyl,
    (3) $C_{1-10}$alkoxy,
    (4) $C_{1-10}$alkylthio,
    (5) CN,
    (6) $CF_3$,
    (7) $N_3$,
    (8) —$C(R^{12})(R^{13})$—OH, and
    (9) —$C(R^{12})(R^{13})$—O—$C_{1-10}$alkyl;
  (f) unsubstituted, mono- or di-substituted benzocarbocycle in which the carbocycle is a 5, 6, or 7-membered ring which optionally contains a carbonyl group, wherein said substituents are independently selected from the group consisting of
    (1) halo,
    (2) $C_{1-10}$alkyl,
    (3) $C_{1-10}$alkoxy,
    (4) $C_{1-10}$alkylthio,
    (5) CN,
    (6) $CF_3$,
    (7) $N_3$,
    (8) —$C(R^{12})(R^{13})$—OH, and (9) —C(R$^{12}$)(R$^{13}$)—O—C$_{1-10}$alkyl;
each R$^{12}$ or R$^{13}$ is independently selected from the group consisting of
  (a) hydrogen, and
  (b) C$_{1-10}$alkyl,
  or R$^{12}$ and R$^{13}$ together with the atom to which they are attached form a saturated monocyclic ring of 3, 4, 5, 6 or 7 atoms;
R$^{14}$ and R$^{15}$ are independently selected from the group consisting of:
  (a) hydrogen, and
  (b) C$_{1-10}$alkyl, or
  R$^{14}$ and R$^{15}$ together with the carbon to which they are attached form a carbonyl, —C(=S)—, or a saturated monocyclic carbon ring of 3, 4, 5, 6, or 7 atoms;
each R$^{16}$ is independently selected from the group consisting of hydrogen, C$_{1-6}$alkyl and unsubstituted or mono- or disubstituted benzyl, wherein the substituents are selected from halo, CN, C$_{1-6}$alkyl, C$_{1-6}$alkoxy, C$_{1-6}$alkylthio or C$_{1-6}$fluoroalkyl;
each R$^{17}$ is independently selected from the group consisting of
  (a) hydrogen and
  (b) R$^{18}$;
each R$^{18}$ is independently selected from the group consisting of
  (a) C$_{1-10}$alkyl,
  (b) —C$_{1-10}$alkyl—CO$_2$H
  (c) C$_{1-10}$alkyl—NH$_2$
  (d) phenyl or mono-, di- or tri-substituted phenyl wherein the substituents are independently selected from halo, C$_{1-10}$alkyl, C$_{1-10}$alkoxy, C$_{1-10}$alkylthio, C$_{1-10}$alkylCO$_2$H, C$_{1-10}$alkylNH$_2$, CN, CO$_2$H and CF$_3$,
  (e) benzyl or mono-, di- or tri-substituted benzyl wherein the substituents are independently selected from halo, C$_{1-10}$alkyl, C$_{1-10}$alkoxy, C$_{1-10}$alkylthio, C$_{1-10}$alkylCO$_2$H, C$_{1-10}$alkylNH$_2$, CN, CO$_2$H and CF$_3$,
  (f) C$_{3-10}$cycloalkyl,
  (g) H-(oxyethyl)n wherein n is 1 to 6.
  (h) C$_{1-10}$alkanoyl,
  (i) benzoyl or mono-, di-, or trisubstituted benzoyl wherein the substituents are independently selected from halo, C$_{1-10}$alkyl, C$_{1-10}$alkoxy, C$_{1-10}$alkylthio, C$_{1-10}$alkylCO$_2$H, —C$_{1-10}$alkylNH$_2$, CN, CO$_2$H and CF$_3$, and
  (j) —CONH—Ph—CO$_2$R$^{19}$; and
R$^{19}$ is selected from the group consisting of hydrogen or C$_{1-6}$alkyl.
Within this embodiment there is a genus of compounds wherein
R$^5$ is selected from the group consisting of
  (a) OR$^{17}$,
  (b) SR$^{18}$, and
  (c) NHS(O)$_2$R$^{18}$.
Within this genus there is a sub-genus of compounds wherein
Y is selected from the group consisting of
  (a) C(R$^6$)(R$^7$), and
  (b) O;
R$^1$ is selected from the group consisting of
  (a) S(O)$_2$CH$_3$, and
  (b) S(O)$_2$NHR$^8$;
R$^2$ is selected from the group consisting of
  (a) OR$^{11}$,
  (b) R$^{11}$,
  (c) a mono-, di-, tri- or tetra-substituted heterocycloalkyl group of 5, 6 or 7 members or a benzoheterocycle wherein said heterocycloalkyl or benzoheterocycle contains 1 or 2 heteroatoms selected from O, S, or N and optionally contains a carbonyl group or a sulfonyl group, and wherein said substituents are independently selected from the group consisting of
    (1) halo,
    (2) C$_{1-4}$alkyl,
    (3) C$_{1-4}$alkoxy,
    (4) C$_{1-4}$alkylthio,
    (5) CF$_3$, and
    (6) —C(R$^{12}$)(R$^{13}$)—OH;
  (d) phenylacetylene or mono- or di-substituted phenylacetylene wherein the substituents are independently selected from the group consisting of
    (1) halo,
    (2) C$_{1-4}$alkyl,
    (3) C$_{1-4}$alkoxy,
    (4) C$_{1-4}$alkylthio,
    (5) CF$_3$, and
    (6) —C(R$^{12}$)(R$^{13}$)—OH;
R$^3$ is hydrogen, C$_{1-4}$alkyl, CH$_2$OH, or C$_{1-6}$fluoroalkyl, F, CONH$_2$;
R$^4$ is
  (a) hydrogen,
  (b) C$_{1-4}$alkyl,
  (c) C$_{1-4}$alkoxy,
  (d) C$_{1-4}$alkylthio,
  (e) —OH,
  or R$^3$ and R$^4$ together with the carbon to which they are attached form a monocyclic ring of 3, 4, 5, 6, or 7 members which ring optionally contains one or two heteroatoms selected from O, S or N;
R$^5$ is selected from the group consisting of
  (a) OR$^{17}$, and
  (b) SR$^{18}$;
R$^6$ and R$^7$ are independently
  (a) hydrogen,
  (b) C$_{1-4}$alkyl, CH$_2$OH, CN, CH$_2$CN, C$_{1-4}$fluoroalkyl, CONH$_2$, F or OH,
  or R$^6$ and R$^7$ together with the carbon to which they are attached form a saturated monocyclic carbon ring of 3, 4, 5, 6 or 7 atoms;
each R$^8$ is independently selected from the group consisting of
  (a) hydrogen and
  (b) R$^9$;
each R$^9$ is independently selected from the group consisting of
  (a) C$_{1-4}$alkyl,
  (b) —C$_{1-4}$alkyl—CO$_2$H
  (c) phenyl or mono-, di- or tri-substituted phenyl wherein the substituents are independently selected from halo, C$_{1-4}$alkyl, C$_{1-4}$alkoxy, C$_{1-4}$alkylthio, C$_{1-4}$alkylCO$_2$H, C$_{1-4}$alkylNH$_2$, CN, CO$_2$H and CF$_3$,
  (f) C$_{3-6}$cycloalkyl,
  (g) C$_1$–C$_4$ alkanoyl, and
  (h) benzoyl or mono-, di-, or trisubstituted benzoyl wherein the substituents are independently selected from halo, C$_{1-4}$alkyl, C$_{1-4}$alkoxy, C$_{1-4}$alkylthio, C$_{1-4}$alkylCO$_2$H, —C$_{1-4}$alkylNH$_2$, CN, CO$_2$H and CF$_3$, $R^{11}$ is selected from the group consisting of
  (a) unsubstituted, mono- or di-substituted phenyl wherein the substituents are independently selected from the group consisting of
    (1) halo,
    (2) $C_{1-4}$alkoxy,
    (3) $C_{1-4}$alkylthio,
    (5) $CF_3$,
    (6) $C_{1-4}$alkyl,
    (7) —$CO_2H$,
    (8) —$CO_2$—$C_{1-6}$alkyl,
    (9) —$C(R^{12})(R^{13})$—OH,
  (d) unsubstituted, mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
    (1) halo,
    (2) $C_{1-4}$alkoxy,
    (3) $C_{1-4}$alkylthio,
    (4) $CF_3$,
    (5) $C_{1-4}$alkyl,
    (6) —$CO_2H$,
    (7) —$CO_2$—$C_{1-6}$alkyl,
    (8) —$C(R^{12})(R^{13})$—OH,
  (e) unsubstituted, mono- or di-substituted benzoheterocycle in which the benzoheterocycle is a 5, 6, or 7-membered ring which contains 1 or 2 heteroatoms independently selected from O, S, or N and optionally a carbonyl group or a sulfonyl group, wherein said substituents are selected from the group consisting of
    (1) halo,
    (2) $C_{1-4}$alkoxy,
    (3) $C_{1-4}$alkylthio,
    (4) $CF_3$,
    (5) $C_{1-4}$alkyl,
    (6) —$CO_2H$,
    (7) —$CO_2$—$C_{1-6}$alkyl,
    (8) —$C(R^{12})(R^{13})$—OH,
  (f) unsubstituted, mono- or di-substituted benzocarbocycle in which the carbocycle is a 5, 6, or 7-membered ring which optionally contains a carbonyl group, wherein said substituents are independently selected from the group consisting of
    (1) halo,
    (2) $C_{1-4}$alkoxy,
    (3) $C_{1-4}$alkylthio,
    (4) $CF_3$,
    (5) $C_{1-4}$alkyl,
    (6) —$CO_2H$,
    (7) —$CO_2$—$C_{1-6}$alkyl,
    (8) —$C(R^{12})(R^{13})$—OH,
each $R^{12}$ or $R^{13}$ is independently selected from the group consisting of
  (a) hydrogen, and
  (b) $C_{1-6}$alkyl,
each $R^{17}$ is independently selected from the group consisting of
  (a) hydrogen and
  (b) $R^{18}$; and
each $R^{18}$ is independently selected from the group consisting of
  (a) $C_{1-4}$alkyl,
  (b) —$C_{1-4}$alkyl—$CO_2H$
  (c) $C_{1-6}$alkanoyl, and
  (d) H—(oxyethyl)n wherein n is 1 to 4.

Within this sub-genus there is a class of compounds wherein

Y is selected from the group consisting of
  (a) $C(R^6)(R^7)$, and
  (b) O;
$R^1$ is selected from the group consisting of
  (a) $S(O)_2CH_3$, and
  (b) $S(O)_2NH_2$;
$R^2$ is selected from the group consisting of
  (a) $OR^{11}$,
  (b) $R^{11}$,
  (c) a mono- or di-substituted heterocycloalkyl group 5 or 6 members wherein said heterocycloalkyl contains 1 or 2 heteroatoms which is N and optionally contains a carbonyl group, and wherein said substituents are independently selected from the group consisting of
    (1) Cl or F,
    (2) $C_{1-2}$alkyl, and
    (3) $C_{1-2}$alkoxy,
  (d) phenylacetylene or mono- or di-substituted phenylacetylene wherein the substituents are independently selected from the group consisting of
    (1) Cl or F,
    (2) $C_{1-2}$alkyl, and
    (3) $C_{1-2}$alkoxy,
$R^3$ is hydrogen, $C_{1-3}$alkyl;
$R^4$ is hydrogen, $C_{1-3}$alkyl;
  or $R^3$ and $R^4$ together with the carbon to which they are attached form a monocyclic ring of 3, 4, 5 or 6 carbon atoms;
$R^5$ is selected from the group consisting of
  (a) $OR^{17}$, and
  (b) $SR^{18}$;
$R^6$ and $R^7$ are independently
  (a) hydrogen,
  (b) $C_{1-3}$alkyl, $CH_2OH$, $C_{1-3}$fluoroalkyl, $CONH_2$, F or OH,
  or $R^6$ and $R^7$ together with the carbon to which they are attached form a saturated monocyclic carbon ring of 3, 4, 5 or 6;
each $R^8$ is independently selected from the group consisting of
  (a) hydrogen and
  (b) $R^9$;
each $R^9$ is independently selected from the group consisting of
  (a) $C_{1-4}$alkyl,
  (b) —$C_{1-4}$alkyl—$CO_2H$
  (f) $C_{3-6}$cycloalkyl, and
  (g) $C_{1-3}$alkanoyl,
$R^{11}$ is selected from the group consisting of
  (a) unsubstituted, mono- or di-substituted phenyl wherein the substituents are independently selected from the group consisting of
    (1) F of Cl,
    (2) $C_{1-4}$alkoxy,
    (3) $C_{1-4}$alkylthio,
    (5) $CF_3$,
    (6) $C_{1-4}$alkyl, and
    (7) —$CO_2H$, (d) unsubstituted, mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
  (1) F or Cl,
  (2) $C_{1-4}$alkoxy,
  (3) $C_{1-4}$alkylthio,
  (5) $CF_3$,
  (6) $C_{1-4}$alkyl, and
  (7) —$CO_2H$, (e) unsubstituted, mono- or di-substituted benzoheterocycle in which the benzoheterocycle is a 5 or 6-membered ring which contains 1 or 2 heteroatoms independently selected from O, S, or N and optionally a carbonyl group or a sulfonyl group, wherein said substituents are selected from the group consisting of
  (1) F of Cl,
  (2) $C_{1-4}$alkoxy,
  (3) $C_{1-4}$alkylthio,
  (5) $CF_3$,
  (6) $C_{1-4}$alkyl, and
  (7) —$CO_2H$, (f) unsubstituted, mono- or di-substituted benzocarbocycle in which the carbocycle is a 5 or 6-membered ring which optionally contains a carbonyl group, wherein said substituents are independently selected from the group consisting of
  (1) F or Cl,
  (2) $C_{1-4}$alkoxy,
  (3) $C_{1-4}$alkylthio,
  (5) $CF_3$,
  (6) $C_{1-4}$alkyl, and
  (7) —$CO_2H$, each $R^{17}$ is independently selected from the group consisting of
  (a) hydrogen and
  (b) $R^{18}$; and each $R^{18}$ is independently selected from the group consisting of
  (a) $C_{1-4}$alkyl,
  (b) —$C_{1-4}$alkyl—$CO_2H$
  (c) $C_{1-6}$alkanoyl, and
  (d) H—(oxyethyl)n wherein n is 1 to 4.

Within this class there is a sub-class of compounds wherein
Y is selected from the group consisting of
  (a) $CH_2$, and
  (b) O;
$R^1$ is selected from the group consisting of
  (a) $S(O)_2CH_3$, and
  (b) $S(O)_2NH_2$;
$R^2$ is selected from the group consisting of
  (a) $OR^{11}$,
  (b) $R^{11}$,
  (c) a mono- or di-substituted heterocycloalkyl group of 5 or 6 members wherein said heterocycloalkyl contains 1 or 2 heteroatoms which is N and optionally contains a carbonyl group, and wherein said substituents are independently selected from the group consisting of
    (1) Cl or F,
    (2) $C_{1-2}$alkyl, and
    (3) $C_{1-2}$alkoxy,
$R^3$ hydrogen, methyl or ethyl;
$R^4$ is hydrogen, methyl or ethyl;
$R^5$ is $OR^{17}$;
$R^{11}$ is selected from the group consisting of
  (a) unsubstituted, mono- or di-substituted phenyl wherein the substituents are independently selected from the group consisting of
    (1) F or Cl,
    (2) $C_{1-4}$alkoxy,
    (3) $C_{1-4}$alkylthio,
    (5) $CF_3$,
    (6) $C_{1-4}$alkyl, and
    (7) —$CO_2H$,
  (b) unsubstituted, mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
    (1) F or Cl,
    (2) $C_{1-4}$alkoxy,
    (3) $C_{1-4}$alkylthio,
    (5) $CF_3$,
    (6) $C_{1-4}$alkyl, and
    (7) —$CO_2H$, each $R^{17}$ is independently selected from the group consisting of
  (a) hydrogen and
  (b) $R^{18}$; and
each $R^{18}$ is independently selected from the group consisting of
  (a) $C_{1-4}$alkyl,
  (b) —$C_{1-4}$alkyl—$CO_2H$
  (c) $C_{1-6}$alkanoyl, and
  (d) H-(oxyethyl)n wherein n is 2, 3 or 4.

Also within this class there is a sub-class of compounds wherein
$R^2$ is a mono- or di-substituted heteroaryl wherein heteroaryl is selected from the group consisting of
  (1) furanyl,
  (2) diazinyl,
  (3) imidazolyl,
  (4) isooxazolyl,
  (5) isothiazolyl,
  (6) oxadiazolyl,
  (7) oxazolyl,
  (8) pyrazolyl,
  (9) pyridyl,
  (10) pyrrolyl,
  (11) tetrazinyl
  (12) tetrazolyl.
  (13) thiadiazolyl,
  (14) thiazolyl,
  (15) thienyl,
  (16) triazinyl, or
  (17) triazolyl, and the substituents are selected from the group consisting of (1) hydrogen,
(2) halo,
(3) $C_{1-4}$alkyl,
(4) $C_{1-4}$alkoxy,
(5) $C_{1-4}$alkylthio,
(6) CN, and
(7) $CF_3$.

Within this sub-class are the compounds wherein $R^2$ is a mono- or di-substituted heteroaryl wherein heteroaryl is selected from the group consisting of
(1) furanyl,
(2) diazinyl,
(3) imidazolyl,
(4) oxadiazolyl,
(5) pyrazolyl,
(6) pyridyl,
(7) pyrrolyl,
(8) thiazolyl,
(9) thienyl, wherein the substituents are selected from the group consisting of
  (1) hydrogen,
  (2) halo,
  (3) methyl,
  (4) methoxy, and
  (5) $CF_3$.

For purposes of this specification, in situations in which a term occurs two or more times such as "$R^8$" in "$CONR^8_2$," or $R^{16}$" in "$OP(O)(OR^{16})_2$,", the definition of the term in each occurrence is independent of the definition in each additional occurrence. Similarly, each occurrence of definitions such as $R^{12}$ and $R^{13}$ are to be considered independent of each additional occurrence.

For purposes of this specification heteroaryl is in $R^3$, $R^6$, $R^7$ and $R^{11}$ is intended to include, but is not limited to optionally mono- or di-substituted
(1) furanyl,
(2) diazinyl,
(3) imidazolyl,
(4) isooxazolyl,
(5) isothiazolyl,
(6) oxadiazolyl,
(7) oxazolyl,
(8) pyrazolyl,
(9) pyridyl,
(10) pyrrolyl,
(11) tetrazinyl,
(12) tetrazolyl,
(13) thiadiazolyl,
(14) thiazolyl,
(15) thienyl,
(16) triazinyl, and
(17) triazolyl.

Similarly, for purposes of this specification cyclic groups such as a heterocycloalkyl or benzocarbocycle or benzoheterocycle such as in $R^2$ and $R^{11}$ is intended to include, but is not limited to optionally mono- or di-substituted
(1) tetrahydrothiopyranyl,
(2) thiomorpholinyl, (3) pyrrolidinyl,
(4) hexahydroazepinyl,
(5) indanyl,
(6) tetralinyl,
(7) indolyl,
(8) benzofuranyl,
(9) benzothienyl,
(10) benzimidazolyl,
(11) benzothiazolyl,

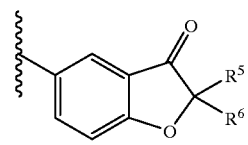

(12)

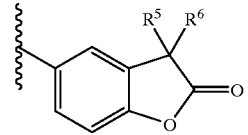

(13)

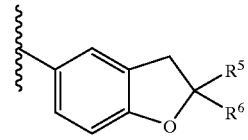

(14)

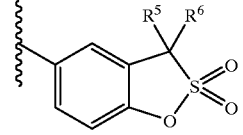

(15)

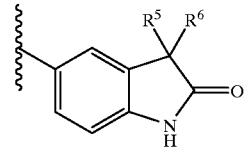

(16)

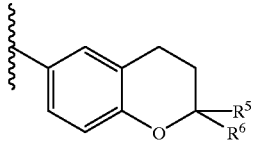

(17)

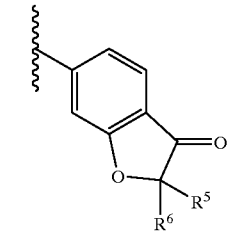

(18)

-continued
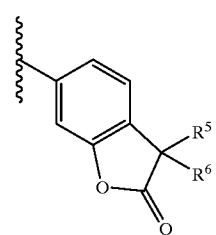 (19)
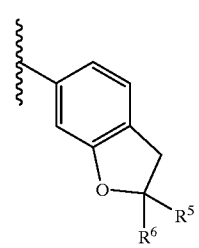 (20)
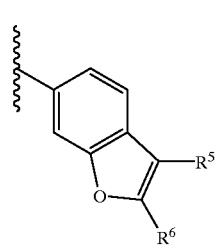 (21)
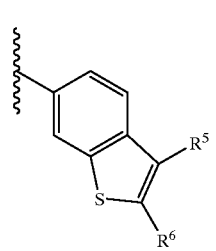 (22)
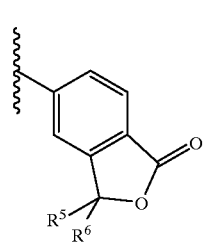 (23)
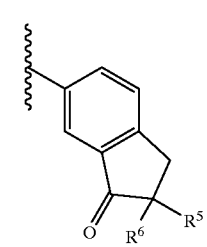 (24)
-continued
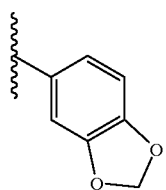 (25)
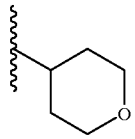 (26)
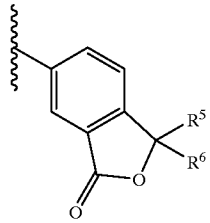 (27)
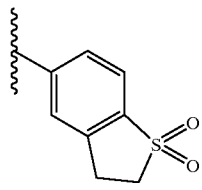 (28)
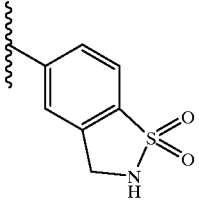 (29)
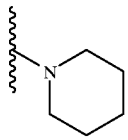 (30)
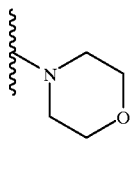 (31)
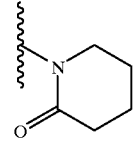 (32)

(33)
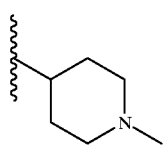
Similarly, for purposes of this specification bicyclic heteroaryl as in R² is intended to include, but is not limited to optionally mono- or di-substituted
(1)
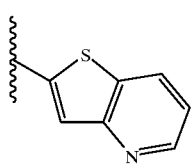
(2)
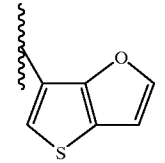
(3)
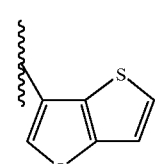
(4)
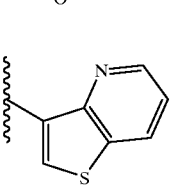
(5)
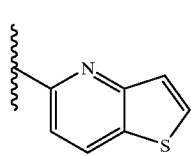
(6)
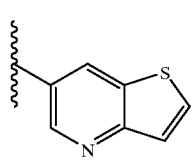
(7)
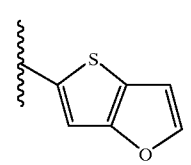
(8)
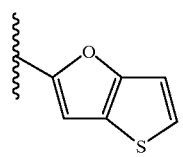
(9)
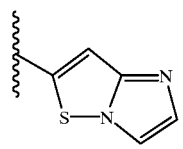
(10)
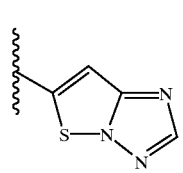
(11)
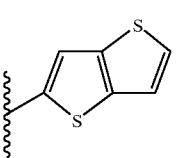
(12)
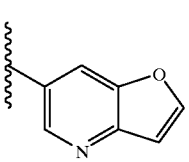
(13)
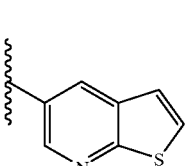
(14)
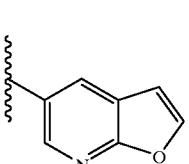
(15)
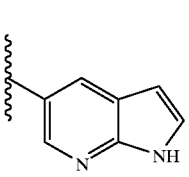
(16)
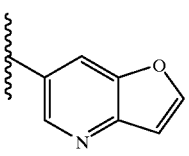

-continued

(17) 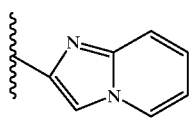

(18) 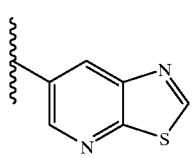

(19) 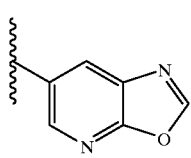

(20) 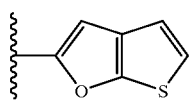

(21) 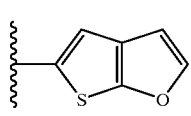

One preferred genus is directed to the compounds of formula I wherein Y is O.

Another preferred genus is directed to compounds of Formula I wherein $R^3$ and $R^4$ are each hydrogen.

Another preferred genus is directed to compounds of Formula I wherein $R^3$ is methyl and $R^4$ is methyl or ethyl.

Another preferred genus is directed to compounds of Formula I wherein $R^2$ is a phenyl or substituted phenyl.

Another preferred genus is directed to compounds of Formula I wherein $R^2$ is a $OR^{11}$.

Another preferred genus is directed to compounds of Formula I $R^5$ is hydroxy.

The invention is illustrated by the compounds of the Examples disclosed herein as well as the compounds of Table I:

(a) 5,5-Dimethyl-3-(3-fluorophenyl)-2-hydroxy-4-(4-(methylsulfonyl)phenyl)-2,5-dihydrofuran,
(b) 3-(3,5-Difluorophenyl)-5,5-dimethyl-2-hydroxy-4-(4-(methylsulfonyl)phenyl)-2,5-dihydrofuran,
(c) 5,5-Dimethyl-3-(4-fluorophenyl)-2-hydroxy-4-(4-(methylsulfonyl)phenyl)-2,5-dihydrofuran,
(d) 5,5-Dimethyl-3-(4-fluorophenyl)-2-methoxy-4-(4-(methylsulfonyl)phenyl)-2,5-dihydrofuran,
(e) 5,5-Dimethyl-2-ethoxy-3-(3-fluorophenyl)-4-(4-(methylsulfonyl)phenyl)-2,5-dihydrofuran,
(f) 5,5-Dimethyl-3-(3-fluorophenyl)-2-isopropoxy-4-(4-(methylsulfonyl)phenyl)-2,5-dihydrofuran,
(g) 5,5-Dimethyl-3-(3-fluorophenyl)-4-(4-(methylsulfonyl)phenyl)-2-methylthio-2,5-dihydrofuran,
(h) 5-Ethyl-3-(4-fluorophenyl)-2-hydroxy-5-methyl-4-(4-(methylsulfonyl)phenyl)-2,5-dihydrofuran,
(i) 5,5-Dimethyl-3-(3-fluorophenoxy)-2-hydroxy-4-(4-(methylsulfonyl)phenyl)-2,5-dihydrofuran,
(j) 5,5-Dimethyl-3-(3,4-difluorophenoxy)-2-hydroxy-4-(4-(methylsulfonyl)phenyl)-2,5-dihydrofuran,
(k) 3-(3,4-Difluorophenyl)-2-hydroxy-4-(4-(methylsulfonyl)phenyl)-2,5-dihydrofuran,
(l) 2-(4-Fluorophenyl)-3-(4-(methylsulfonyl)phenyl)-2-cyclopenten-1-ol,
(m) 3-(4-(Methylsulfonyl)phenyl)-2-phenyl-2-cyclopenten-1-ol,
(n) 2-Acetoxy-5,5-dimethyl-3-(3-fluorophenyl)-4-(methylsulfonyl)phenyl)-2,5-dihydrofuran,
(o) 2-(3,5-Difluorophenyl)-3-(4-(methylsulfonyl)phenyl)-2-cyclopenten-1-ol,
(p) Sodium (5,5-dimethyl-3-(3-fluorophenyl)-4-(4-(methylsulfonyl)phenyl-2,5-dihydrofuran-2-yloxy) actetate, and
(q) Succinic acid mono-(3-(4-(methylsulfonyl)phenyl)-2-phenyl-cyclopent-2-enyl) ester.

The following abbreviations have the indicated meanings:

| | | |
|---|---|---|
| AA | = | arachidonic acid |
| Ac | = | acetyl |
| AIBN | = | 2.2-azobisisobutyronitrile |
| Bn | = | benzyl |
| CHO | = | chinese hamster ovary |
| CMC | = | 1-cyclohexyl-3-(2-morpholinoethyl) carbodiimidemetho-p-toluenesulfonate |
| COX | = | cyclooxygenase |
| DBU | = | diazabicyclo[5.4.0]undec-7-ene |
| DMAP | = | 4-(dimethylamino)pyridine |
| DMF | = | N,N-dimethylformamide |
| DMSO | = | dimethyl sulfoxide |
| $Et_3N$ | = | triethylamine |
| HBSS | = | Hanks balanced salt solution |
| HEPES | = | N-[2-Hydroxyethyl]piperazine-$N^1$-[2-ethanesulfonic acid] |
| HWB | = | human whole blood |
| KHMDS | = | potassium hexamethyldisilazane |
| LDA | = | lithium diisopropylamide |
| LPS | = | lipopolysaccharide |
| mCPBA | = | metachloro perbenzoic acid |
| MMPP | = | magnesium monoperoxyphthalate |
| Ms | = | methanesulfonyl = mesyl |
| MsO | = | methanesulfonate = mesylate |
| NBS | = | N-bromosuccinimide |
| NCS | = | N-chlorosuccinimide |
| NIS | = | N-iodosuccinimide |
| NSAID | = | non-steroidal anti-inflammatory drug |
| Oxone ® | = | potassium peroxymonosulfate |
| PCC | = | pyridinium chlorochromate |
| PDC | = | pyridinium dichromate |
| r.t. | = | room temperature |
| rac. | = | racemic |
| Tf | = | trifluoromethanesulfonyl = triflyl |
| TFAA | = | trifluoroacetic anhydride |
| TfO | = | trifluoromethanesulfonate = triflate |
| THF | = | tetrahydrofuran |
| TLC | = | thin layer chromatography |
| TMPD | = | N,N,N',N'-tetramethyl-p-phenylenediamine |
| Ts | = | p-toluenesulfonyl = tosyl |
| TsO | = | p-toluenesulfonate = tosylate |
| Tz | = | 1H (or 2H)-tetrazol-5-yl |
| $SO_2Me$ | = | methyl sulfone (also $SO_2CH_3$) |
| $SO_2NH_2$ | = | sulfonamide |

| Alkyl group abbreviations | | | Dose Abbreviations |
|---|---|---|---|
| Me | = | methyl | bid = bis in die = twice daily |
| Et | = | ethyl | qid = quater in die = four times a day |
| n-Pr | = | normal propyl | tid = ter in die = three times a day |
| i-Pr | = | isopropyl | |
| n-Bu | = | normal butyl | |
| i-Bu | = | isobutyl | |
| s-Bu | = | secondary butyl | |

-continued

| Alkyl group abbreviations | | Dose Abbreviations |
|---|---|---|
| t-Bu | = | tertiary butyl |
| c-Pr | = | cyclopropyl |
| c-Bu | = | cyclobutyl |
| c-Pen | = | cyclopentyl |
| c-Hex | = | cyclohexyl |

For purposes of this specification alkyl, alkenyl and alkynyl means linear branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0] decyl and the like.

For purposes of this specification fluoro alkyl means alkyl groups in which one or more hydrogen is replaced by fluorine. Examples are —$CF_3$, —$CH_2CH_2F$, —$CH_2CF_3$, c—$Pr$—$F_5$, c—$Hex$—$F_{11}$ and the like.

Fluoroalkenyl includes alkenyl groups in which one or more hydrogen is replaced by fluorine. Examples are —CH=$CF_2$, —CH=$CHCF_3$, —C($CF_3$)=$CMe_2$, —CH=C($CH_3$)$CH_2CF_3$, —CH=CH($CH_2F$) and the like.

Cycloalkyl refers to a hydrocarbon, containing one or more rings having the indicated number of carbon atoms. Examples of cycloalkyl groups are cyclopropyl, cyclopentyl, cycloheptyl, aldamantyl, cyclododecyl, 1-bicyclo[4.4.0]decyl and the like.

Examples of alkenyl groups include vinyl, allyl, isopropenyl, pentenyl, hexenyl, heptenyl, 1-propenyl, 2-butenyl, 2-methyl-2-butenyl, 5-decen-1-yl, 2-dodecen-1-yl and the like.

For purposes of this specification, cycloalkenyl means alkenyl groups of the indicated number of carbon atoms, which include a ring, and in which the alkenyl double bond may be located anywhere in the structure. Examples of cycloalkenyl groups are cyclopropen-1-yl, cyclohexen-3-yl, 2-vinyladamant-1-yl, 5-methylenecyclododec-1-yl, and the like.

For purposes of this specification, the term alkynyl and means an alkynyl groups of the indicated number of carbon atoms. Examples of alkynyl groups include ethynyl, propargyl, 3-methyl-1-pentynyl, 2-heptynyl, 2-pentadecyn-1-yl, 1-eicosyn-1-yl, and the like.

For purposes of this specification, cycloalkynyl means groups of 5 to 20 carbon atoms, which include a ring of 3 to 20 carbon atoms. The alkynyl triple bond may be located anywhere in the group, with the proviso that if it is within a ring, such a ring must be 10 members or greater. Examples of "cycloalkynyl" are cyclododecyn-3-yl, 3-cyclohexyl-1-propyn-1-yl, and the like.

For purposes of this specification alkoxy means alkoxy groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like.

For purposes of this specification alkylthio means alkylthio groups of the indicated number of carbon atoms of a straight, branched or cyclic configuration. Examples of alkylthio groups include methylthio, propylthio, isopropylthio, cycloheptylthio, etc. By way of illustration, the propylthio group signifies —$SCH_2CH_2CH_3$.

For purposes of this specification Halo means F, Cl, Br, or I.

For purposes of this specification, the heterocycles formed when $R^{12}$ and $R^{13}$ join through N include azetidine, pyrrolidine, piperidine, and hexahydroazepine.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumour growth and hence can be used in the treatment of cancer. Compound I may also be of use in the treatment and/or prevention of cyclooxygenase-mediated proliferative disorders such as may occur in diabetic retinopathy and tumour angiogenesis.

Compound I, by virtue of its in vivo conversion to a COX-2 inhibitor, will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis), and for treatment of glaucoma.

The compounds of Formula I are prodrugs of selective COX-2 inhibitors, and exert their action by conversion in vivo to these active and selective COX-2 inhibitors. The active compounds formed from the compounds of the present invention are described in the following documents which are hereby encorporated by reference:

WO 95/00501, published Jan. 5, 1995.

In certain respects, compounds of the present invention have advantages over the compounds described in these documents by virtue of improved pharmacokinetic and/or safety profiles. A general description of the advantages and uses of prodrugs as pharmaceutically useful compounds is given in an article by Waller and George in *Br. J. Clin. Pharmac.* Vol. 28, pp. 497–507, 1989.

By way of illustration, the following compounds of the present invention are converted to the indicated COX-2 selective inhibitors.

| Example | Prodrug | Active Drug | Reference |
|---|---|---|---|
| 1 | | | WO 95/00501 |
| 10 | | | |
| 13 | | | WO 95/00501 |
| 5 | | | WO 95/00501 |
| 39 | | | |
| 40 | | | WO 95/00501 |

By virtue of its in vivo conversion to a compound with high inhibitory activity against COX-2 and/or a specificity for COX-2 over COX-1, compound I will prove useful as an alternative to conventional NSAID'S, particularly where such non-steroidal antiinflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment which follows, references to the compounds of Formula I are meant to also include the pharmaceutically acceptable salts.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis) and for the treatment of glaucoma.

By virtue of its high cyclooxygenase-2 (COX-2) activity and/or its specificity for cyclooxygenase-2 over cyclooxygenase-1 (COX-1), Compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including a acetominophen or phenacetin; a potentiator including caffeine; and $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene, glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods

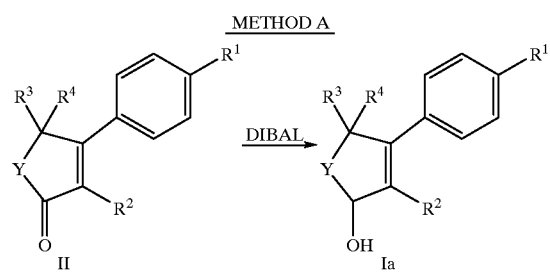

Compound Ia may be prepared by the treatment of a THF solution of carbonyl compound II (WO 9500501, published Jun. 5, 1995) with a reducing agent such as DIBAL at 0° C. See also the starting materials section which follows the Examples.

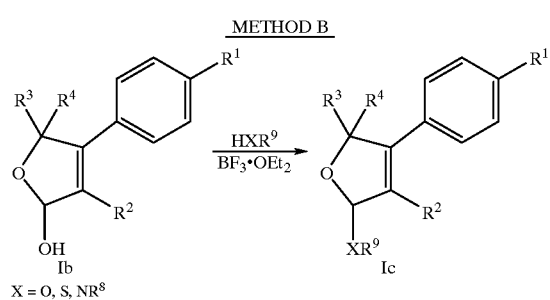

Compound Ic may be prepared by the treatment of lactol Ib with an appropriate alcohol, mercaptan or amine in the presence of an acid catalyst such as $BF_3 \bullet OEt_2$ or $H_2SO_4$.

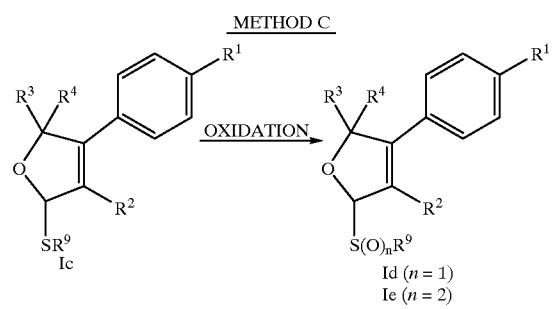

Compounds Id and Ie may be prepared by treatment of sulfide Ic with one or two equivalents respectively of an oxidizing agent such as OXONE, mCPBA or MMPP.

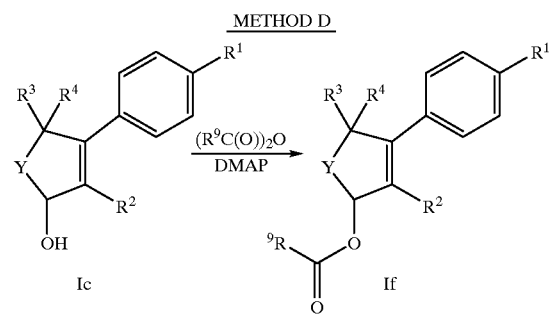

Compound If may be prepared by treatment of compound Ia with an acid anhydride in the presence of DMAP.

METHOD E

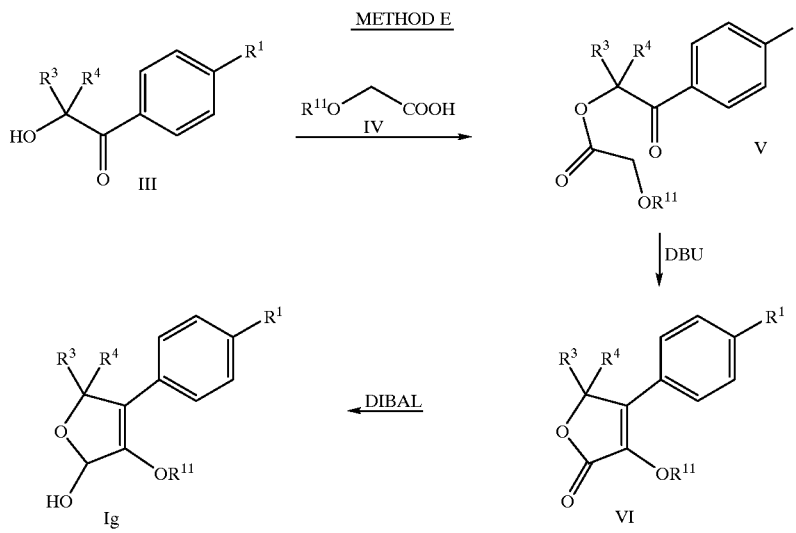

An appropriately substituted aryl dialkylhydroxyketone III is reacted with an appropriately substituted acetic acid IV in a solvent such as dichloromethane in the presence of an esterifying agent such as 1-cyclohexyl-3-(2-morpholinoethyl)carbodiimide metho-p-toluenesulfonate (CMC) and N,N-dimethylaminopyridine to provide ester V. Treatment with 1,8-diazabicyclo[5.4.0]undec-7-ene (DBU) then affords lactone VI. Subsequent reduction of VI as indicated in Method A provides Ig which is an example of the current invention.

METHOD F

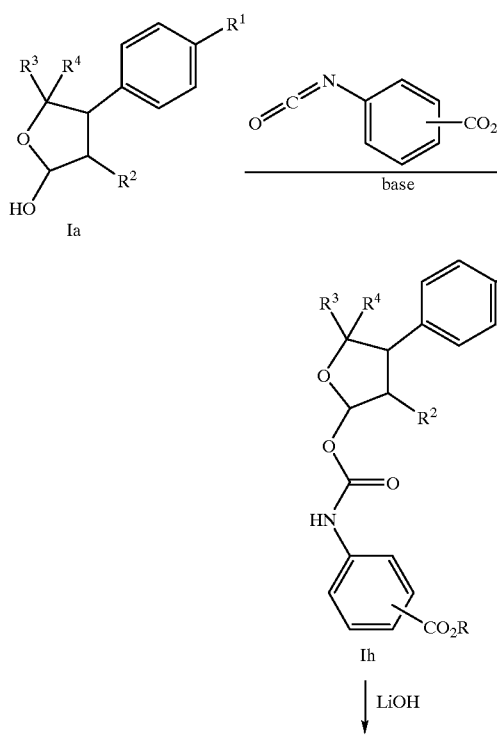

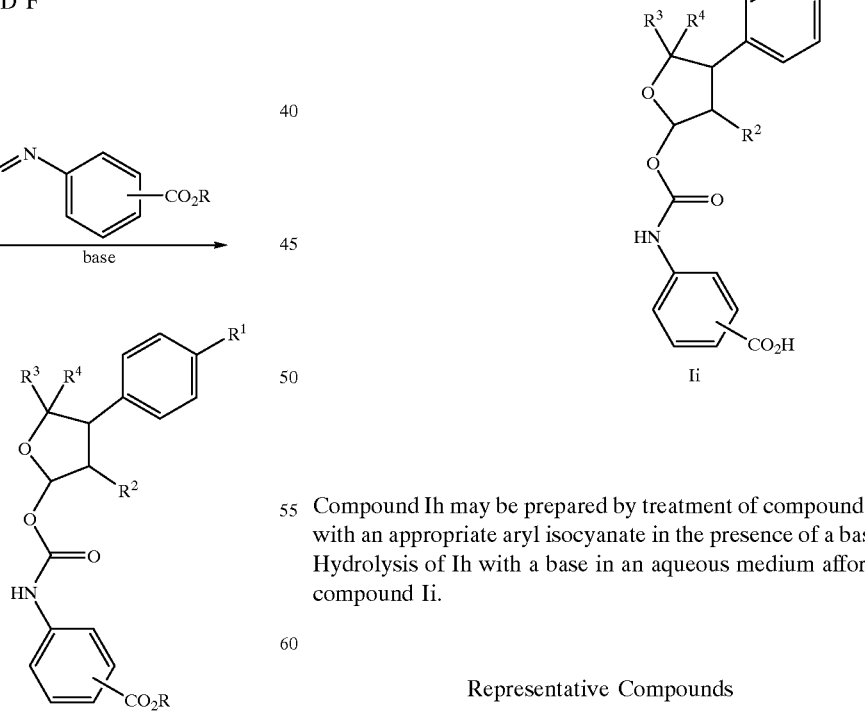

Compound Ih may be prepared by treatment of compound Ia with an appropriate aryl isocyanate in the presence of a base. Hydrolysis of Ih with a base in an aqueous medium affords compound Ii.

Representative Compounds

Table I illustrates compounds of formula I, which are representative of the present invention.

TABLE I

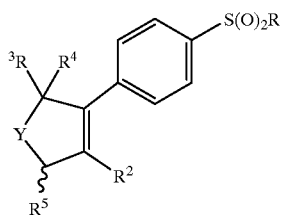

| Example | R | R² | R³ | R⁴ | R⁵ | Y | Method |
|---|---|---|---|---|---|---|---|
| 1 | Me | 3-F-Ph | Me | Me | OH | O | A |
| 2 | Me | 3,5-F₂-Ph | Me | Me | OH | O | A |
| 3 | Me | 4-F-Ph | Me | Me | OH | O | A |
| 4 | Me | 4-F-Ph | Me | Me | OMe | O | B |
| 5 | Me | 3-F-Ph | Me | Me | OEt | O | B |
| 6 | Me | 3-F-Ph | Me | Me | OiPr | O | B |
| 7 | Me | 3-F-Ph | Me | Me | SMe | O | B |
| 8 | Me | 3-F-Ph | Et | Me | OH | O | A |
| 9 | Me | 3-F-PhO | Me | Me | OH | O | E |
| 10 | Me | 3,4-F₂-PhO | Me | Me | OH | O | E |
| 11 | Me | 3,4-F₂-Ph | H | H | OH | O | A |
| 12 | Me | 4-F-Ph | H | H | OH | CH₂ | A |
| 13 | Me | Ph | H | H | OH | CH₂ | A |
| 14 | Me | 3-F-Ph | Me | Me | OAc | O | D |
| 15 | Me | 2,6-F₂-Ph | Me | Me | OH | O | A |
| 16 | Me | 3-Cl-Ph | H | H | OH | CH₂ | A |
| 17 | Me | 3,5-F₂-Ph | H | H | OH | CH₂ | A |
| 18 | Me | 3,5-Cl₂-Ph | H | H | OH | CH₂ | A |
| 19 | NH₂ | 3,5-F₂-Ph | Me | Me | OH | O | A |

| Example | | Method |
|---|---|---|
| 20 | 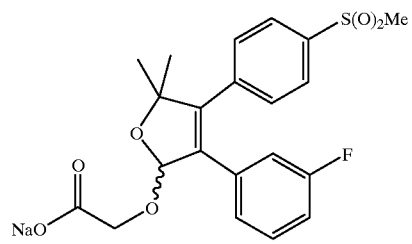 | B |
| 21 | 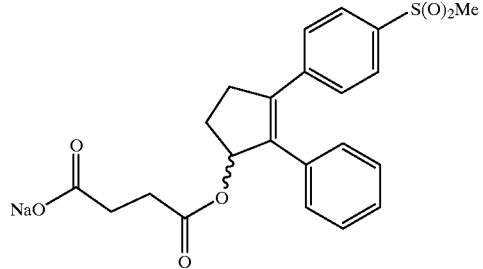 | D |
| 22 | 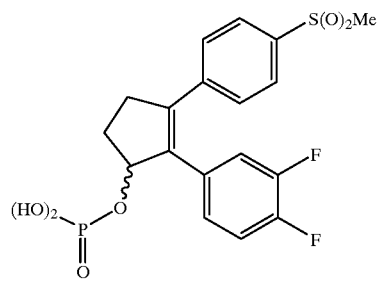 | |

TABLE I-continued
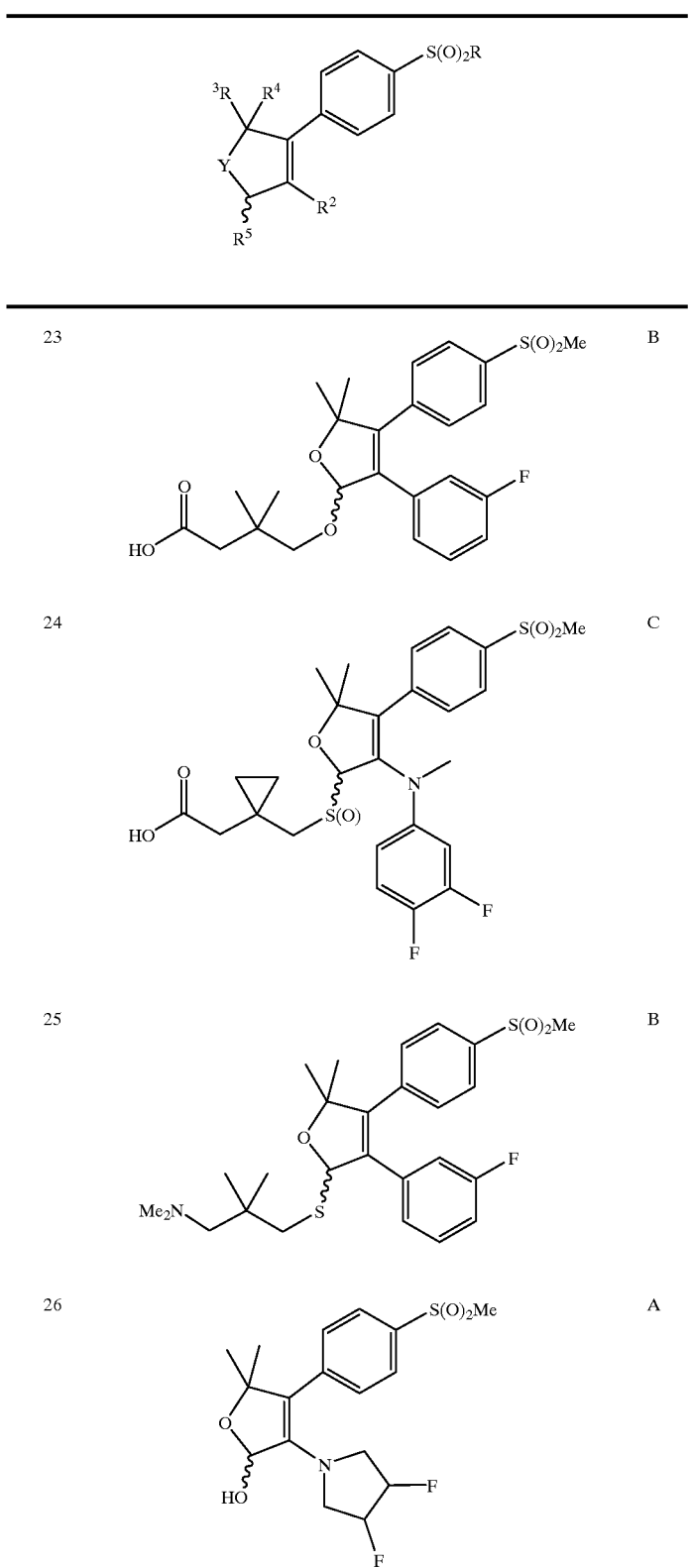

TABLE I-continued

| | Structure | |
|---|---|---|
| 27 | 2,2-dimethyl-3-(3-fluorophenyl)-4-(4-methylsulfonylphenyl)-5-(4-carboxyphenoxy)-2,5-dihydrofuran | B |
| 28 | 2,2-dimethyl-3-(3,4-difluorophenoxy)-4-(4-methylsulfonylphenyl)-5-(methylsulfonylamino)-2,5-dihydrofuran | B |
| 29 | 2,2-dimethyl-4-(4-methylsulfonylphenyl)-3-(2-phenylvinyl)-5-hydroxy-2,5-dihydrofuran | A |
| 30 | 2,2-dimethyl-4-(4-methylsulfonylphenyl)-3-(2-methyl-3,3,3-trifluoro-1-propenyl)-5-hydroxy-2,5-dihydrofuran | A |

Assays for Determining Biological Activity

The compound of Formula I can be tested using the following assays to determine their cyclooxygenase-2 inhibiting activity.

INHIBITION OF CYCLOOXYGENASE ACTIVITY

Compounds are tested as inhibitors of cyclooxygenase activity in whole cell cyclooxygenase assays. Both of these assays measure prostaglandin $E_2$ synthesis in response to arachidonic acid, using a radioimmunoassay. In these assays, 100% activity is defined as the difference between prostaglandin $E_2$ synthesis in the absence and presence of arachidonate.

Whole Cell Assays

For cyclooxygenase assays, osteosarcoma cells are cultured in 1 mL of media in 24-well multidishes (Nunclon) until confluent (1–2×10$^5$ cells/well). U-937 cells are grown in spinner flasks and resuspended to a final density of 1.5×10$^6$ cells/mL in 24-well multidishes (Nunclon). Following washing and resuspension of osteosarcoma and U-937 cells in 1 mL of HBSS, 1 μL of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 μL of this diluted solution is added to the cells to give a final arachidonic acid concentration of 10 μM. Control samples are incubated with ethanol vehicle instead of arachidonic acid. Samples are again gently mixed and incubated for a further 10 min. at 37° C. For osteosarcoma cells, reactions are then stopped by the addition of 100 μL of 1N HCl, with mixing and by the rapid removal of the solution from cell monolayers. For U-937 cells, reactions are stopped by the addition of 100 μL of 1N HCl, with mixing. Samples are then neutralized by the addition of 100 μL of 1N NaOH and PGE$_2$ levels measured by radioimmunoassay.

Whole Cell Assays for COX-2 and COX-1 Using CHO Transfected Cell Lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300× g, 10 min) and washed once in HBSS containing 15 mM HEPES, pH 7.4, and resuspended in HBSS, 15 mM HEPES, pH 7.4, at a cell concentration of 1.5×10$^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells (0.3×10$^6$ cells in 200 μl) are preincubated with 3 μl of the test drug or DMSO vehicle for 15 min at 37° C. Working solutions of peroxide-free AA (5.5 μM and 110 μM AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 μM AA in the CHO[hCOX-1] assay and a final concentration of 10 μM AA in the CHO[hCOX-2] assay. The reaction is terminated by the addition of 10 μl 1 N HCl followed by neutralization with 20 μl of 0.5 N NaOH. The samples are centrifuged at 300× g at 4° C. for 10 min, and an aliquot of the clarified supernatant is appropriately diluted for the determination of PGE$_2$ levels using an enzyme-linked immunoassay for PGE$_2$ (Correlate PGE$_2$ enzyme immunoassay kit, Assay Designs, Inc.). Cyclooxygenase activity in the absence of test compounds is determined as the difference in PGE$_2$ levels of cells challenged with arachidonic acid versus the PGE$_2$ levels in cells mock-challenged with ethanol vehicle. Inhibition of PGE$_2$ synthesis by test compounds is calculated as a percentage of the activity in the presence of drug versus the activity in the positive control samples.

Assay of COX-1 Activity from U937 Cell Microsomes

U937 cells are pelleted by centrifugation at 500× g for 5 min and washed once with phosphate-buffered saline and repelleted. Cells are resuspended in homogenization buffer consisting of 0.1 M Tris-HCl, pH 7.4, 10 mM EDTA, 2 μg/ml leupeptin, 2 μg/ml soybean trypsin inhibitor, 2 μg/ml aprotinin and 1 mM phenyl methyl sulfonyl fluoride. The cell suspension is sonicated 4 times for 10 sec and is centrifuged at 10,000× g for 10 min at 4° C. The supernatant is centrifuged at 100,000× g for 1 hr at 4° C. The 100,000× g microsomal pellet is resuspended in 0.1 M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 μg/ml in 0.1 M Tris-HCl buffer, pH 7.4 containing 10 mM EDTA, 0.5 mM phenol, 1 mM reduced glutathione and 1 μM hematin. Assays are performed in duplicate in a final volume of 250 μl. Initially, 5 μl of DMSO vehicle or drug in DMSO are added to 20 μl of 0.1 M Tris-HCl buffer, pH 7.4 containing 10 mM EDTA in wells of a 96-deepwell polypropylene titre plate. 200 μl of the microsomal preparation are then added and preincubated for 15 min at room temperature before addition of 25 μl of 1 M arachidonic acid in 0.1 M Tris-HCl and 10 mM EDTA, pH 7.4. Samples are incubated for 40 min at room temperature and the reaction is stopped by the addition of 25 μl of 1 N HCl. Samples are neutralized with 25 μl of 1 N NaOH prior to quantitation of PGE$_2$ content by radioimmunoassay (Dupont-NEN or Amersham assay kits). Cyclooxygenase activity is defined as the difference between PGE$_2$ levels in samples incubated in the presence of arachidonic acid and ethanol vehicle.

Assay of the Activity of Purified Human COX-2

The enzyme activity is measured using a chromogenic assay based on the oxidation of N,N,N',N'-tetramethyl-p-phenylenediamine (TMPD) during the reduction of PGG$_2$ to PGH$_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 μL) contains 100 mM sodium phosphate, pH 6.5, 2 mM genapol X-100, 1 μM hematin, 1 mg/ml gelatin, 80–100 units of purified enzyme (One unit of enzyme is defined as the amount of enzyme required to produce an O.D. change of 0.001/min at 610 nm) and 4 μL of the test compound in DMSO. The mixture is preincubated at room temperature (22° C.) for 15 minutes prior to initiation of the enzymatic reaction by the addition of 20 μL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2 mL blood aliquot to use as blank (basal levels of $PGE_2$). The remaining blood is incubated with LPS (100 μg/ml final concentration, Sigma Chem, #L-2630 from *E. coli*; diluted in 0.1% BSA (Phosphate buffered saline) for 5 minutes at room temperature. Five hundred μL aliquots of blood are incubated with either 2 μL of vehicle (DMSO) or 2 μL of a test compound at final concentrations varying from 10 nM to 30 μM for 24 hours at 37° C. At the end of the incubation, the blood is centrifuged at 12,000× g for 5 minutes to obtain plasma. A 100 μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000× g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 μl of 1% carrageenan solution in saline (FMC Corp, Maine) into the paw using an insulin syringe with a 25-gauge needle (i.e. 500 μg carrageenan per paw). Three hr later, the paw volume ($V_3$) is measured and the increases in paw volume ($V_3-V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in H$_2$O vehicles, (3 mL/kg b.i.d.) or test compounds at doses from 1–100 mg/kg b.i.d. for 5 days. Intravenous $^{51}$Cr (5 Ci/kg in 1 ml/kg phosphate buffer saline (PBS)) is administered 1 h after the last drug/vehicle dose, and feces collected for 24 h in a metabolism cage and assessed for excreted $^{51}$Cr by gamma-counting. Venous blood is sampled 1 h and 8 h after the last drug dose, and plasma concentrations of drug measured by RP-HPLC.

RAT PLASMA LEVELS

Per Os Pharmacokinetics in Rats

PROCEDURE

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box is firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles

The following vehicles may be used in PO rat blood level determinations:

PEG 200/300/400—restricted to 2 mL/kg

Methocel 0.5%–1.0% 10 mL/kg

Tween 80 5% 10 mL/kg

Compounds for PO blood levels can be suspension form. For better dissolution, the solution can be placed in a sonicator for approximately 5 minutes.

Intravenous Pharmacokinetics in Rats

PROCEDURE

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under CO$_2$ sedation. The rats, one at a time, are placed in a primed CO$_2$ chamber and taken out as soon as they had lost their righting reflex. The rat is then placed on a restraining board, a nose cone with CO$_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone was removed. The time is noted. This constituted the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick to tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles

The following vehicles may be used in IV rat blood level determinations:

Dextrose: 1 mL/kg

Molecusol 25%: 1 mL/kg

DMSO: (dimethylsulfoxide) Restricted to a dose volume of 0.1 mL per animal

PEG 200: Not more than 60% mixed with 40% sterile water—1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUC_{po}}{AUC_{iv}} \times \frac{DOSE_{iv}}{DOSE_{po}} \times 100\%$$

Clearance rates are calculated from the following relation:

$$Cl = \frac{DOSE_{iv}(\text{mg/kg})}{AUC_{iv}}$$

The units of Cl are mL/h·kg (milliliters per hour kilogram)

Representative Biological Data

Compounds of the present invention are prodrugs of inhibitors of COX-2 and are thereby useful in the treatment of COX-2 mediated diseases as enumerated above. The extent of conversion of these compounds to the active COX-2 inhibitors may be seen in the representative results shown below along with their antiinflammatory activity. The plasma levels indicated are the maximum rat plasma concentrations of the active COX-2 inhibitor observed when the rat was treated with a 20 mg/kg oral dose of the indicated prodrug. The ED$_{50}$ values in the rat paw edema assay represent the does of prodrug required to reduce edema formation by 50% as compared to the vehicle control.

TABLE 2

| Example | Plasma Levels ($\mu$M)* | Rat Paw Edema (ED$_{50}$, mg/kg) |
| --- | --- | --- |
| 1 | 7.5 | 2.5 |
| 2 | 3.9 | 0.7 |
| 9 | 0.7 | 1.7 |

TABLE 2-continued

| Example | Plasma Levels (μM)* | Rat Paw Edema (ED$_{50}$, mg/kg) |
|---|---|---|
| 10 | 16 | 0.09 |
| 13 | 27 | 0.9 |
| 39 | 18 | 2.7 |
| 40 | 45 | 1.5 |
| 44 | 4.6 | 1.6 |

*Maximum plasma concentration of the corresponding carbonyl compound observed in rats when dosed at 20 mg/kg orally with the indicated pro-drug.

* Maximum plasma concentration of the corresponding carbonyl compound observed in rats when dosed at 20 mg/kg orally with the indicated prodrug.

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.; in addition "Ar" signifies an aromatic signal;

(viii) chemical symbols have their usual means; the following abbreviations have also been used v (volume), w (weight), b.p. (boiling point), M.P. (melting point), L (liter(s)), mL (milliliters), g (gram (s)), mg (milligrams(s)), mol (moles), mmol (millimoles), eq (equivalent(s)).

EXAMPLE 1

5,5-Dimethyl-3-(3-fluorophenyl)-2-hydroxy-4-(4-methylsulfonylphenyl)-2,5-dihydrofuran (Method A)

Step 1 2-Hydroxy-4'-(methylsulfonyl)isobutyrophenone

To a solution of 2-hydroxy-4'-(methylthiol) isobutyrophenone (J. Org. Chem. 56, 5955–8, 1991) (45 g) in t-BuOH (500 mL) and $CH_2Cl_2$ (200 mL) was added a solution of OXONE™ (194 g) in $H_2O$ (1.4 L). The reaction mixture was stirred for 18 h at r.t. and then extracted with EtOAc (3×500 mL). The organic extracts were combined and dried over $Na_2SO_4$ and the solvent was evaporated. The residue was swished in ether/hexane to give the title compound as a yellow solid (47.4 g).

Step 2 3-Fluorophenylacetic acid, 1,1-dimethyl-2-(4-(methylsulfonyl)phenyl)-2-oxo-ethyl ester A mixture of 2-hydroxy-4'-(methylsulfonyl) isobutryophenone (100 g), 3-fluorophenylacetic acid (83 g), 1-cyclohexyl-3-(2-morpholinoethyl)carbodiimide metho-p-toluenesulfonate (225 g) and DMAP (25 g) in $CH_2Cl_2$ (2 L) was mechanically stirred for 17 h at r.t. A solution of 1 M HCl (1 L) was then added and the organic phase was separated, washed with a saturated solution of $Na_2CO_3$ (0.4 L) and dried over $MgSO_4$. After concentration, the residue was purified by silica gel chromatography, eluting with 30% EtOAc/hexanes to give the title compound as a white solid (133 g).

Step 3 5,5-Dimethyl-3-(3-fluorophenyl)-4-(4-(methylsulfonyl)phenyl)-2-(5H)-furanone A solution of the product from Step 2 (120 g) in $CH_2Cl_2$ (1 L) was treated with DBU (81.6 g) and stirred for 1 h at r.t. The reaction mixture was then treated with 1 M HCl (550 mL) and the organic phase was separated, washed with saturated $NaHCO_3$ and dried over $MgSO_4$. After concentration, the crude was swished from 20% EtOAc/ hexanes (450 mL) to give the title compound as a white solid (108.4 g, m.p. 172.7° C.).

Step 4 5,5-Dimethyl-3-(3-fluorophenyl)-2-hydroxy-4-(4-(methylsulfonyl)phenyl)-2,5-dihydrofuran To a −50° C. solution of 5,5-dimethyl-3-(3-fluorophenyl)-4-(4-(methylsulfonyl)phenyl)-2-(5H)-furanone (30 g, 83.3 mmol) in 500 mL of THF was added dropwise a solution of DIBAL (90 mL, 1.5 M in toluene) over a period of 15 min. The reaction mixture was allowed to warm to −10° C. over a period of 1 h, then treated with 20 mL of acetone, followed by 50 mL of methanol. The reaction mixture was then warmed to −20° C. and treated with aqueous potassium sodium tartrate (20%, 400 mL). After stirring at r.t. for 1 h, the product was extracted with 500 mL of 2:1 EtOAc/ hexane, dried over $Na_2SO_4$, filtered and concentrated. The crude product was swished with 2:1 hexane/EtOAc to give 24 g of purified title compound as a white solid.

$^1$H NMR ($CD_3COCD_3$) δ 8.00 (2H, d), 7.55 (2H, d), 7.20 (1H, m), 7.04 (1H, m), 7.02 (1H, s), 6.93 (1H, m), 6.29 (1H, d), 5.60 (1H, d), 3.15 (3H, s), 1.48 (3H, s), 1.36 (3H, s).

The following examples were prepared according to the indicated method in each case.

EXAMPLE 2

3-(3,5-Difluorophenyl)-5,5-dimethyl-2-hydroxy-4-(4-(methylsulfonyl)phenyl)-2,5-dihydrofuran (Method A)

$^1$H NMR ($CD_3COCD_3$) δ 8.01 (2H, d), 7.56 (2H, d), 6.9–6.8 (3H, m), 6.29 (1H, d), 5.67 (1H, d), 3.15 (3H, s), 1.47 (3H, s), 1.37 (3H, s).

EXAMPLE 3

5,5-Dimethyl-3-(4-fluorophenyl)-2-hydroxy-4-(4-(methylsulfonyl)phenyl)-2,5-dihydrofuran (Method A)

$^1$H NMR ($CD_3COCD_3$) δ 7.78 (2H, d), 7.44 (2H, m), 7.18 (2H, m), 6.89 (2H, m), 6.35 (1H, s), 3.11 (3H, s), 1.42 (3H, s), 1.36 (3H, s).

EXAMPLE 4

5,5-Dimethyl-3-(4-fluorophenyl)-2-methoxy-4-(4-(methylsulfonyl)phenyl)-2,5-dihydrofuran (Method B)

$^1$H NMR ($CD_3COCD_3$) δ 7.78 (2H, m), 7.52 (2H, m), 7.22 (2H, m), 6.95 (2H, m), 6.00 (1H, s), 3.45 (3H, s), 3.14 (3H, s), 1.46 (3H, s), 1.35 (3H, s).

EXAMPLE 5

5,5-Dimethyl-2-ethoxy-3-(3-fluorophenyl)-4-(4-(methylsulfonyl)phenyl)-2,5-dihydrofuran (Method B)

To a solution of 5,5-dimethyl-2-hydroxy-3-(3-fluorophenyl)-4-(4-(methylsulfonyl)phenyl)-2,5-dihydrofuran (Example 1, 500 mg, 1.38 mmol) in 5 mL of EtOH was added 3 drops of $BF_3.OEt_2$. The mixture was stirred at room temperature for 45 min, and the resulting precipitate was filtered and washed with EtOH to provide 497 mg of the title compound as a white solid.

$^1$H NMR ($CD_3COCD_3$) δ 8.00 (2H, m), 7.55 (2H, m), 7.20 (1H, m), 6.98 (3H, m), 6.10 (1H, s), 3.85 (1H, m), 3.70 (1H, m), 3.15 (3H, s), 1.50 (3H, s), 1.35 (3H, s), 1.20 (3H, t).

EXAMPLE 6

5,5-Dimethyl-3-(3-fluorophenyl)-2-isopropoxy-4-(4-(methylsulfonyl)phenyl)-2,5-dihydrofuran (Method B)

$^1$H NMR ($CD_3COCD_3$) δ 7.95 (2H, m), 7.50 (2H, m), 7.18 (1H, m), 6.93 (3H, m), 6.15 (1H, s), 4.13 (1H, m), 3.15 (3H, s), 1.50 (3H, s), 1.35 (3H, s), 1.25 (3H, d), 1.20 (3H, d).

EXAMPLE 7

5,5-Dimethyl-3-(3-fluorophenyl)-4-(4-(methylsulfonyl)phenyl)-2-methylthio-2,5-dihydrofuran (Method B)

$^1$H NMR ($CD_3COCD_3$) δ 7.95 (2H, d), 7.52 (2H, d), 7.21 (1H, d), 6.95 (3H, m), 6.53 (1H, s), 3.13 (3H, s), 2.12 (3H, s), 1.61 (3H, s).

EXAMPLE 8

5-Ethyl-3-(4-fluorophenyl)-2-hydroxy-5-methyl-4-(4-(methylsulfonyl)phenyl)-2,5-dihydrofuran (Method A)

$^1$H NMR ($CD_3COCD_3$) δ 7.98 (2H, d), 7.53 (2H, d), 7.17 (1H, m), 7.02 (2H, m), 6.94 (1H, m), 6.36 (1H, d), 5.67 (1H, d), 3.14 (3H, s), 1.72 (1H, m), 1.60 (1H, m), 1.35 (3H, s), 1.04 (3H, t).

EXAMPLE 9

5,5-Dimethyl-3-(3-fluorophenoxy)-2-hydroxy-4-(4-(methylsulfonyl)phenyl)-2,5-dihydrofuran (Method E)

Analysis: Calc. for $C_{19}H_{19}FO_5S$: C, 60.31; H, 5.06; S, 8.47. Found: C, 60.24; H, 5.16; S, 8.34.

EXAMPLE 10

5,5-Dimethyl-3-(3,4-difluorophenoxy)-2-hydroxy-4-(4-(methylsulfonyl)phenyl)-2,5-dihydrofuran (Method E)

Step 1 3-(3,4-Difluorophenoxy)-5,5-dimethyl-4-(4-(methylsulfonyl)phenyl)-5H-furan-2-one A solution of 3,4-difluorophenoxyacetic acid (0.51 g, 2.73 mmol), 2-hydroxy-4'-(methylsulfonyl)isobutyrophenone (Ex. 1, Step 1, 0.5 g, 2.1 mmol), CMC (1.13 g, 2.73 mmol) and DMAP (15 mg, 0.10 mmol) in dichloromethane (12 mL) was stirred at r.t. for 18 hrs. DBU (0.63 ml, 4.2 mmol) was then added and the reaction mixture was heated to reflux for 3 hrs. After cooling to r.t., the mixture was extracted with ethyl acetate and washed successively with water, 1N HCl and brine. The organic layer was dried over $MgSO_4$, filtered and concentrated. The residue was triturated with a mixture of ethyl acetate and hexane to afford the title compound as a solid. m.p.: 93–95° C.

$^1$H NMR ($CD_3COCD_3$) δ 1.77 (6H, s), 3.15 (3H, s), 6.93–6.97 (1H, m), 7.12–7.29 (2H, m), 7.92 (2h, d), 8.04 (2H, d).

Analysis calculated for $C_{19}H_{16}F_2O_5S$: C, 57.86; H, 4.09. Found: C, 57.77; H, 4.28

Step 2 5,5-Dimethyl-3-(3,4-difluorophenoxy)-2-hydroxy-4-(4-(methylsulfonyl)phenyl)-2,5-dihydrofuran To a 0° C. solution of 3-(3,4-difluorophenoxy)-5,5-dimethyl-4-(4-(methylsulfonyl)phenyl)-5H-furan-2-one (500 mg, 1.27 mmol) in 10 mL of THF was added DIBAL (1.5M in toluene, 2.8 mL, 4.2 mmol). Warmed to r.t., and stirred 30 min. The reaction was quenched with acetone, followed by 0.5M sodium potassium tartrate and stirred overnight. The mixture was extracted with EtOAc, washed with brine, dried over $MgSO_4$, filtered and concentrated. Crystalization from $CH_2Cl_2$/toluene provided 350 mg of the title compound.

$^1$H NMR ($CD_3COCD_3$) δ 7.91 (2H, d), 7.68 (2H, d), 7.07–7.12 (2H, m), 6.92–6.97 (1H, m), 5.90 (1H, d), 5.69 (1H, d), 3.09 (3H, s), 1.59 (3H, s), 1.46 (3H, s). m.p. 151° C. Analysis: Calc. for $C_{19}H_{18}F_2O_5S$: C, 57.57; H, 4.58. Found: C, 57.42; H, 4.67.

EXAMPLE 11

3-(3,4-Difluorophenyl)-2-hydroxy-4-(4-(methylsulfonyl)phenyl)-2,5-dihydrofuran (Method A)

EXAMPLE 12

2-(4-Fluorophenyl)-3-(4-(methylsulfonyl)phenyl)-2-cyclopenten-1-ol (Method A)

$^1$H NMR ($CD_3COCD_3$) δ 7.75 (2H, d), 7.32 (2H, d), 7.24–7.16 (2H, m), 6.99–6.95 (2H, m), 5.18 (1H, br s), 3.12–3.00 (1H, m), 3.02 (3H, s), 2.74 (1H, m), 2.51 (1H, m), 2.00 (1H, m).

EXAMPLE 13

3-(4-Methylsulfonyl)phenyl)-2-phenyl-2-cyclopenten-1-ol (Method A)

$^1$H NMR ($CD_3COCD_3$) δ 7.76 (2H, d), 7.42 (2H, d), 7.28–7.20 (5H, m), 5.13 (1H, m), 4.08 (1H, d), 3.08 (3H, s), 3.05 (1H, m), 2.78 (1H, m), 2.44 (1H, m), 1.95 (1H, m).

EXAMPLE 14

2-Acetoxy-5,5-dimethyl-3-(3-fluorophenyl)-4-(4-(methylsulfonyl)phenyl)-2,5-dihydrofuran (Method D)

To a solution of 5,5-Dimethyl-3-(3-fluorophenyl)-2-hydroxy-4-(4-methylsulfonylphenyl)-2,5-dihydrofuran (Example 1, 0.8 g) and triethylamine (2 mL) in dichloromethane (20 mL) was added DMAP (5 mg) and acetic anhydride (1 mL). The resulting mixture was stirred at room temperature for 10 min, then quenched with $CH_2Cl_2$ and the aqueous $NaHCO_3$. The mixture was extracted with $CH_2Cl_2$ and the organic phase was dried over $Na_2SO_4$, filtered and evaporated. The resulting solid was swished in 1:1 EtOAc/hexanes to provide 0.5 g of the title compound as a white solid.

¹H NMR (CD₃COCD₃) δ 8.03 (2H, d), 7.60 (2H, d), 7.27 (1H, s), 7.25 (1H, m), 7.00 (2H, m), 6.37 (1H, m), 3.16 (3H, s), 2.03 (3H, s), 1.55 (3H, s), 1.35 (3H, s).

EXAMPLE 17

2-(3,5-Difluorophenyl)-3-(4-(methylsulfonyl)phenyl)-2-cyclopenten-1-ol (Method A)

Step 1 3-(4-(Methylthiol)phenyl)-2-cyclopenten-1-one

To a −65° C. solution of 4-bromothioanisole (61 g, 0.3 mol) in THF (800 mL) was added a solution of n-BuLi (2.3M in hexanes, 120 mL) at a rate so as to maintain an internal temperature below −55° C. The resulting slush was stirred at −65° C. for 2 h, then treated with a solution of 3-ethoxy-2-cyclopenten-1-one (35 g, 0.28 mmol) in THF (50 mL). After 30 min at −65° C., the solution was warmed to 0° C. and quenched with sat. aq. NH₄Cl (400 mL). The product was extracted with 3×1 L of EtOAc and the combined extracts were dried over MgSO₄ and concentrated. The resulting material was swished in 200 mL of 1:1 EtOAc/hexanes to provide 45 g of the title compound as a white solid.

Step 2 2-Bromo-3-(4-(methylthiol)phenyl)-2-cyclopenten-1-one

To a suspension of 3-(4-(methylthiol)phenyl)-2-cyclopenten-1-one (9.64 g, 47.2 mmol) in CCl₄ (200 mL) was added a solution of bromine (5 mL) in CCl₄ (30 mL) over 20 min. The resulting orange suspension was stirred for 1.5 h, then cooled in an ice-bath, and triethylamine (14 mL, 100 mmol) was added. After 30 min, the mixture was quenched with 1M HCl (300 mL) and extracted with CH₂Cl₂. The organic phase was washed with brine, filtered through cotton and evaporated. Purification by silica gel chromatography, eluting with 90% CH₂Cl₂/hexanes gave the title compound (7.13 g).

Step 3 2-Bromo-3-(4-(methylsulfonyl)phenyl)-2-cyclopenten-1-one

To a 0° C. solution of 2-bromo-3-(4-(methylthiol)phenyl)-2-cyclopenten-1-one (5.73 g, 20.2 mmol) in CH₂Cl₂ (100 mL) and MeOH (50 mL) was added MMPP (19 g, 30.7 mmol). The mixture was stirred 5 h at r.t., then concentrated. The residue was partitioned between sat. aq. NaHCO₃ and CH₂Cl₂. The organic phase was washed with brine, filtered through cotton and evaporated. The resulting solid was swished in CH₂Cl₂/hexanes to provide the title compound (5.57 g).

Step 4 2-(3,5-Difluorophenyl)-3-(4-(methylsulfonyl)phenyl)-2-cyclopenten-1-one

To a mixture of 2-bromo-3-(4-methylsulfonyl)phenyl)-2-cyclopenten-1-one (664 mg, 2.11 mmol), 3,5-difluorophenylboronic acid (832 mg, 5.27 mmol), tris(dibenzylideneacetone)dipalladium(O) (83 mg, 0.09 mmol), and triphenylphosphine (96 mg, 0.36 mmol) was added 40 mL of 3:1:1 toluene:n-propanol:water and the mixture was purged with nitrogen. After stirring 10 min, diethylamine (1.1 mL, 10.6 mmol) was added and the solution was heated to reflux for 4 h. The mixture was cooled and partitioned between 1M NaOH and EtOAc. The organic phase was washed with water, 1M HCl and brine, and dried over MgSO₄. Purification by silica gel chromatography, eluting with 50% CH₂Cl₂/hexanes, followed by crystallization from CH₂Cl₂/ether/hexanes gave the title compound (223 mg).

¹N NMR (CD₃COCD₃) δ 7.95 (2H, d), 7.65 (2H, d), 6.98 (1H, m), 6.82 (2H, m), 3.19 (2H, m), 3.15 (3H, s), 2.68 (2H, m).

Step 5 2-(3,5-Difluorophenyl)-3-(4-(methylsulfonyl)phenyl)-2-cyclopenten-1-ol

To a −78° C. solution of 2-(3,5-Difluorophenyl)-3-(4-(methylsulfonyl)phenyl)-2-cyclopenten-1-one (98 mg, 0.28 mmol) in THF (5 mL) was added DIBAL (1.5M toluene solution, 0.4 mL, 0.6 mmol). The solution was warmed to 0° C. and stirred 15 min, then cooled to −78° C. and quenched with 0.5 mL acetone. The solution was warmed and poured into 1M sodium potassium tartrate. The mixture was extracted with EtOAc, washed with brine, and dried over MgSO₄. Crystallization from ether/hexanes provided the title compound (90 mg).

¹H NMR (CD₃COCD₃) δ 7.85 (2H, d), 7.45 (2H, d), 6.85 (3H, m), 5.13 (1H, m), 4.33 (d, 1H), 3.10 (3H, s), 3.02 (1H, m), 2.83 (1H, m), 2.48 (1H, m), 1.95 (1H, m).

EXAMPLE 20

Sodium (5,5-dimethyl-3-(3-fluorophenyl)-4-(4-(methylsulfonyl)phenyl)-2,5-dihydrofuran-2-yloxy)acetetate (Method B)

¹H NMR (DMSO-d₆) δ 8.01 (2H, m), 7.60 (1H, m), 7.53 (2H, m), 7.12 (2H, m), 7.00 (1H, m), 6.35 (1H, s), 3.98 (1H, d), 3.75 (1H, d), 3.29 (3H, s), 1.38 (3H, s), 1.28 (3H, s).

EXAMPLE 21

Succinic Acid mono-(3-(4-(methylsulfonyl)phenyl)-2-phenyl-cyclopent-2-enyl) Ester (Method D)

¹H NMR (CD₃COCD₃) δ 7.80 (2H, m), 7.46 (2H, m), 7.26 (3H, m), 7.19 (2H, m), 6.17 (1H, m), 3.15 (1H, m), 3.10 (3H, s), 2.86 (1H, m), 1.38 (3H, s), 2.5 (5H, m), 2.0 (1H, m).

EXAMPLE 39

3-Isopropoxy-5,5-dimethyl-4-(4-methylsulfonylphenyl)-2,5-dihydrofuran-2-ol (Method A)

¹H NMR (CD₃COCD₃, 300 MHz) δ 7.90 (2H, m), 7.83 (2H, m), 5.96 (1H, d), 5.53 (1H, d), 4.66 (1H, m), 3.12 (3H, s), 1.55 (3H, s), 1.42 (3H, s), 1.25 (6H, m). Analysis: Calc. for C₁₆H₂₂O₅S: C, 58.88; H, 6.79 Found: C, 58.69; H, 6.69.

EXAMPLE 40

3-(4-Methylsulfonylphenyl)-2-(3-pyridinyl)-2-cyclopenten-1-ol (Method A)

¹H NMR (CD₃COCD₃, 300 MHz) δ 8.46 (1H, m), 8.40 (1H, m), 7.28 (2H, m), 7.59 (1H, m), 7.32 (2H, m), 7.22 (1H, m), 5.22 (1H, m), 3.10 (1H, m), 3.02 (3H, s), 2.80 (1H, m), 2.56 (1H, m), 2.03 (1H, m).

EXAMPLE 41

5,5-Dimethyl-4-(4-methylsulfonylphenyl)-3-phenyl-2,5-dihydrofuran-2-ol (Method A)

Analysis: Calc. for C₁₉H₂₀O₄S: C, 66.26; H, 5.85 Found: C, 66.19; H, 6.02.

EXAMPLE 42

3-(3-Fluorophenyl)-5,5-dimethyl-4-(4-methylsulfinylphenyl)-2,5-dihydro-furan-2-ol (Method A)

¹H NMR (CD₃COCD₃, 400 MHz) δ 7.23 (2H, d), 6.95 (2H, d), 7.19 (1H, m), 7.04 (2H, m), 6.90 (1H, m), 6.28 (0.5H, d), 6.26 (1H, s), 5.54 (0.5H, d), 2.72 (3H, s), 1.46 (3H, s), 1.32 (3H, s).

EXAMPLE 43

3-(3,4-Difluorophenyl)-5,5-dimethyl-4-(4-methylsulfonylphenyl)-2,5-dihydrofuran-2-ol (Method A)

¹H NMR (CD₃COCD₃, 300 MHz) δ 8.00 (2H, m), 7.55 (2H, m), 7.21 (1H, m), 7.12 (1H, m), 7.03 (1H, m), 6.28 (1H, d), 5.16 (1H, d), 3.15 (3H, s), 1.49 (3H, s), 1.38 (3H, s).

EXAMPLE 44

3-(1-Cyclopropylethoxy)-5,5-dimethyl-4-(4-methylsulfonylphenyl)-2,5-dihydrofuran-2-ol (Method A)

$^1$H NMR (CD$_3$COCD$_3$, 300 MHz) δ 7.90 (4H, m), 5.95 (1H, dd), 5.50 (1H, dd), 4.00 (1H, m), 3.10 (3H, s), 1.55 (3H, s), 1.40 (3H, s), 1.30 (3H, d), 0.3–1.10 (5H, m).

EXAMPLE 45

3-Cyclopropylmethoxy)-5,5-dimethyl-4-(4-methylsulfonylphenyl)-2,5-dihydrofuran-2-ol (Method A)

Analysis: Calc. for C$_{17}$H$_{22}$O$_5$S: C, 60.34; H, 6.55 Found: C, 60.81; H, 6.48. MS: 321 (M$^+$-OH).

EXAMPLE 46

3-(3,4-Difluorophenoxy)-5-methyl-4-(4-methylsulfonylphenyl)-5-(2,2,2-trifluoroethyl)-2,5-dihydrofuran-2-ol (Method A)

$^1$H NMR (CD$_3$COCD$_3$, 400 MHz) δ 7.95–7.70 (4H, m), 7.35–6.90 (3H, m), 5.95 (1H, m), 3.10 (3H, 2s), 2.95–2.65 (4H, m), 1.75 and 1.68 (3H, 2s). MS (FAB): 464 (M$^+$), 447 (M$^+$-OH).

EXAMPLE 47

4-[3-(4-Methylsulfonylphenyl)-2-phenyl-cyclopent-2-enyloxycarbonylamido]benzoic Acid, Ethyl Ester (Methods A+F)

To a solution of ethyl 4-isocyanatobenzoate (0.47 g) and pyridine (0.5 mL) in 15 mL of toluene was added a solution of 3-(4-(methylsulfonyl)phenyl)-2-phenyl-2-cyclopenten-1-ol (0.40 g) in 4 mL of toluene. After stirring for a period of 1.5 h at room temperature, ethanol (1 Ml) was added and the reaction mixture was diluted with EtOAc (50 mL). After washing with 1M CuSO$_4$ (2×20 mL), the organic layer was dried over MgSO$_4$ and concentrated. The residue was purified by silica gel chromatography eluted with 30% EtOAc in hexane and the product was then crystalized in 50 mL of 1:1 EtOAc/hexane to give the title compound as a white solid (0.11 g).

$^1$H NMR (CD$_3$COCD$_3$, 400 MHz) δ 9.00 (1H, bs), 7.93 (2H, d), 7.82 (2H, d), 7.65 (2H, d), 7.48 (2H, d), 7.2–7.3 (5H, m), 6.24 (1H, m), 4.30 (2H, q), 3.21 (1H, m), 3.10 (3H, s), 2.87 (1H, ddd), 2.62 (1H, m), 2.11 (1H, m), 1.33 (3H, t).

EXAMPLE 48

4-[3-(4-Methylsulfonylphenyl)-2-phenyl-cyclopent-2-enyloxycarbonylamido]benzoic Acid (Methods A+F)

To a solution of 4-[3-(4-methylsulfonylphenyl)-2-phenyl-cyclopent-2-enyloxycarbonylamido]benzoic acid, ethyl ester (0.41 g) in 11 mL of THF were added 1M LiOH (1.85 mL) and water (2 mL). After stirring for 8 days, the reaction was treated with NH$_4$OAc buffer solution (25% w/v) and extracted with EtOAc (50 mL). The organic layer was dried over MgSO$_4$ and concentrated. The crude product was swished in 20 mL of EtOAc to give the title compound as a white solid.

$^1$H NMR (CD$_3$COCD$_3$, 400 MHz) δ 10.95 (1H, bs), 9.00 (1H, bs), 7.97 (2H, d), 7.81 (1H, d), 7.64 (2H, d), 7.48 (2H, d), 7.25 (5H, m), 6.26 (1H, m), 3.20 (1H, m), 3.13 (3H, s), 2.90 (1H, ddd), 2.63 (1H, m), 2.05–2.18 (1H, m).

The following section provides example for the preparation of starting materials for the preparation of compounds within the scope of the invention. As appreciated by those of skill in the art, the following section is a self-contained unit. Thus, while the section may contain Example numbers and other designations which duplicate those used for the compounds of the instant invention, such duplication is not to be regarded as an assertion that the Examples and designations are identical.

Starting materials for the preparation of compounds of the present invention can be prepared according to the following methods.

Method A

An appropriately substituted acid halide is reacted with thioanisole in a solvent such as chloroform in the presence of a Lewis acid such as aluminum chloride to afford a ketone which is then hydroxylated with base such as aqueous sodium hydroxide in a solvent such as carbon tetrachloride with a phase transfer agent such as Aliquat 336. Then treatment with an oxidizing agent such as MMPP in solvents such as CH$_2$Cl$_2$/MeOH, affords an sulfone which is reacted with an appropriately substituted acetic acid in a solvent such as CH$_2$Cl$_2$ in the presence of an esterifying agent such as CMC and DMAP and then treated with DBU to afford lactone Ia.

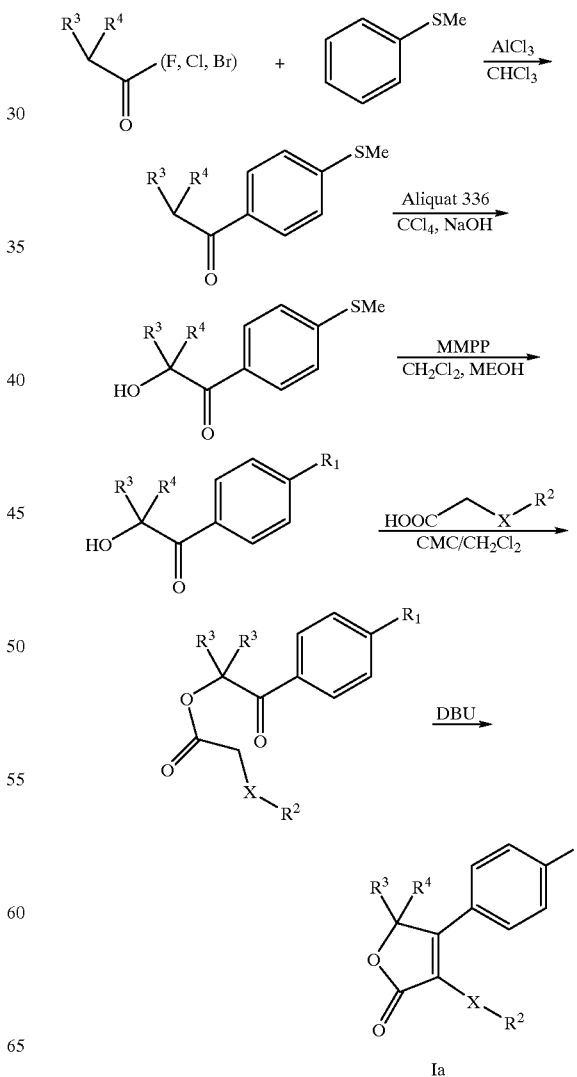

Method B

An appropriately substituted hydroxylketone is acylated withn appropriately substituted acid halide in a solvent such as dichloromethane in the presence of a base such as pyridine. The ester obtained in then reacted with an appropriately substituted nucleophile $R^2XH$ in a solvent such as DMF and with a base such as sodium hydride, then treatment with DBU in a solvent such as acetonitrile affords lactone Ia.

$R^1 = SO_2Me$

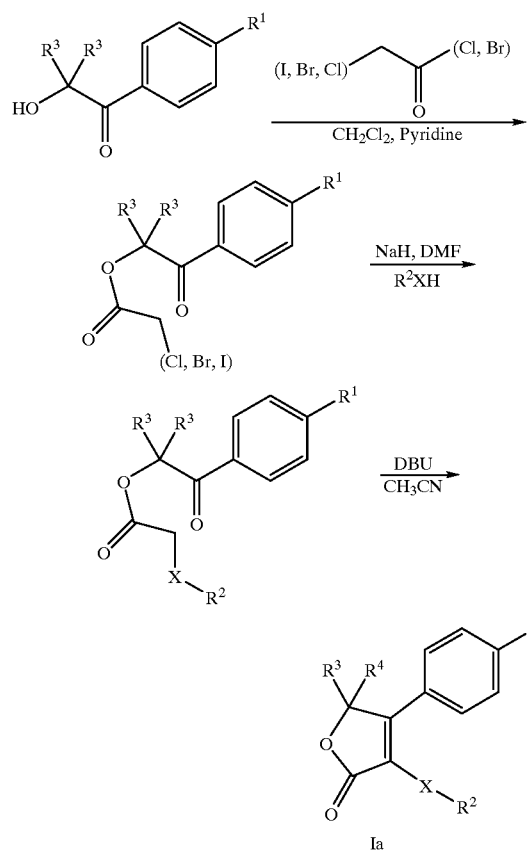

$R^1 = SO_2Me$
$X = O, S, NR^{15}$

Method C

A halo ester of acetic acid is coupled with an appropriately substituted nucleophile in water with sodium hydroxide to give an appropriately substituted acetic acid which is then reacted as in method A to afford lactone Ia.

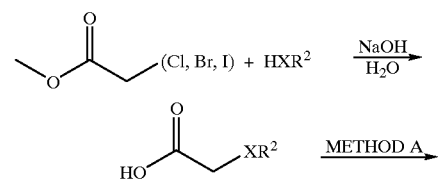

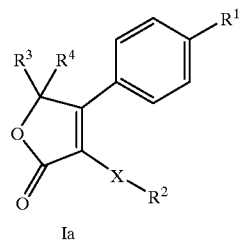

$R^1 = SO_2Me$
$X = O, S, NR^{15}$

Method D

A halo ester is reacted with an appropriately substituted amine $R^2R^{15}NH$ in a solvent such as toluene to give an intermediate which is then reacted with DBU in a solvent such as acetonitrile to afford lactone Ia.

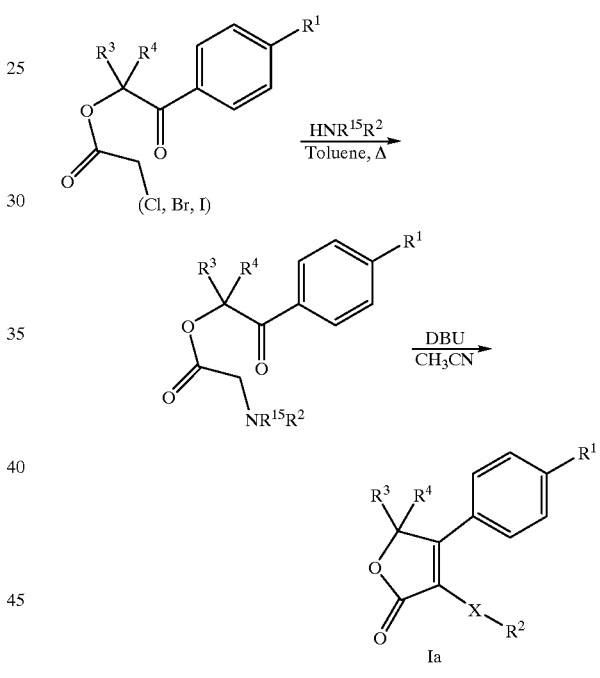

$X = NR^{15}$

Method E

An appropriately substituted bromoketone is reacted with an appropriately substituted acid in a solvent such as ethanol or acetonitrile in the presence of a base such as diisopropylethylamine or triethylamine to afford an ester which is then treated with DBU in a solvent such as acetonitrile to afford lactone Ia.

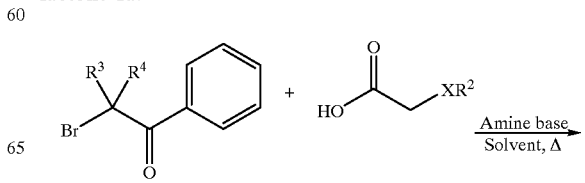

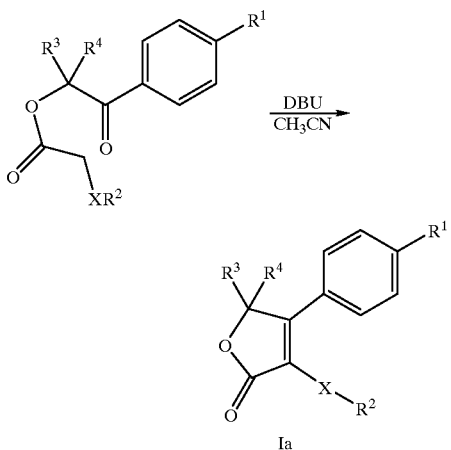

Method F

An appropriately substituted hydroxyketone is reacted with an appropriately substituted acid halide in a solvent such as dichloromethane and with a base such as pyridine to afford an ester which is then cyclized using sodium hydride in a mixture of THF and DMF to afford a lactone. The lactone is then oxidized with an oxidizing agent such as MMPP, mCPBA or OXONE® in solvents such as dichloromethane and/or methanol to afford lactone Ia.

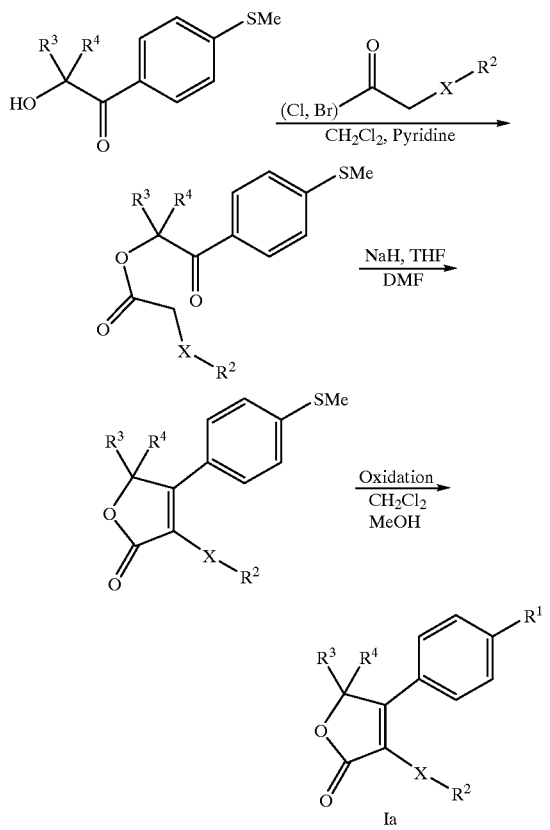

Method G

An appropriately substituted hydroxyketone is acylated with acetyl bromide or chloride in a solvent such as dichloromethane with a base such as DBU and DMAP. Further treatment with a base such as sodium hydride in a solvent such as DMF effects cyclization to afford the 5-membered lactone. Treatment of this lactone with a base such as LDA and an appropriately substituted acid halide in a solvent such as THF, followed by oxidation with a reagent such as MMPP in solvent such as $CH_2Cl_2$/MeOH nd hydrolysis by a base such as NaOH in a solvent such as MeOH/THF gives an alcohol Ib which is then oxidized to lactone Ic by a reagent such as Jone's reagent in a solvent such as acetone (the initially formed ketone is reduced in the reaction and acylated, thus requiring hydrolysis and re-oxidation to obtain ketone Ic). Alternatively, alcohol Ib can be obtained by using an aldehyde $R^2CHO$ as the electrophile instead of an acid halide.

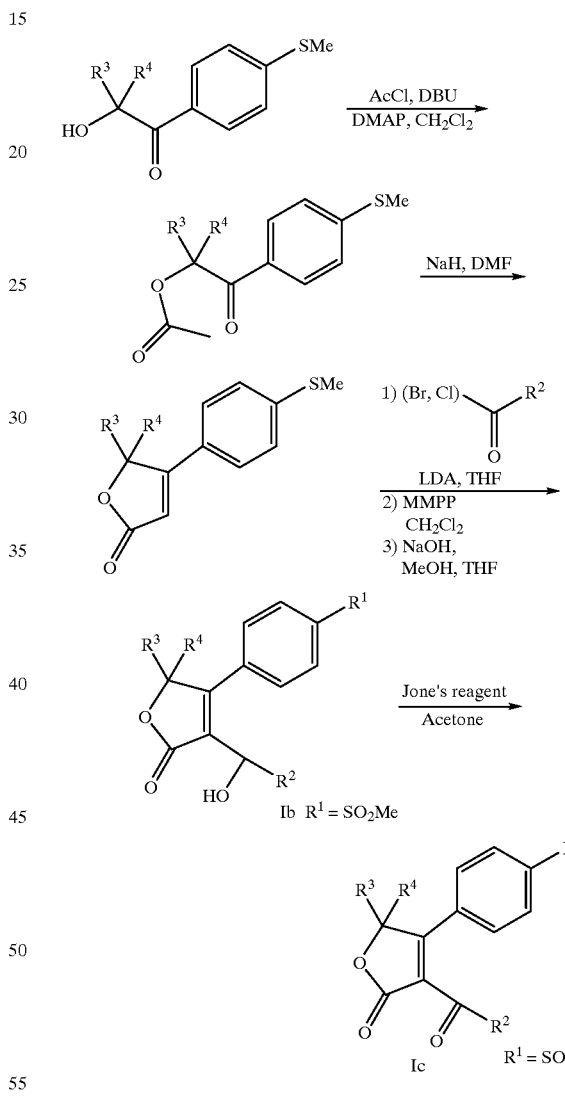

Method H

An appropriately substituted methyl sulfide is oxidized to the sulfoxide with a reagent such as MMPP in solvents such as dichloromethane and methanol followed by treatment with trifluoroacetic anhydride, then aqueous sodium hydroxide. Further treatment by $Cl_2$ in aqueous acetic acid followed by treatment by an amine affords an intermediate sulfonamide. This sulfonamide is then esterified with an appropriately substituted acid in the presence of a reagent such as CMC and further treatment with a base such as DBU affords the lactone. In the case where the amine group is protected by an acid labile group treatment with an acid such as trifluoroacetic acid in a solvent such as dichloromethane affords compound Ia.

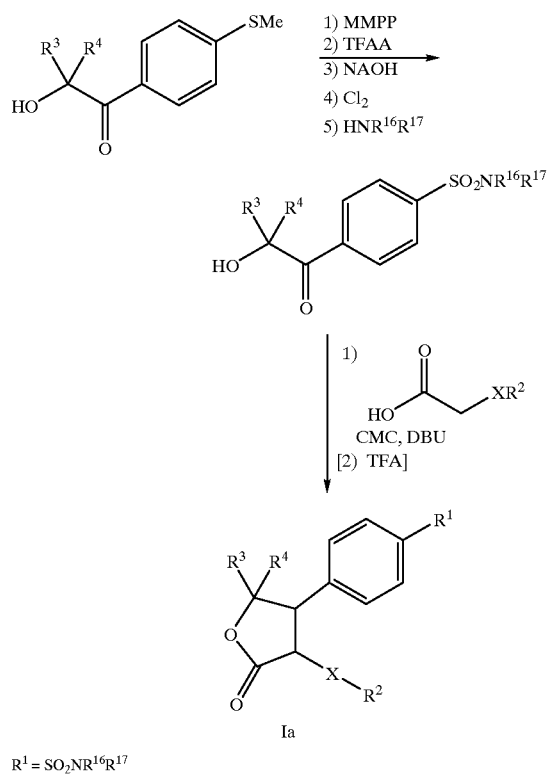

Method I

An appropriately substituted bromoketone is reacted with an appropriately substituted acid in a solvent such as acetonitrile and with a base such as Et₃N. Treatment with DBU and then O₂ gives a hydroxy compound Id. Etherification of this hydroxy with an alcohol in a solvent such as THF and with an acid such HCl gives Ie. By oxidation of the sulfide into a sulfone by a reagent such as m-CPBA and then displacement of this sulfone by an appropriately substituted nucleophile compound If is obtained.

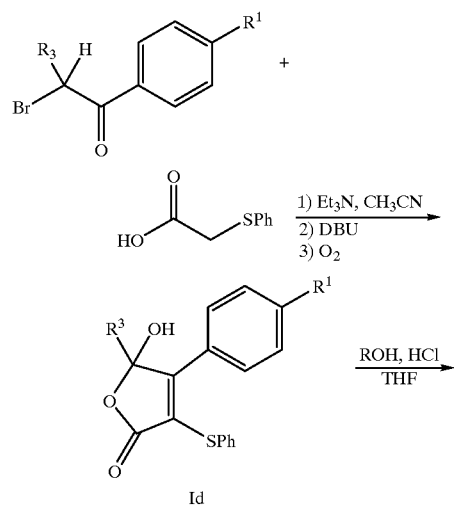

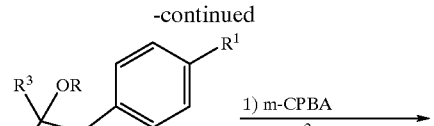

$R = C_{1-6}alkyl$
$X = O, S, NR^{15}$

Method J

An appropriately substituted nucleophile is reacted with an appropriately substituted haloacetate in a solvent such as acetonitrile with a base such as DBU to afford compound Ia.

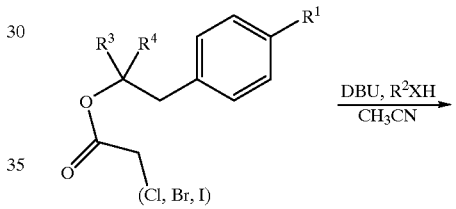

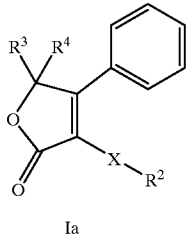

$X = O, S, NR^{15}$

Method K

An appropriately substituted vinyl ketone is coupled with an appropriately substituted benzaldehyde with a catalyst such as 3-benzyl-5-(2-hydroxyethyl)-4-methylthiazolium chloride in the presence of a base such as triethylamine in a solvent such as 1,4-dioxane to form a diketone. The diketone is cyclized in a solvent such as methanol with a base such as DBU to the final product Ig. When $R^1=SO_2Me$, the starting material can also be a p-methylthiobenzaldehyde, with the methylthio group being oxidized to $SO_2Me$ using MMPP, mCPBA or OXONE® in the last step.

-continued

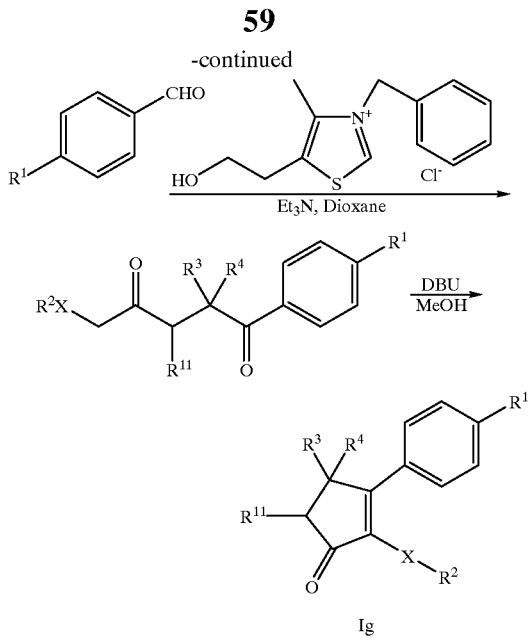

EXAMPLE 1

3-(3,4-Difluorophenoxy)-5,5-dimethyl-4-(4-methylsulfonyl)phenyl)-5H-furan-2-one

Step 1: 2-Methyl-1-(4-(methylthio)phenyl)-propan-1-one

To a suspension of aluminum chloride (136 g, 1.02 mol) in chloroform (1.0 L) cooled to −10° C., was added dropwise isobutyrylchoride (115 mL, 1.10 mol). Then thioanisole (100 mL, 0.85 mol) was added dropwise. Upon completion of addition the reaction was allowed to proceed at r.t. for 1.5 h. The reaction was cooled to 10° C. and quenched by addition of water (750 mL). The organic layer was separated, washed with water (2×500 mL), saturated NaHCO$_3$ solution (2×500 mL), brine (1×500 mL), and then dried over Na$_2$SO$_4$. After concentration in vacuo., the resulting crude product crystallized upon standing under high vacuum for 30 min to give the title compound as a brown solid.

Step 2: 2-Hydroxy-2-methyl-1-(4-(methylthio)phenyl)propan-1-one

To a solution of 2-methyl-1-(4-(methylthio)phenyl) propan-1-one (28.5 g, 147 mmol, Step 1), Aliquat 336 (11.0 mL, 24 mmol) and carbon tetrachloride (21 mL, 218 mmol) in toluene (43 mL) was added sodium hydroxide (12.9 g, pellets, 322 mmol). The reaction was stirred at 15° C. for 2 h and then at r.t. for 16 h. The reaction was diluted with water (100 mL), brine (100 mL) and EtOAc (300 mL). The aqueous phase was acidified with 1N HCl and extracted with EtOAc (100 mL). The combined organic layers were dried over Na$_2$SO$_4$ and concentrated. The crude product was purified by silica gel chromatography eluted with 15% EtOAc in hexane to give the title compound as a thick syrup.

Step 3: 2-Hydroxy-2-methyl-1-(4-(methylsulfonyl)phenyl)propan-1-one

To a cold (4° C.) solution of 2-hydroxy-2-methyl-1-(4-(methylthio)phenyl)propan-1-one (45.0 g, 214 mmol, Step 2) in t-butanol (500 mL) and CH$_2$Cl$_2$ (500 mL) was added a solution of OXONE™ (194 g, 316 mmol) in water (1.4 L). The resulting suspension was stirred at r.t. for 18 h. The reaction was diluted with EtOAc (400 mL) and the layers were separated. The aqueous layer was extracted with EtOAc (2×250 mL). The combined organic layers were dried over Na$_2$SO$_4$ and concentrated in vacuo. The crude product was dissolved in diethyl ether (250 mL), hexane was added (150 mL) and the product was swished for 2 h. The product was collected by filtration to give the title compound as a yellow solid.

Step 4  3-(3,4-Difluorophenoxy)-5,5-dimethyl-4-(4-(methylsulfonyl)phenyl)-5H-furan-2-one A solution of 3,4-difluorophenoxyacetic acid (0.51 g, 2.73 mmol), 2-hydroxy-2-methyl-1-(4-(methylsulfonyl)phenyl) propan-1-one (0.5 g, 2.1 mmol, Step 3), CMC (1.13 g, 2.73 mmol) and DMAP (15 mg, 0.10 mmol) in dichloromethane (12 ml) was stirred at r.t. for 18 hrs. Then, DBU (0.63 ml, 4.2 mmol) was added and the reaction mixture was refluxed for 3 h. After cooling to r.t. the mixture was extracted with ethyl acetate and washed successively with water, 1N HCl and brine. The organic layer was dried over MgSO$_4$, filtered and the solvent evaporated under vacuum. The residue was triturated in a mixture of ethyl acetate and hexane affording the title compound as a solid. M.P.: 93–95° C.

$^1$H NMR (CD$_3$COCD$_3$) δ 1.77 (6H, s), 3.15 (3H, s), 6.93–6.97 (1H, m), 7.12–7.29 (2H, m), 7.92 (2H, d), 8.04 (2H, d).

Analysis calculated for C$_{19}$H$_{16}$F$_2$O$_5$S: C, 57.86; H, 4.09; Found: C, 57.77; H, 4.28

EXAMPLE 2

3-(3-Fluorophenoxy)-5,5-dimethyl-4-(4-(methylsulfonyl)phenyl)-5H-furan-2-one

Following the procedure described for example 1, the title compound was prepared from 3-fluorophenoxyacetic acid. M.P.: 136–138° C.

$^1$H NMR (CD$_3$COCD$_3$)δ 1.79 (6H, s), 3.15 (3H, s), 6.85–6.94 (3H, M), 7.31–7.86 (1H, m), 7.93 (2H, d), 8.03 (2H, d),

EXAMPLE 3

3-(3,5-Difluorophenoxy)-5,5-dimethyl-4-(4-(methylsulfonyl)phenyl)-5H-furan-2-one Following the procedure described for example 1, the title compound was prepared from 3,5-difluorophenoxyacetic acid. M.P.: 159–161° C.

$^1$H NMR (CD$_3$COCD$_3$)δ 1.80 (6H, s), 3.17 (3H, s), 6.78–6.84 (3H, m), 7.96 (2H, d), 8.06 (2H, d).

Analysis calculated for C$_{19}$H$_{16}$F$_2$O$_5$S: C, 57.86; H, 4.09; Found: C, 57.66; H, 4.30

EXAMPLE 4

3-Phenoxy-5,5-dimethyl-4-(4-(methylsulfonyl) phenyl)-5H-furan-2-one

Step 1  3-Phenoxy-5,5-dimethyl-4-(4-(methylthio)phenyl)-5H-furan-2-one

Following the procedure described for example 1, Step 4, the title compound was prepared from phenoxyacetic acid and 2-hydroxy-2-methyl-1-(4-(methylthio)phenyl)propan-1-one (example 1, Step 4).

$^1$H NMR (CD$_3$COCD$_3$)δ 1.79 (6H, s), 2.51 (3H, s), 7.03–7.10 (3H, m), 7.30–7.37 (4H, m), 7.72 (2H, d).

Step 2  3-Phenoxy-5,5-dimethyl-4-(4-(methylsulfonyl) phenyl)-5H-furan-2-one

The compound obtained in Step 1 (150 mg, 0.46 mmol) was stirred in dichloromethane (5 mL) with 3-chloroperoxybenzoic acid (250 mg, 1.38 mmol) for 18 hrs. The reaction mixture was diluted with ethyl acetate, washed with saturated sodium bicarbonate, brine, dried over MgSO$_4$, filtered and the solvent evaporated under vacuum. The residue was triturated in Et$_2$O to afford the title compound. M.P.: 135–136° C. $^1$H NMR (CD$_3$COCD$_3$) δ 1.78

(6H, s), 3.14 (3H, s), 7.05–7.08 (3H, m), 7.28–7.30 (2H, m), 7.92 (2H, d), 8.01 (2H, d).

Analysis calculated for $C_{19}H_{18}O_5S$: C, 63.67; H, 5.06; S, 8.95;

Found: C, 64.02; H, 5.10: S, 8.84

EXAMPLE 5

3-(2,4-Difluorophenoxy)-5,5-dimethyl-4-(4-(methylsulfonyl)phenyl)-5H-furan-2-one Step 1 2-Bromoacetic Acid, 2-methyl-1-(4-(methylsulfonyl) phenyl)propan-1-one Ester To a 0° C. solution of 2-hydroxy-2-methyl-1-(4-(methylsulfonyl)phenyl)propan-1-one (4.0 g, 16.5 mmol, example 1, Step 3) in dichloromethane (100 mL) was added pyridine (23.5 mL, 291 mmol) and bromoacetyl bromide (24.9 mL, 285.3 mmol) portionwise over 2 hrs. The reaction mixture was allowed to warm to r.t. and stirred for a further hour. The mixture was diluted with dichloromethane, washed with 1N HCl, brine, filtered through cotton and the solvent was evaporated under vacuum. Purification by silica gel chromatography (40% EtOAc/Hex.) provided 3.50 g of the title compound.

$^1$H NMR ($CD_3COCD_3$) δ 1.75 (6H, s), 3.20 (3H, s), 4.00 (2H, s), 8.05 (2H, m), 8.25 (2H, m).

Step 2 2-(2,4-Difluorophenoxy)acetic Acid 2-methyl-1-(4-(methylsulfonyl)phenyl)propan-1-one-2yl Ester Sodium hydride, 60% dispersion (66 mg, 1.66 mmol), was rinsed with hexane, suspended in 7 mL of DMF and cooled to 0° C. To this suspension was added 2,4-difluorophenol (170 μL, 1.79 mmol). After 5 minutes at 0° C., 2-bromoacetic acid 2-methyl-1-(4-(methylsulfonyl)phenyl)propan-1one ester (Step 1) (233 mg, 1.79 mmol) was added and the reaction mixture was stirred for 30 minutes. Dichloromethane was added and the mixture was washed with 1N HCl and the organic solvent was evaporated under vacuum. The residue was dissolved in 25% EtOAc/$Et_2O$ and washed with 1N NaOH, water (2×) brine and dried over $MgSO_4$. After filtration and evaporation of the solvent under vacuum 470 mg of the title compound was obtained. $^1$H NMR ($CD_3COCD_3$) δ 1.75 (6H, s), 3.20 (3H, s), 4.80 (2H, s), 6.60 (1H, m), 6.75 (1H, m), 7.00 (1H, m), 8.05 (2H, m), 8.20 (2H, m).

Step 3 3-(2,4-Difluorophenoxy)-5,5-dimethyl-4-(4-(methylsulfonyl)phenyl)-5H-furan-2-one To a solution of 2-(2,4-difluorophenoxy)acetic acid 2-methyl-1-(4-(methylsulfonyl)phenyl)propan-1-one-2-yl ester (Step 2) (470 mg, 1.14 mmol) in acetonitrile (7 mL) was added DBU (187 μL, 1.25 mmol) and the resulting solution was heated at 50° C. for 20 minutes. After cooling to r.t. dichloromethane was added and the mixture was washed with 1N HCl, brine, filtered over cotton and the solvent evaporated under vacuum. Purification by silica gel chromatography followed by a swish in EtOAc/$Et_2O$ afforded 122 mg of the title compound.

$^1$H NMR ($CD_3COCD_3$) δ 1.70 (6H, s), 3.15 (3H, s), 6.90 (1H, m), 7.10 (1H, m), 7.30 (1H, m), 7.85 (2H, m), 8.00 (2H, m).

EXAMPLE 6

3-(4-Chlorophenoxy)-5,5-dimethyl-4-(4-(methylsulfonyl)phenyl)-5H-furan-2-one

Following the procedure described for example 1, the title compound was prepared from 4-chlorophenoxyacetic acid. M.P.: 113–114° C.

$^1$H NMR ($CD_3COCD_3$) δ 1.77 (6H, s), 3.15 (3H, s), 7.11 (2H, d), 7.31 (2H, d), 7.91 (2H, d), 8.04 (2H, d)

EXAMPLE 7

3-(3,4-Dichlorophenoxy)-5,5-dimethyl-4-(4-(methylsulfonyl)phenyl)-5H-furan-2-one Following the procedure described for example 1, the title compound was prepared from 3,4-dichlorophenyacetic acid. M.P.: 144–145° C.

$^1$H NMR ($CD_3COCD_3$) δ 1.78 (6H, s), 3.15 (3H, s), 7.12–7.15 (1H, m), 7.35–7.36 (1H, s), 7.49 (1H, d), 7.92 (2H, d), 8.04 (2H, d).

EXAMPLE 8

3-(4-Fluorophenoxy)-5,5-dimethyl-4-(4-(methylsulfonyl)phenyl)-5H-furan-2-one

Following the procedure described for example 1, the title compound was prepared from 4-flurophenoxyacetic acid.

$^1$H NMR ($CD_3COCD_3$) δ 1.76 (6H, s), 3.14 (3H, s), 7.02–7.13 (4H, m), 7.91 (2H, d), 8.01 (2H, d).

EXAMPLE 9

3-(4-Fluorophenylthio)-5,5-dimethyl-4-(4-(methylsulfonyl)phenyl)-5H-furan-2-one

Following the procedure described for example 1, the title compound was prepared from 4-fluorophenylthioacetic acid.

$^1$H NMR ($CDCl_3$)δ 1.55 (6H, s), 3.08 (3H, s), 6.85 (2H, m), 7.26 (2H, m), 7.35 (2H, d), 7.94 (2H, d)

EXAMPLE 10

3-(3,5-Difluorophenylthio)-5,5-dimethyl-4-(4-(methylsulfonyl)phenyl)-5H-furan-2-one To a mixture of 3,5-difluorothiophenol (1.0 g) and methyl bromoacetate (1.2 g) in methanol (20 mL) was added 2 mL of a solution of NaOH (0.69 mL of 10N in 3 mL of water), the mixture was stirred for 1 h, then 2 mL of 10N NaOH was added and the mixture stirred for another hour. The solvent was evaporated under vacuum, the residue taken in water and washed with $Et_2O$, then acidified with 1N HCl and extracted with ether. The ether extract was washed with water, dried over $MgSO_4$, filtered and the solvent evaporated under vacuum giving 850 mg of 3.5-difluorophenylthioacetic acid. This acid was reacted as in Step 1 to afford the title compound.

$^1$H NMR ($CDCl_3$) δ 1.60 (6H, s), 3.10 (3H, s), 6.60–6.80 (3H, m), 7.45 (2H, d), 8.00 (2H, d).

EXAMPLE 11

3-Phenylthio-5,5-dimethyl-4-(4-(methylsulfonyl) phenyl)-5H-furan-2-one

Following the procedure described for example 1, the title compound was prepared from phenylthioacetic acid. M.P.:98–114° C.

$^1$H NMR ($CD_3COCD_3$) δ 1.61 (6H, s), 3.16 (3H, s), 721–730 (5H, m), 7.61 (2H, d), 7.96 (2H, d).

Analysis calculated for $C_{19}H_{18}O_4S_2$: C, 60.94; H, 4.84; S, 17.12; Found: C, 61.01; H, 4.90: S, 16.94

EXAMPLE 12

3-(N-Phenylamino)-5,5-dimethyl-4-(4-(methylsulfonyl)phenyl)-5H-furan-2-one

Step 1 2-Phenylaminoacetic acid 2-methyl-1-(4-(methylsulfonyl) phenyl)propan-1-one ester Following the procedure described in example 13 Step 1 but using aniline the title compound was obtained.

$^1$H NMR ($CD_3COCD_3$) δ 1.70 (6H, s), 3.15 (3H, s), 3.95 (2H, br s), 5.15 (1H, br s), 6.40 (2H, m), 6.55 (1H, m), 700 (2H, m), 8.00 (2H, m), 8.25 (2H, m).

Step 2 3-N-Phenylamino-5,5-dimethyl-4-(4-(methylsulfonyl)phenyl)-5H-furan-2-one

Following the procedure described in example 13 Step 2 but using 2-phenylaminoacetic acid 2-methyl-1-(4-

(methylsulfonyl)phenyl) propan-1-one ester the title compound was obtained.

$^1$H NMR (CD$_3$COCD$_3$) δ 1.65 (6H, s), 3.05 (3H, s), 6.70 (3H, m), 6.95 (2H, m), 7.25 (1H, br s), 7.50 (2H, m), 7.75 (2H, m).

EXAMPLE 13

3-(N-Methyl-N-phenylamino)-5,5-dimethyl-4-(4-(methylsulfonyl)phenyl)-5H-furan-2-one Step 1 2-(N-Phenyl-N-methylamino)acetic acid 2-methyl-1-(4-(methylsulfonyl)phenyl)propan-1-one ester To a solution of 2-bromoacetic acid 2-methyl-1-(4-(methylsulfonyl)phenyl)propan-1-one ester (example 5, Step 1) (1.0 g, 2.75 mmol) in toluene (2.5 mL) was added N-methylaniline (3.0 mL, 27.5 mmol) and the resulting solution was heated at 115° C. for 16 hrs. After cooling to r.t. the reaction mixture was washed with brine and filtered through cotton. Purification by silica gel chromatography provided 850 mg of the title compound.

Step 2 3-(N,-Methyl-N-phenylamino)-5,5-dimethyl-4-(4-(methylsulfonyl) phenyl)-5H-furan-2-one To a solution of 2-(N-phenyl-N-methylamino)acetic acid 2-methyl-1-(4(methylsulfonyl)phenyl)propan-1-one ester (700 mg, 1.80 mmol) in acetonitrile (3 mL) was added DBU (2.7 mL, 18.0 mmol) and the resulting solution was heated at 60° C. for 1 h. After cooling to r.t. dichloromethane was added and the mixture was washed with 1N HCl, brine and filtered through cotton and the solvent was evaporated under vacuum. Purification by silica gel chromatography followed by swish in EtOAc/Hex, afforded 266 mg of the title compound.

$^1$H NMR (CD$_3$COCD$_3$) δ 1.70 (6H, s), 3.05 (3H,s), 3.15 (3H, s), 6.70 (1H, m), 6.80 (2H, m), 7.10 (2H, m), 7.65 (2H, m), 7.90 (2H, m)

EXAMPLE 14

3-Cyclohexyloxy-5,5-dimethyl-4-(4-(methylsulfonyl)phenyl)-5H-furan-2-one

Step 1 2-Bromo-2-methyl-1-(4-(methylsulfonyl)phenyl) propan-1-one

To a solution of 2-methyl-1-(4-(methylthio)phenyl) propan-1-one (example, 1, Step 1) (417.94 g) in ethyl acetate (1.2 L) and cyclohexane (1.7L) was added bromine (110 mL) portionwise. After stirring for 10 min the mixture was washed with water, saturated sodium bicarbonate and brine. To this mixture was then added sodium tungstate (6.7 g), Aliquat 336 (25 g) and water (200 mL). The mixture was then heated to 50° C. and hydrogen peroxide (30%, 600 mL) was added slowly. Ethyl acetate and water were then added to the mixture and the organic layer separated, washed with water, dried over sodium sulfate, filtered and the title compound crystalized and was collected by filtration.

Step 2 2-Cyclohexyloxyacetic acid 2-methyl-1-(4-(methylsulfonyl) phenyl)propan-1-one ester A solution of 2-cyclohexyloxyacetic acid (1.74 g, 11 mmol), 2-bromo-2-methyl-1-(4-(methylsulfonyl)phenyl) propan-1-one (3.05 g, 10 mmol) and diisopropylethylamine (2.20 g, 17 mmol) in 30 ml of ethanol was refluxed for 15 h. The solvent was evaporated and the residue dissolved in water and extracted with EtOAc, washed with 5% HCl, saturated sodium bicarbonate, brine and dried over MgSO$_4$, filtered and the solvent evaporated under vacuum. Purification by silica gel chromatography afforded 3.0 g of the title compound.

Step 3 3-Cyclohexyloxy-5,5-dimethyl-4-(4-(methylsulfonyl)phenyl)-5H-furan-2-one

A solution of the ester from the previous step (492 mg, 129 mmol) and DBU (1 mL) in 5 mL of acetonitrile was heated at reflux for 15 h. To the cooled solution was added 5% HCl and the mixture was extracted with EtOAc, washed with a saturated solution of ammonium chloride and dried over MgSO$_4$, filtered and the solvent evaporated under vacuum. Purification by silica gel chromatography afforded the title compound.M.P.: 143–144° C.

$^1$H NMR (CD$_3$COCD$_3$) δ 1.20–1.35 (3H, m), 1.40–1.50 (3H, m), 1.66 (6H, s), 160–1.70 (2H, m), 1.85–1.95 (2H, m), 3.20 (3H, s), 4.85 (1H,m), 800–8.10 (4H, m)

Analysis calculated for C$_{19}$H$_{24}$O$_5$S: C, 62.62; H, 6.64; Found: C, 62.28; H, 6.57

EXAMPLE 15

3-Phenylthio-4-(4-(methylsulfonyl)phenyl)-5H-furan-2-one

At 0° C., triethylamine (335 μL) was added to a solution of thiophenoxyacetic acid (161 mg) and 2-bromo-1-(4-(methylsulfonyl)phenyl) ethanone (272 mg, WO 9500501, example 9, Step 1) in 5 mL of acetonitrile and the mixture was stirred at 0° C. for 1 h. The reaction mixture was then cooled to −20° C. and DBU (265 μL) was added. The mixture was stirred for 30 min. at −20° C. and was quenched by addition of 1N HCl. The product was extracted with EtOAc, dried over sodium sulfate and partially purified by silica gel chromatograph. The impure product was recrystalized from EtOAc/Hexane to afford the title compound as a solid $^1$H NMR (CDCl$_3$) δ 3.10 (3H, s), 5.25 (2H, s), 7.24–7.38 (5H, m), 7.93 (2H, d), 8.03 (2H, d).

Analysis calculated for C$_{17}$H$_{14}$O$_4$S$_2$: C, 58.94; H, 4.07; Found: C, 58.88; H, 4.18

EXAMPLE 16

3-Benzyl-5,5-dimethyl-4-(4-(methylsulfonyl) phenyl)-5H-furan-2-one

Step 1 3-Phenylpropanoic acid 2-methyl-1-(4-(methylthio) phenyl) propan-1-on-2-yl ester To a −30° C. solution of 2-hydroxy-2methyl-1-(4-(methylthio)phenyl)propan-1-one (1.05 g, example 1, Step 2) in dichloromethane (20 mL) was added 3-phenylpropionyl chloride (1.68 g) in dichloromethane (10 mL) followed by pyridine (791 mg) and the mixture was allowed to warm up slowly to 25° C. and stirred for 12 h. Ethyl acetate was added to the mixture and it was washed with 1N HCl, brine, dried over magnesium sulfate filtered and the solvent was evaporated under vacuum. Purification by silica gel chromatography afforded 1.36 g of the title compound.

$^1$H NMR (CD$_3$COCD$_3$) δ 1.65 (6H, s), 2.50 (3H, s), 2.55–2.65 (2H, t), 2.75–2.85(2H, t), 7.10–7.40 (7H, m), 7.90–8.00 (2H, d)

Step 2 3-Benzyl,-5,5-dimethyl-4-(4-(methylthio)phenyl-5H-furan-2-one

To a 0° C. solution of the ester from the previous step (1.14 g) in DMF (10 mL) and THF (2 mL) was added sodium hydride (120 mg of 80% dispersion) and the mixture was stirred for 2 h at 25° C. Then it was poured over icy 1N HCl and extracted with ethyl acetate, the organic layer was washed with water, brine, dried over MgSO$_4$ and the solvent evaporated under vacuum. The residue was purified by silica gel chromatography affording 596 mg of the title compound.

$^1$H NMR (CD$_3$COCD$_3$) δ 1.50 (6H, s), 2.55 (3H, s), 3.50 (2H, s), 7.05–7.30 (7H, m), 7.35–7.40 (2H, d)

Step 3 3-Benzyl-5,5-dimethyl-4-(4-(methylsulfonyl) phenyl)-5H-furan-2-one

To a 0° C. solution of the lactone from the previous step (596 mg) in dichloromethane (10 mL) and methanol (5 mL)

was added portionwise MMPP (2×590 mg) and the mixture was allowed to slowly warm-up to 25° C. After 2 h. at 25° C. the mixture was partitioned between dichloromethane and water, the organic layer was washed with brine, dried over $MgSO_4$, filtered and the solvent evaporated under vacuum. The residue was swished in ether to yield 530 mg of the title compound. Analysis calculated for $C_{20}H_{20}O_4S$: C, 67.40; H, 5.65; Found: C, 67.28; H, 578

EXAMPLE 17

3-(3,4-Difluorophenylhydroxymethyl)-5,5-dimethyl-4-(4-(methylsulfonyl)phenyl)-5H-furan-2-one Using a procedure similar to the Steps 1, 2 and 3 of example 19 but using 3,4-difluorobenzaldehyde as an electrophile the title compound was obtained.

$^1$H NMR ($CD_3COCD_3$) δ 1.45 (6H, s), 3.15 (3H, s), 5.00 (1H, bs), 5.50 (1H, bs), 645–6.55 (2H, d), 7.00–7.30 (3H, m), 7.95–8.05 (2H, d).

EXAMPLE 18

3-(3,4-Difluorobenzoyl)-5,5-dimethyl-4-(4-(methylsulfonyl)phenyl)-5H-furan-2-one Using a procedure similar to Step 4 of example 19 and using the compound obtained in example 17, the title compound was obtained $^1$H NMR ($CD_3COCD_3$) δ 1.75 (6H, s), 3.10 (3H, s), 7.35–7.45 (1H, m), 7.65–7.75 (2H, d), 7.75–7.90 (2H, m), 7.95–8.05 (2H, d).

EXAMPLE 19

3-Benzoyl-5,5-dimethyl-4-(4-(methylsulfonyl) phenyl)-5H-furan-2-one

Step 1 Acetic acid 2-methyl-1-(4-methylthiophenyl)propan-1-on-2-yl ester

To a 0° C. solution of 2-hydroxy-2methyl-1-(4-(methylthio)phenyl)propan-1-one (150 g, example 1, Step 2), DBU (217 g) and DMAP (7 g) in dichloromethane (850 mL) was added acetyl chloride (112.2 g) dropwise and the mixture was stirred for 6 h. at 25° C. More DBU (32.5 g) was added and the mixture was stirred an additional 16 h. The reaction mixture was poured over 2N HCl (800 mL) and the organic layer was separated, washed with a saturated solution of $NaHCO_3$, dried over $MgSO_4$, filtered and the solvent was evaporated under vacuum. The residue was swished in $Et_2O$, then 25% ethyl acetate in hexane, then filtered and dried giving 74 g of the title compound.

$^1$H NMR ($CD_3COCD_3$) δ 1.60 (6H, s), 1.90 (3H, s), 2.55 (3H, s), 7.30 (2H, d), 8.00 (2H, d).

Step 2 5.5-Dimethyl-4-(4-(methylthio)phenyl)-5H-furan-2-one

To a 0–5° C. solution of the ester from the previous step (74 g) in DMF (1.2L) was added NaH (9 g, 80% dispersion) portionwise and the mixture was stirred for 3 h. Saturated aquous $NH_4Cl$ was added slowly. The mixture was then partitioned between ethyl acetate and water, the organic layer was washed with water, dried with $Na_2SO_4$, filtered and the solvent was evaporated under vacuum. The residue was swished in 30% ethyl acetate/hexane to yield the title compound (38 g).

$^1$H NMR ($CD_3COCD_3$) δ 1.70 (6H, s), 2.55 (3H, s), 6.40 (1H, s), 7.40 (2H, d), 7.70 (2H, d).

Step 3 5,5-Dimethyl-4-(4-(methylsulfonyl)phenyl)-3-(phenylhydroxymethyl)-5H-furan-2-one To a −78° C. solution of the lactone (702 mg) obtained in the previous step in THF was added 0.67M LDA (9.25 mL) and the mixture was reacted for 5 min. Benzoyl chloride (913 mg) was then added at −78° C. and after 15 min the mixture was poured over icy 1N HCl. The organic material was extracted with ethyl acetate, washed with brine, dried with $MgSO_4$, filtered and the solvent was evaporated under vacuum. The residue was dissolved in dichloromethane (10 mL) and methanol (10 mL) and the solution cooled to 0° C. MMPP (4.9 g) was added and the mixture warmed and stirred at 25° C. for 2 h. The mixture was poured over icy water and the organic layer was dried over $MgSO_4$, filtered and the solvent evaporated under vacuum. The residue was purified by silica gel chromatography to yield 190 mg of compound which was dissolved in methanol(2 mL) and THF (1 mL), cooled to 0° C. and a catalytic amount of NaOH was added. The mixture was poured in icy water and extracted with ethyl acetate, the organic layer was washed with brine, dried over $MgSO_4$, filtered and the solvent evaporated under vacuum.

Step 4 3-Benzoyl-5,5-dimethyl-4-(4-(methylsulfonyl) phenyl)-5H-furan-2-one

The residue was dissolved in acetone (3 mL), and Jone's reagent (3M, 150 μL) was added. The mixture was stirred for 1 h, then poured over icy water and extracted with ethyl acetate, the organic layer was washed with brine, dried over $MgSO_4$, filtered and the solvent was evaporated under vacuum. The residue was swished in ether to yield the title compound (123 mg).

Analysis calculated for $C_{20}H_{18}O_5S$: C, 64.85; H, 4.84; Found: C, 64.63; H, 5.23

EXAMPLE 20

4-(4-(Methylsulfonyl)phenyl)-3-phenoxy-1-oxaspiro [4,4]non-3-en-2-one

Using a procedure similar to the one used in example 1 but using (1-hydroxycyclopentyl)-(4-(methylsulfonyl) phenyl)methanone from example 21, Step 3 and phenoxyacetic acid the title compound was obtained.

$^1$H NMR ($CDCl_3$) δ 1.80–2.30 (8H, m), 3.04 (3H, s), 6.95–7.35 (5H, m), 7.75 (2H, d), 7.95 (2H, d).

EXAMPLE 21

4-(4-(Methylsulfonyl)phenyl)-3-phenylthio-1-oxaspiro[4,4]non-3-en-2-one

Step1: Cyclopentyl-(4-(methylthio)phenyl)methanone

To a suspension of anhydrous aluminum chloride (9.3 g, 69.6 mmol) in 58 mL $CHCl_3$ at 0° C. was added dropwise cycopentanecarbonyl chloride (10.0 g, 75.4 mmol), followed by thioanisole (7.21 g, 58.0 mmol). The ice bath was sremoved and the mixture was stirred at room temperature for 2 h. Water (200 ml) was added with cooling, the layers were separated and the aqueous layer was extracted with $CHCl_3$ (3×50 mL). The combined aqueous layers were dried over $MgSO_4$, filtered and concentrated. The residue was chromatographed on silica gel (4% EtOAc/hexane) to give 11.9 g of the title ketone (93%).

$^1$H NMR ($CD_3COCD_3$) δ 7.94 (d, 2H), 7.36 (d, 2H), 3.79 (q, 1H), 2.56 (s, 3H), 2.00–1.71 (m, 4H), 170–1.50 (m, 4H).

Step 2: (1-Hydroxycyclopentyl)-(4-(methylthio)phenyl) methanone

To a solution of the ketone from Step 1 (7.2 g, 32.7 mmol) in 4.7 ml $CCl_4$ and 9.6 ml toluene was added Aliquat 336 (2.11 g, 5.20 mmol) and powdered NaOH (2.88 g, 71.9 mmol) and the mixture was stirred for 16 h at r.t. To the brown mixture was added 100 ml of 5% aq2. HCl and extracted with EtOAc (4×100 ml). The combined organic layers were washed with brine, dried over $MgSO_4$, filtered and concentrated. Chromatography on silica gel (20% EtOAc/hexane) gave 5.4 g of the title compound as a white waxy solid (70%).

$^1$H NMR (CD$_3$COCD$_3$) δ 8.11 (d, 2H), 7.31 (d, 2H), 4.63 (s, 1H, disappears by D$_2$O wash), 2.56 (s, 3H), 2.24 (m, 2H), 1.89 (m, 4H), 1.71 (m, 2H).

Step 3 (1-Hydroxycyclopentyl)-(4-(methylsulfonyl)phenyl) methanone

The sulfide obtained in Step 2 (56 g) was dissolved in dichloromethane (800 mL) and methanol (200 mL) and treated with MMPP (139 g) and stirred for 3 h. The organic layer was diluted with dichloromethane, washed with water and brine, dried over MgSO$_4$, filtered and the solvent evaporated to afford the title compound.

Step 4 4-(4-Methylsulfonyl)phenyl)-3-phenylthio-1-oxaspiro[4,4]non-3-en-2-one

The hydroxyketone from the previous step was reacted with phenylthioacetic acid as in the procedure for example 1, Step 4 to afford the title compound.

$^1$H NMR (CDCl$_3$) δ 1.70–2.05 (8H, m), 3.06 (3H, s), 7.10–7.25 (5H, m), 7.35 (2H, d), 7.90 (2H, d).

EXAMPLE 22

4-(2-Oxo-3-phenylthio-1-oxa-spiro[4,4]non-3-en-4-yl)benzenesulfonamide

To a solution of 1-(hydroxycyclopentyl)-(4-methylthiophenyl) methanone (52 g, example 21, Step 2) in CH$_2$Cl$_2$ (400 mL) and methanol (200 mL) at 0° was added portionwise MMPP (61 g). After sitrring for 3 h the reaction mixture was washed with water, dried over Na$_2$SO$_4$, filtered and evaporated to dryness to provide the sulfoxide intermediate which (7.56 g) was dissolved in TFAA (100.0 mL) and refluxed for 3 h. The mixture was cooled to 0° C. and 10N NaOH (24 mL), was added dropwise and under nitrogen. After vigorous stirring for 0.5 h, acetic acid (100 mL) and water (20 mL) was added. The mixture was cooled to 0° C. and chlorine gas was bubbled for 20 min. The excess chlorine was removed under vacuum and the mixture was poured over icy water and extracted with ethyl acetate. The extracts were washed with water, saturated NaHCO$_3$ and brine. The organic layer was cooled to 0° C. and t-butylamine (10 mL) was added and stirred for 1 h. The reaction mixture was diluted with water and neutralized with 6N HCl, washed with brine, dried over MgSO$_4$ filtered and the solvent evaporated under vacuum. The residue was swished in ether. This hydroxyketone (325 mg) was then reacted as in example 1, Step 4 using phenylthioacetic acid (200 mg) to give an intermediate (300 mg) which was stirred in dichloromethane (2 mL) and trifluoroacetic acid (8 mL) for 18 h. The solvents were then evaporated under vacuum and the residue was recrystallized from ethanol to afford the title compound.

$^1$H NMR (CD$_3$COCD$_3$) δ 1.65–2.20 (8H, m), 6.68 (2H, br s), 7.25 (5H m), 7.55 (2H, d), 7.95 (2H, d).

EXAMPLE 23

3-(4-Fluorobenzyl)-5,5-dimethyl-4-(4-(methylsulfonyl)phenyl)-5H-furan-2-one

Using a procedure similar to the one for example 16 but using 3-(4-fluorophenyl)propionyl chloride the title compound was obtained.

$^1$H NMR (CD$_3$COCD$_3$) δ 1.50 (6H, s), 3.15 (3H, s), 4.45 (2H, s), 7.05–7.15 (2H, m), 7.50–7.60 (2H, d), 7.85–7.95 (2H, m), 7.95–8.05 (2H, d).

EXAMPLE 24

3-(3,4-Difluorophenoxy)-5-methoxy-5-methyl-4-(4-(methylsulfonyl)phenyl)-5H-furan-2-one Step 1 2-Bromo-1-(4-(methylsulfonyl)phenyl)propan-1-one Following a procedure similar to the one used in example 1, Step 1 but using propionyl chloride, 1-(4-(methylsulfonyl)phenyl)propan-1-one was obtained. A solution of this compound (163.4 g) in chloroform (2.2L) was then cooled to 0° C. and treated with bromine (40 mL in 200 mL CHCl$_3$) and concentrated HBr (10 mL). The reaction mixture was washed with water, saturatd sodium bicarbonate and brine, dried over sodium sulfate, filtered and the solvent evaporated under vacuum. The residue was swished in ethyl acetate:hexane 1:1 to give the title compound (191 g).

Step 2 5-Hydroxy-5-methyl-4-(4-(methylsulfonyl)phenyl)-3-phenylthio-5H-furan-2-one To a mixture of 2-bromo-1-(4-(methylsulfonyl)phenyl) propan-1-one (6.0 g, 20.6 mmol) and thiophenoxyacetic acid (3.8 g, 22.6 mmol) in acetonitrile (60 mL) was added triethylamine (4.0 mL, 28.8 mmol). The mixture was stirred at r.t. for 3 h. T.L.C. showed no bromoketone remaining and DBU (4.0 mL) was added. The mixture was stirred at r.t. for 1 h., then air was bubbled through the mixture for another hour. After dilution with water, the mixture was extracted with EtOAc. The EtOAc extract was washed with 1N aquous HCl, brine, dried over MgSO$_4$, filtered and the solvent evaporated under vacuum. The residue was swished in Et$_2$O to give the title compound (6.0 g) as a pale yellow powder.

$^1$H NMR (CD$_3$COCD$_3$) δ 1.68 (3H, s), 3.16 (3H, s), 6.86 (1H, s), 7.35 (5H, m), 7.78 (2H, d), 7.98 (2H, d).

Step 3 5-Methoxy-5-methyl-4-(4-(methylsulfonyl)phenyl)-3-phenylthio-5H-furan-2-one The alcohol (2.5 g, 6.6 mmol) from the previous step was dissolved in methanol (100 mL), THF (20 mL) and concentrated HCl (5 mL) and heated at 70° C. for 24 h. After cooling to 0° C. the precipitate formed was filtered, washed with methanol and dried under vacuum to give the title compound (2.0 g) as a yellow solid.

$^1$H NMR (CD$_3$COCD$_3$) δ 1.65 (3H, s), 3.15 (3H, s), 3.40 (3H, s), 7.18–7.40 (5H, m), 7.88 (2H, d), 7.98 (2H, d).

Step 4 3-(3,4-Difluorophenoxy)-5-methoxy-5methyl-4-(4-(methylsulfonyl)phenyl)-5H-furan-2-one To a solution of the compound obtained in the previous step (2.0 g, 5.1 mmol) in dichloromethane (100 mL) at r.t. was added mCPBA (4.0 g, Aldrich 57–86%, ~16 mmol). The mixture was stirred at r.t. for 3 h and more mCPBA (2.0 g) was added. After stirring for another hour the mixture was washed with 1N NaOH, brine, dried and concentrated under vacuum to yield a disulfone as a white foam (2.0 g). To a solution of 3,4-difluorophenol (2.0 g, 14.9 mmol) in DMF was added 10 N NaOH (1 mL, 10 mmol). After 30 min. a solution of the above disulfone (2.0 g, 4.7 mmol) in DMF was added. The mixture was heated at 80–85° C. for 1.5 h. After cooling the mixture was diluted with water, extracted with EtOAc, the organic extracts were washed with 1N NaOH, 1N HCl, brine, dried over MgSO$_4$, filtered and the solvent evaporated under vacuum. Purification by silica gel chromatography afforded the title compound as a white solid (600 mg).

$^1$H NMR (CD$_3$COCD$_3$) δ 1.86 (3H, s), 3.16 (3H, s), 3.40 (3H, s), 6.95–7.40 (3H, m), 8.08 (2H, d), 8.16 (2H, d).

EXAMPLE 25

3-(5-Chloro-2-pyridyloxy)-5,5-dimethyl-4-(4-(methylsulfonyl)phenyl)-5H-furan-2-one To a mixture of 2chloroacetic acid 2-methyl-1-(4-(methylsulfonyl)phenyl)propan-1-one ester (1.0 g, 3.13 mmol, prepared similarly to the compound of example 5, Step 1) and 5-chloro-2-pyridinol (0.41 g, 3.16 mmol) in CH$_3$CN (20 mL) was added DBU (1.5 mL, 10.0 mmol) at r.t. The mixture was stirred for 1 h, then heated at 65–70° C. for 3 h. The volatile solvents were removed in vacuo. The residue was chromatographed over silica gel and eluted with hexane:EtOAc (1:1) to yield a colorless oily residue which was swished in Et$_2$O to provide the title compound as a white powder (230 mg).

$^1$H NMR (CD$_3$COCD$_3$) δ 1.80 (6H, s), 3.20 (3H, s), 7.18 (1H, d), 7.94 (3H, m), 8.06 (2H, d), 8.19 (1H, d).

EXAMPLE 26

3-(2-pyridyloxy)-5,5-dimethyl-4-(4-(methylsulfonyl) phenyl)-5H-furan-2-one

Following the procedure described for example 25, the title compound wa prepared from 2-hydroxypyridine.

$^1$H NMR (CD$_3$COCD$_3$) δ 1.78 (6H, s), 3.15 (3H, s), 700–7.20 (2H, m), 7.80–8.20 (6H, m).

EXAMPLE 27

3-(6-Methyl-2-pyridyloxy)-5,5-dimethyl-4-(4-(methylsulfonyl)phenyl)-5H-furan-2-one Following the procedure described for example 25, the title compound was prepared from 2-hydroxy-6-methylpyridine.

$^1$H NMR (CD$_3$COCD$_3$) δ 1.75 (6H, s), 3.14 (3H, s), 6.85 (1H, d), 7.00 (1H, d), 7.70 (1H, t), 7.90 (2H, d), 8.00 (2H, d).

EXAMPLE 28

3-(3-Isoquinolinoxy)-5,5-dimethyl-4-(4-(methylsulfonyl)phenyl)-5H-furan-2-one

Following the procedure described for example 25, the title compound was prepared from 3-hydroxyisoquinoline.

$^1$H NMR (CD$_3$COCD$_3$)δ1.80 (6H, s), 3.14)3H, s), 7.40–8.10 (9H, m), 9.00 (1H, s).

EXAMPLE 29

3-(4-Methylsulfonyl)phenyl)-2-phenoxycyclopent-2-enone

Step 1 1-(4-(Methylthio)phenyl)-5-phenoxypenta-1,4-dione

To a mixture containing 1-phenoxybut-3-en-2-one (1.0 g) (A. G. Schultz, R. D. Lucci, W. Y. Fu, M. H. Berger, J. Erhardt and W. K. Hagmann, J. Amer. Chem. Soc. 100, 2150, (1978)), 4-(methylthio)benzaldehyde (0.62 g) and triethylamine (0.343 mL) in 1,4-dioxane (20 mL) was added 3-benzyl-5-(2-hydroxyethyl)-4-methylthiazolium chloride (110 mg). After stirring 4h. at 100° C. the reaction mixture was extracted with EtOAc, dried over MgSO$_4$, filtered and the solvent evaporated under vacuum. The residue was purified by silica gel chromatography (20% EtOAc/Hexane) to afford 140 mg of the title compound as an oil.

Step 2 3-(4-(Methylthio)phenyl)-2-phenoxycyclopent-2-enone

To the diketone of Step 1 (120 mg) in methanol (80 mL) was added DBU (0.1 mL). The resulting mixture was heated at 60° C. for 18 h. The methanol was then evaporated and to the crude mixture was added saturated aqueous ammonium chloride, the mixture was then extracted with EtOAc, the organic layer was dried over MgSO$_4$, filtered, and the solvent evaporated under vacuum. The residue was purified by silica gel chromatography (20% EtOAc/hexane) to afford the title compound.

Step 3 (4-(Methylsulfonyl)phenyl)-2-phenoxycyclopent-2-enone

To the compound obtained in Step 2 (60 mg) in dichloromethane (4.5 mL) and methanol (2.4 mL) was added Oxone® (450 mg) in water (1 mL) and the reaction mixture was stirred for 1 h. Water was added to the mixture which was then extracted with dichloromethane, the organic layers were combined and dried over MgSO$_4$, filtered and the solvent evaporated under vacuum. Purification by silica gel chromatography afforded the title compound.

$^1$H NMR (CD$_3$COCD$_3$) δ2.65 (2H, t), 3.15 (3H, s), 3.20 (2H, t), 7.05–7.35 (5H, m), 8.10 (4H, m).

EXAMPLE 30

2-(3,4-difluorophenoxy)-3-(4-methylsulfonylphenyl)-cyclopent-2-enone

Step 1: 3,4-Difluorophenoxymethyl Vinyl Ketone

To a suspension of 3,4-difluorophenoxy acetic acid (5.00 g, 25.7 mmol) lithium salt in DME (20 mL) was added to a 1M THF solution of vinyl magnesium bromide (38 mmol). After a period of 18h, the resulting clear solution was poured over 1N HCl (67 mL). The aqueous phase was then extracted with Et$_2$O. The ethereal phase was washed with H$_2$O, 1M K$_2$CO$_3$ then H$_2$O. After drying over MgSO$_4$ and evaporation an orange oil was obtained and used as such for the next step.

Step 2: 2-(3,4-difluorophenoxy)-3-(4-methylsulfonylphenyl)-cyclopent-2-enone

Following the procedure described in Example 29 but using the compound obtained in the previous step the title compound was obtained.

$^1$H NMR (CD$_3$COCD$_3$) δ2.60 (2H, t), 3.15 (3H, s), 3.20 (2H, t), 6.90 (1H, m), 7.15 (1H, m), 7.25 (1H, Q), 8.10 (4H, 2d).

EXAMPLE 32

3-(5-Benzothiophenyloxy)-5,5-dimethyl-4-(4-(methylsulfonyl)phenyl)-5H-furan-2-one Following the procedure described for Example 25, the title compound was prepared from 5-hydroxybenzothiphene.

M.P.: 150–152° C. $^1$H NMR (CD$_3$COCD$_3$) δ1.78 (6H, s), 3.08 (3H, s), 7.17 (1H, dd), 7.32 (1H, d), 7.56 (1H, d), 7.68 (1H, d), 7.92–7.99 (5H, m).

EXAMPLE 37

5,5-dimethyl-4-(4-methylsulfonyl-phenyl)-3-(pyridin-4-yloxy)-5H-furan-2-one

To a R.T. solution of 2-chloroacetic acid 2-methyl-1-(4-(methysulfonyl)phenyl)propan-1-one ester (318 mg, 1 mmol) in DMF (5 mL) was added 4-pyridone (380 mg, 4.0 mmol) followed by DBU (623 mg, 4.1 mmol) and the mixture was slowly warmed up to R.T. for 16 hrs and then to 60–70° C. for 1–2 hours. The mixture was cooled to R.T. and poured on icy dilute NH$_4$Cl and EtOAc; the organic layer was separated and the aqueous further extracted with EtOAc. The combined organic layers were washed with brine, dried with Na$_2$SO$_4$ and the solvents were removed in vacuo. The residue was purified on silica gel chromatography (1/1, Acetone/toluene) to provide the title compound.

$^1$H NMR (CD$_3$COCD$_3$) δ1.8(6H,s), 3.15(3H,s), 7.05–7.15(2H,m), 7.9–8.1(4H,AB), 8.4–8.5(2H,m).

EXAMPLE 38

5,5-dimethyl-4-(4-methylsulfonyl-phenyl)-3-(pyridin-3-yloxy)-5H-furan-2-one

To a R.T. solution of 2-chloroacetic acid 2-methyl-1-(4-(methylsulfonyl)phenyl)propan-1-one ester (318 mg, 1 mmol) in DMF (5 mL) was added 3-hydroxypyridine (95 mg, 1 mmol) followed by DBU (623 mg, 4.1 mmol) and the mixture was slowly warmed up to R.T. for 16 hrs and then to 60–70° C. for 1–2 hours. The mixture was cooled to R.T. and poured on icy dilute $NH_4Cl$ and EtOAc; the organic layer was separated and the aqueous further extracted with EtOAc. The combined organic layers were washed with brine, dried with $Na_2SO_4$ and the solvents were removed in vacuo. The residue was purified on silica gel chromatography (1/1, Acetone/toluene) to provide the title compound.

Analysis calculated for $C_{18}H_{17}NO_5S$: C, 60.16; H, 4.77; N, 3.90. Found: C, 60.01; H, 4.81; N, 3.90.

EXAMPLE 39

3-(2-Methyl-5-pyridyloxy)-5,5-dimethyl-4-(4-(methylsulfonyl)phenyl)-5H-furan-2-one Following the procedure described for Example 25, the title compound was prepared using 5-hydroxy-2-methyl pyridine M.P.: 168–169° C.

$^1$H NMR ($CD_3COCD_3$) δ1.77 (6H, s), 2.41 (3H, s), 3.15 (3H, s), 7.14 (1H, d), 7.37 (1H, dd), 7.93 (2H, d), 8.03 (2H, d), 8.25 (1H, d).

EXAMPLE 44

3(2-Fluoro-4-trifluoromethyl)phenoxy-4-(4-methylsulfonyl)phenyl-5,5-dimethyl-5H-furan-2-one Following the procedure for Example 25, the title compound was prepared from 2-fluoro-4-trifluoromethylphenol; m.p.: 192–194, $^1$H NMR ($CD_3COCD_3$) d 1.78 (6H, s), 3.16 (3H, s), 7.49 (2H, m), 7.64 (1H, d, J=11.6 Hz), 7.95 (2H, d, J=8.3 Hz), 8.05 (2H, d, J=8.5 Hz). Analysis calculated for $C_{20}H_{16}F_4O_5S$: C, 54.06; H, 3.63; Found C, 54.09, H, 3.72.

EXAMPLE 45

3-(5-Chloro-2-pyridylthio)-5,5-dimethyl-4-(4-methylsulfonyl)phenyl-5H-furan-2-one Following the procedure described for Example 25, the title compound was prepared from 5-chloro-2-mercaptopyridine.

$^1$H NMR ($CD_3COCD_3$) δ1.70(6H, s), 3.20(3H, s), 7.38 (1H, d), 7.72(3H, m), 8.06(2H, d), 8.42(1H, m).

EXAMPLE 46

2-(3,5-Difluorophenoxy)-3-(4-methylsulfonylphenyl)-cyclopent-2-enone

Using similar protocol described for Example 29 but using 1-(3,5-difluorophenoxy)but-3-en-2-one the title compound was obtained.

$^1$H NMR ($CD_3COCD_3$) δ2.60 (2H, t), 3.15 (3H, s), 3.20 (2H, t), 6.60 to 6.85 (3H, m), 8.10 (4H, 2d).

EXAMPLE 47

3-(2-Pyrimidinoxy)-5,5-dimethyl-4-(4-methylsulfonyl)phenyl-5H-furan-2-one

Following the procedure described for Example 25, the title compound was prepared from 2-hydroxypyrimidine hydrochloride.

$^1$H NMR($CD_3COCD_3$) δ1.78(6H, s), 3.18(3H, s), 7.34 (1H, t), 7.40(2H, d), 8.06(2H, d), 8.68(2H, d).

EXAMPLE 48

3-(3-Methyl-2-pyridyloxy)-5,5-dimethyl-4-(4-methylsulfonyl)phenyl-5H-furan-2-one Step 1: 2-Hydroxy-3-methylpyridine To 10% aqueous $H_2SO_4$(90 mL) at 0° C. was added 2-amino-3-methylpyridine (6.0 g, 56 mmol). The mixture was stirred at 0° C. for 30 mins and a solution of 4N aqueous $NaNO_2$ (13 mL) was added dropwise over a period of 15 min. The mixture was further stirred and warmed to rt over 1h. The pH was then adjusted to 6–7 by the addition of 10N aqueous NaOH. The whole mixture was then extracted with $CHCl_3$, washed with $H_2O$, dried (anhydrous $MgSO_4$) and concentrated in vacuo. The crude material was swished with $Et_2O$ to give the title compound (2.5 g, 42%) as a white solid.

$^1$H NMR($CD_3COCD_3$) δ2.02(3H, s), 6.10(1H, m), 7.30 (2H, m).

Step 2: 3-(3-Methyl-2-pyridyloxy)-5,5-dimethyl-4-(4-methylsulfonyl)phenyl-5H-furan-2-one Following the procedure described for Example 25, the title compound was prepared from 2-hydroxy-3-methylpyridine.

$^1$NMR($CD_3COCD_3$) δ1.78(6H, s), 2.30(3H, s), 3.14(3H, s), 7.05(1H, m), 7.65(1H, m), 7.95(3H, m), 8.02(2H, d).

EXAMPLE 49

3-(3-Chloro-5-pyridiloxy)-5,5-dimethyl-4-(4-(methylsulfonyl)phenyl)-5H-furan-2-one Following the procedure described for Example 25, the title compound was prepared using 2-chloro-5-hydroxypyridine. M.P.: 176–177° C.

$^1$H NMR ($CD_3COCD_3$) δ1.79 (6H, s), 3.16 (3H, s), 7.70 (1H, m), 7.96 (2H, d), 8.05 (2H, d), 8.33 (1H, d), 8.40 (1H, d).

EXAMPLE 51

3-(3-(1,2,5-Thiadiazolyl)oxy)-4-(4-(methylsulfonyl)phenyl)-5,5-dimethyl-5H-furan-2-one Following the procedure for example 25, the title compound was prepared from 3-hydroxy-1,2,5-thiadiazol; m.p.: 127–129.

$^1$H NMR ($CD_3COCD_3$) δ1.78 (6H, s), 3.16 (3H, s), 7.92 (2H, d, J=8.6 Hz), 8.06 (2H, d, J=8.6 Hz), 8.49 (1H, s). Analysis calculated for $C_{15}H_{14}N_2O_5S_2$: C, 49.17; H, 3.85; N, 7.65; Found: C, 49.01, H, 3.84; N, 7.37.

EXAMPLE 52

3-(5-Isoquinolinoxy)-5,5-dimethyl-4-(4-methylsulfonyl)phenyl-5H-furan-2-one

Following the procedure described for Example 25, the title compound was prepared from 5-hydroxyisoquinoline.

$^1$H NMR($CD_3COCD_3$) d 1.80(6H, s), 3.10(3H, s), 7.38 (1H, d), 7.55(1H, t), 7.85(1H, d), 7.95(4H, m), 8.04(1H, d), 8.58(1H, d), 9.30(1H, s).

EXAMPLE 53

3-(6-Amino-2-pyridyloxy)-5,5-dimethyl-4-(4-(methylsulfonyl)phenyl)-5H-furan-2-one Following the procedure described for Example 25, the title compound was prepared from 2-hydroxy-6-aminopyridine.

M.P.: 165–166° C. $^1$H NMR ($CD_3COCD_3$) δ1.74 (6H, s), 3.14 (3H, s), 5.52 (2H, s, br), 6.17 (1H, d), 6.24 (1H, d), 7.41 (1H, t), 7.90 (2H, d), 8.02 (2H, d).

EXAMPLE 54

3-(3-Chloro-4-fluoro)phenoxy-4-(methylsulfonyl) phenyl)-5,5-dimethyl-5H-furan-2-one Following the procedure for Example 25, the title compound was prepared from 3-chloro-4-fluorophenol; m.p.: 130–132° C.

$^1$H NMR (CD$_3$COCD$_3$) δ1.76 (6H, s), 3.14 (3H, s), 7.10 (1H, m), 7.24 (1H, t, J=9 Hz), 7.30 (1H, m), 7.92 (2H, d, J=8.5 Hz), 8.03 (2H, d, J=8.5 Hz).

EXAMPLE 55

3-(6-Quinolinoxy)-5,5-dimethyl-4-(4-(methylsulfonyl)phenyl)-5H-furan-2-one

Following the procedure described for Example 25, the title compound was prepared using 6-hydroxyquinoline. M.P.: 171–172° C.

$^1$H NMR (CD$_3$COCD$_3$) δ1.82 (6H, s), 3.08 (3H, s), 7.46 (1H, m), 7.53–7.60 (3H, m), 7.95–8.01 (5H, m), 8.23 (1H, m), 8.80 (1H, m).

EXAMPLE 56

3-(5-Nitro-2-pyridyloxy)-5,5-dimethyl-4-(4-methylsulfonyl)phenyl-5H-furan-2-one

Following the procedure described for Example 25, the title compound was prepared from 2-hydroxy-5-nitropyridine.

$^1$H NMR (CD$_3$COCD$_3$) δ1.80(6H, s), 3.18(3H, s), 7.38 (1H, d), 7.92(2H, d), 8.05(2H, d), 8.66(1H, m), 9.05(1H, m).

EXAMPLE 57

3-(2-Thiazolylthio)-5,5-dimethyl-4-(4-(methylsulfonyl)phenyl)-5H-furan-2-one

Following the procedure described for Example 25, the title compound was prepared using 2-mercaptothiazole. M.P.: 174–176° C.

$^1$H NMR (CD$_3$COCD$_3$) δ1.67 (6H, s), 3.19 (3H, s), 7.59 (1H, d), 7.68 (1H, d), 7.74 (2H, d), 8.07 (2H, d).

EXAMPLE 58

3-(3-Fluoro-5-pyridyloxy)-5,5-dimethyl-4-(4-(methylsulfonyl)phenyl)-5H-furan-2-one Following the procedure described for Example 25, the title compound was prepared using 5-fluoro-2-hydroxypyridine M.P.: 157–159° C.

$^1$H NMR (CD$_3$COCD$_3$) δ1.76 (6H, s), 3.16 (3H, s), 7.16 (1H, m), 7.74 (1H, m), 7.92 (2H, d), 8.03 (2H, d), 8.07 (1H, m).

EXAMPLE 109a 5,5-Dimethyl-4-(4-methylsulfonylphenyl)-3-(2-propoxy)-5H-furan-2-one Step 1  5,5-Dimethyl-3-hydroxy-4-(4-methylsulfonylphenyl)-5H-furan-2-one To a 0° C. solution of the alcohol of Example 1, Step 3 (29.5 g, 122 mmol) in CH$_3$CN (350 mL) were added pyridine (25 mL) and acetoxyacetyl chloride (25 g, 183 mmol). After a period of 7h at r.t., DBU (31 mL) was added to the reaction mixture. After a period of 1h at 80° C., a second portion of DBU (35 mL) was added. The reaction mixture was kept at 80° C. for 18h. The reaction mixture was allowed to cool to r.t. The mixture was poured onto ice-water (2.5L) containing 100 mL of concentrated HCl. The brown solid was collected and dissolved in hot acetonitrile and was filtered through a plug of silica. The solvent was evaporated and the resultant solid was swished in EtOAc to give the title compound (21.2 g, 62%).

Step 2  5,5-Dimethyl-4-(4-methylsulfonyl)phenyl)-3-(-2-propoxy)-5H-furan-2-one

To a suspension of the alcohol of Step 1 (18.16 g, 64.4 mmol) in benzene (350 mL) were added an excess of 2-iodopropane (19.3 mL) and Ag$_2$CO$_3$ (53.3 g, 1.06 mmol). After stirring for 18h, the reaction mixture was filtered and the filtrate was washed with hot EtOAc. After evaporation, the crude compound was purified by flash chromatography (35% to 40% EtOAc/hexane, followed by addition of 5% CH$_2$Cl$_2$) to provide 19 g of the title compound.

$^1$H NMR (CD$_3$COCD$_3$) δ1.25 (6H, d), 1.70 (6H, s), 3.20(3H,s), 5.20(1H,septet), 8.05 (4H, s).

EXAMPLE 109b 5,5-Dimethyl-4-(4-methylsulfonylphenyl)-3-(2-propoxy)-5H-furan-2-one Step 1:  5,5-Dimethyl-3-hydroxy-4-(4-methylsulfonylphenyl)-5H-furan-2-one To a 0° C. solution of the alcohol of Example 1, Step 3 (14.0 g, 57.8 mmol) in CH$_3$CN (180 mL) were added pyridine (10.0 mL) and acetoxyacetyl chloride (12.7 g, 93.0 mmol) after a period of 7h at r.t., DBU (15.0 mL) was added to the reaction mixture. After a period of 1h at 80° C., a second portion of DBU (20.0 mL) was added. The reaction mixture was kept at 80° C. for 18h. The reaction mixture allowed to cool to r.t. The mixture was diluted with EtOAc (500 mL) and H$_2$O (500 mL) and acidified with 6NHCl. After the addition of brine (100 mL), the aqueous phase was extracted 2 times with EtOAc. The organic phase was evaporated to provide a brown residue. To the solid was added a 2:1 mixture of CH$_2$Cl$_2$-toluene (150 mL). The solid was filtered and washed with CH$_2$Cl$_2$-toluene to provide 7.0 g of the title compound.

Step 2  5,5-Dimethyl-4-(4-methylsulfonyl)phenyl)-3-(-2-propoxy)-5H-furan-2-one

To a suspension of the alcohol of Step 1 (100 mg, 0.354 mmol) in benzene (5.0 mL) were added an excess of 2-iodopropane (105 mL) and Ag$_2$CO$_3$ (294 mg, 1.06 mmol). After a period of 18h at 45° C., the reaction mixture was filtered over celite and washed with CH$_2$CL$_2$. After evaporation, the crude compound was purified by flash chromatography (35% to 40% EtOAc) to provide 70 mg of the title compound.

$^1$H NMR (CD$_3$COCD$_3$) δ1.25 (6H, d), 1.70 (6H, s), 3.20 (3H, s), 5.20 (1H, Septet), 8.05 (4H, s).

Alternatively compound 109 may be prepared in the following manner:

Step A1: 2-Methyl-1-(4-(thiomethyl)phenyl)propan-1-one

A 500 mL flask was charged under N$_2$ with 34.5 g (259 mMol) of AlCl$_3$ and 100 mL of ODCB. The vigorously stirred slurry was cooled to 8° C. and isobutyryl chloride (28.6 mL, 261 mMol) was added over 30 min., keeping the temperature at 10–15° C.

The addition of isobutyryl chloride was slightly exothermic.

The AlCl$_3$/isobutyryl chloride complex was aged at 7° C. for 30 min. Efficient cooling was applied and thoanisole (31.2 g) was added to the reaction mixture over 120 min., maintaining an internal temperature of 8–13° C.

The addition of thioanisole was very exothermic. After the addition of about half of thoanisole a heavy yellow precipitate formed. The precipitation was accompanied by an exotherm. Gaseous HCl is formed in the reaction, so that the effluent gas stream should be scrubbed with aqueous NaOH before release into the atmosphere.

The reaction was warmed to 16° C. over 1h.

The reaction mixture was a thick yellow slurry at this point. HPLC analysis of a quenched (EtOAc/H$_2$O) aliquot indicated completion of reaction.

The reaction mixture was cooled to 10° C. and 160 mL of 5% aqueous HCl were added over 45 min.

The addition was extremely exothermic and especially the initial addition required careful temperature monitoring.

The biphasic mixture was vigorously stirred for 60 min. The lower organic phase was removed.

A quantitative assay of the organic phase indicated a 98% yield.

Step A2: 2-Bromo-2-methyl-1-(4-(thiomethyl)phenyl) propan-1-one

A 500 mL flask was charged with the solution of the compound from step A1 (246 mMol). Approximately 10% of the bromine (1.3 mL, 26 mMol) were added and the reaction mixture was stirred until the red color had dissipated after 45 min. The remainder of the $Br_2$ (12 mL) was added over 60 min.

The reaction was exothermic and the temperature rose to ca. 32° C.

Gaseous HBr was released from the reaction, thus the effluent gas stream was scrubbed with aqueous NaOH before release into the atmosphere.

The reaction mixture was aged for 2 h at 30° C. when HPLC analysis indicated completion of the reaction Addition of a slight excess of $Br_2$ leads to the partial oxidation of the sulfide to the sulfoxide.

The reaction was quenched by the addition of 160 mL $H_2O$ and the resulting 182.0 mL of organic phase were used directly for the oxidation (next step) (95% assay yield).

Step A3: 2-Bromo-2-methyl-1-(4-(methylsulfonyl) phenyl)propan-1-one

To a solution of the compound from the previous step in ODCB in a 500 mL reaction vessel with heating jacket, reflux condenser and bottom valve was added under $N_2$ a solution of $Na_2WO_4$ (0.45 g, 1.4 mMol) and Aliquat 336 (2.2 g, 5.4 mMol) in 3.0 mL $H_2O$. The heterogeneous reaction mixture was heated with vigorous stirring to 35° C. and ca. 3.0 mL of $H_2O_2$ (30%) were added.

The oxidation was extremely exothermic. After an induction period of ca. 3 min. the temperature rose quickly to 55–65° C.

The remainder of the $H_2O_2$ (36 mL) was added over 1 h. At the end of the addition HPLC analysis indicated completion of the reaction.

The reaction mixture was heated to 80° C., the lower organic phase was removed and cooled to 6° C. over 1 h.

The product precipitated at ca. 50° C. without seeding.

The slurry was filtered and washed with 25.0 mL of ODCB and 30.0 mL of hexane and three times with 20.0 mL of 60° C. $H_2O$. After drying 37.8 g of the title compound (97% yield, ca. 91% overall yield from thioanisole) were obtained as a white powder.

Step A4: Isopropxyacetic acid

A 500 mL vessel fitted with a mechanical stirrer, thermocouple probe, and nitrogen inlet is charged with 200 mL of IPA (K.F. 200 µg/mL) and sodium hydroxide (6.0 g, 0.145 mol). The mixture was heated at reflux until the solid sodium hydroxide dissolved.

A homogeneous solution is obtained after reflux for 3 h.

The solution was cooled at ~70° C. and toluene (15.0 mL) was added. It was distilled until ~100 mL of distillate was collected. A mixture of IPA/toluene (85:15, 100 mL) was added and ~0.1 L of liquid was distilled off (repeated 3x). At the end of distillation (~0.4 L of distillate collected), the solution was diluted with IPA to a volume of ~300 mL.

The distillate is assayed to determine the amount of water removed. If the water removed is <75% of the theoretical amount (K.F. of IPA+that in NaOH+1 equiv generated), the distillation should be continued. The solution was then cooled at 60–70° C. and sodium chloroacetate (15.9 g, 0.134 mol) was added in portions over 5 min. No exotherm is observed during the addition.

The mixture was heated at reflux for 3 h and a sample of the slurry was taken for assay.

The reaction is followed by $^1$HNMR. An aliquot (~0.2 mL) of the mixture is taken and evaporated to dryness. The residue is dissolved in $D_2O$ for $^1$HNMR measurement. The reaction is considered completed when the starting material is <3% vs. product.

The reaction was quenched by addition of 60.0 mL of water and concentrated under reduced pressure (150–200 mBar, 50–60° C.) until ~250 mL of distillate was collected. More water was added (40.0 mL) and the solution was distilled at normal pressure until the batch temperature reached ~103° C. (~100 mL of solution left, ~300 mL of solvent removed). The solution was cooled at 10–20° C. and neutralized by addition of conc. hydrochloric acid (12.5 mL, 0.15 mol).

External cooling may be needed during the addition of acid. The final pH should be <2.3, preferably ~2.

t-Butyl methyl ether (80.0 mL) was added. The aqueous solution was saturated with sodium chloride (~9.0 g) and the two-phase mixture was agitated for 0.5 h at 10–15° C. The layers were separated and the aqueous layer was back extracted with 2×60.0 mL of t-butyl methyl ether. The organic layers were combined and washed with 2×10.0 mL of saturated aqueous sodium chloride.

The pH of the 2nd brine wash should be >2.5.

The organic solution was dried over 4A molecular sieves (10.0 g) for 14 h and filtered. The sieves were washed with 3×15.0 mL of t-butyl methyl ether. t-Butyl methyl ether was removed under reduced pressure (~200 mBar, 45–50° C.). Isopropoxyacetic acid was obtained as a slightly yellow liquid.

Yield: 11.8 g, 75% yield.

Step A5: 2-(isopropoxy)acetic acid 2-methyl-1-(4-methylsulfonyl)phenyl)propan-1-one-2-yl ester A 100 mL flash was sequentially charged with dry ethanol (45.0 mL, K.F. <100 µg/mL), isopropoxyacetic acid (2.32 g), diisopropylethylamine (4.85 mL) and the bromosulfone (step A3) (5.0 g). The mixture is heated to reflux until the bormosulfone is not detected (HPLC, reaction time 12–14 hours).

The reaction is considered complete when the bromosulfone is <0.05 A % vs. product.

After the reaction was complete, the solution was allowed to cool and seeded at 42° C. Crystallization initiated immediately and the mixture was cooled to 1° C. and aged 1 hr. The product ester is filtered and washed with ethanol (0° C. 5.0 mL wash). After drying in a vacuum oven, the white crystalline title compound was used as is in the next step.

Yield:4.15 g.

Step A6: 5,5-Dimethyl-4-(4-methylsulfonylphenyl)-3-(2-propoxy)-5H-furan-2-one

A 1 L flash was sequentially charged with dry acetonitrile (320 mL, K.F. <100 µg/mL), isopropyl trifluoroacetate (30.1 g, 0.193 mol), and DBU (36.70 g, 0.24 mol). The solution was stirred at ~20° C. for 15 min and the ester from Step A5 (55.0 g, 0.161 mol) was added. The solution was heated at reflux under nitrogen and the progress of the reaction was followed by HPLC.

The reaction is considered complete when the intermediate peaks are <0.2 A % vs. product.

After the reaction was complete, the solution was cooled at ~40° C. and filtered (1 µin-line capsule). The solution was then concentrated at 40–50°C. under reduced pressure unitl ~0.20 L of distillate was collected. Water (350 mL) was added slowly at ~45° C. After ~130 mL of water was added, the solution turned cloudy (40–45° C.) and ~0.02 g of crystalline title compound was added as the seed. The mixture was aged for 30 min and the remaining water was added. The mixture was aged at ~20° C. for 6 h then filtered. The cake was washed with 2×65 mL of 1:4 MeCN/water and 3×65 mL of water. The title product was air dried and dried in vacuo (35° C., 200 mBar).

Yield: ~48.0 g, 92%.

EXAMPLE 110

3-(3-Trifluoromethyl)phenoxy-4-(4-methylsulfonyl) phenyl)-5,5-dimethyl-5H-furan-2-one Following the procedure described for Example 25, the title compound was prepared from 3-trifluoromethylphenol.

$^1$H NMR (CD$_3$COCD$_3$) δ 1.79 (6 H s), 3.14 (3 H, s), 7.41 (3 H, m), 7.55 (1 H, m), 7.95 (2 H, dd, J=2, 6.6 Hz), 8.03 (2 H, dd, J=2, 6.7 Hz). Analysis calculated for C$_{20}$H$_{17}$F$_3$O$_5$S: C, 56.34; H, 4.02; Found: C, 56.21, H, 4.01.

EXAMPLE 111

5,5-dimethyl-4-(4-(methylsulfonyl)phenyl)-3-(piperidine-1-carbonyl)-5-H-furan-2-one Step 1 5,5-Dimethyl-4-(4-(methylsulfonyl)phenyl)-2-oxo-2,5-dihydrofuran-3-carboxylic acid ethyl ester A mixture of 2-hydroxy-2-methyl-1-(4-(methylsulfonyl) phenyl)propan-1-one (2.87 g, 11.8 mmol), ethyl hydrogen malonate (2.02 g, 15.3 mmol), CMC (6.51 g, 15.4 mmol) and DMAP (0.35 g, 2.8 mmol) was dissolved in 100 mL of CH$_2$Cl$_2$. The mixture was stirred for 14 h at room temperature, then DBU (4 mL, 27 mmol) was added, stirred 1 h, then partitioned between CH$_2$Cl$_2$ and 1M HCl. The organic layer was washed with brine, filtered through cotton an evaporated. Purification by flash chromatography (90% ether/Hex) provided 2.50 g of the title compound.

$^1$H NMR (CD$_3$COCD$_3$) δ 8.09 (2 H, m), 7.68 (2 H, m), 4.05 (2 H, q), 3.16 (3 H, s), 1.58 (6 H, s), 0.96 (3 H, t).

Step 2 5,5-Dimethyl-4-(4-(methylsulfonyl)phenyl)-3-(piperidine-1-carbonyl)-5H-furan-2-one To a room temperature solution of piperidine (284 mg, 3.33 mmol) in CH$_2$Cl$_2$ (5 mL) was added trimethylaluminum (2M in hexane, 1.7 mL, 3.4 mmol). After 15 min, the product from Step 1 (310 mg, 0.92 mmol) was added in one portion and the mixture was heated to reflux for 20 h. The resulting solution was cooled and poured into 1M HCl (gas evolution). The organic layer was washed with brine, filtered through cotton and evaporated. Purification by flash chromatography (80% EtOAc/Hex) provided 175 mg of the title compound.

$^1$H NMR (CD$_3$COCD$_3$) δ 8.08 (2 H, m), 7.80 (2 H, m), 3.49 (2 H, m), 3.35 (2 H, m), 3.17 (3 H, s), 1.65 (6 H, s), 1.55 (2 H, m), 1.40 (4 H, m).

EXAMPLE 112

5,5-Dimethyl-3-(2-butoxy)-4-(4-methylsulfonylphenyl)-5H-furan-2-one

Step 1 5,5-Dimethyl-3-(2-butoxy)-4-(4-methylsulfonyl) phenyl)-5H-furan-2one

To a suspension of the alcohol of Example 109, Step 1 (300 mg, 1.06 mmol) in benzene (20.0 mL) were added 2-iodobutane (300 μL) and Ag$_2$CO$_3$ (400 mg, 3.27 mmol). After a period of 4 h at 45° C., the reaction mixture was filtered over celite and washed with CH$_2$Cl$_2$. After evaporation, the crude product was purified by flash chromatography (35% EtOAc in Hexane) to give 150 mg of the title compound as a white solid.

$^1$H NMR (CD$_3$COCD$_3$) δ 0.09 (3 H, t), 1.20 (3 H, d), 1.65 (6 H, s), 3.20 (3 H, s), 5.00 (1 H, m), 8.00 (4 H, s).

EXAMPLE 113

5,5-Dimethyl-4-(4-methylsulfonylphenyl)-3-(3-pentoxy)-5H-furan-2-one

Step 1 Pentyl-3-oxyacetic acid

To a solution of 3-pentanol (17.6 g, 200 mmol) in benzene (200 mL) was added NaH (6.0 g, 400 mmol). After 1 h at r.t., chloroacetic acid sodium salt (25.6 g, 200 mmol) was added to the previous mixture. After a period of 2 hr. at reflux, the reaction mixture was poured in H$_2$O and acidified with HCl. The mixture was extracted with CH$_2$Cl$_2$, dried over MgSO$_4$, filtered over silicic acid (30% EOAc in Hexane). After evaporation of the solvents the title compound was purified by distillation (5.0 g).

Step 2 Pentyl-3-oxyacetic acid 2-methyl-1-(4-methylsulfonylphenyl)propan-1-one-yl-ester The title compound was obtained using similar protocol as described for Example 1 Step 3.

Step 3 5,5-Dimethyl-4-(4-methylsulfonylphenyl)-3-(3-pentylxy)-5H-furan-2-one

To a solution of the ester of Step 2 (500 mg, 1.35 mmol) in DMF (2.5 mL) was added NaH (50 mg, 1.6 mmol). The reaction mixture was heated gently to give an orange mixture. After standard extractive workup procedure (EtOAc), the crude mixture was purified by flash chromatography (35% EtOAc in hexane to afford 115 mg of the title compound by filtration in Et$_2$O/hexane.

$^1$H NMR (CD$_3$COCD$_3$) δ 0.85 (6 H, t), 1.60 (4 H, m), 1.65 (6 H, s), 3.20 (3 H, s), 4.90 (1 H, quintet), 8.05 (4 H, s).

EXAMPLE 115

2-(5-Chloro-2-pyridinoxy)-3-(4-methylsulfonylphenyl)-cyclopent-2-enone

Using similar protocol described for Example 29 but using 1-(5-chloropyridyl-2-oxy)but-3-en-2-one the title compound was obtained.

$^1$H NMR (CD$_3$COCD$_3$) δ 2.50 (2 H, t), 2.80 (3 H, s), 3.10 (2 H, t), 7.10 (1 H, d), 7.30 (2 H, d), 7.80 (2 H, d), 7.85 (1 H, dd), 8.05 (1 H, d).

EXAMPLE 116

3-(4-Methyl-2-pyridyloxy)-5,5-dimethyl-4-(4-methylsulfonyl)phenyl-5H-furan-2-one Following the procedure described for Example 25, the title compound was prepared from 2-hydroxy-4-methylpyridine.

$^1$H NMR (CD$_3$COCD$_3$) δ 1.76 (6 H, s), 2.36 (3 H, s), 3.15 (3 H, s), 6.90 (1 H, s), 6.98 (1 H, d), 7.89 (2 H, d), 7.98 (1 H, d), 8.02 (2 H, d).

EXAMPLE 117

(5R)-3-(3,4-Difluorophenoxy)-5-ethyl-5-methyl-4-(4-methylsulfonyl)phenyl-5H-furan-2-one Step 1: 2-(S)-t-butyl-5-(R)-ethyl-4-hydroxy-5-methyl-4-(4-(methylthio)phenyl)-1,3-dioxolan-4-one To a solution of 4-bromothioanisole (27.3 g, 134 mmol) in 300 ml of anhydrous THF at −72° C. was added 2.5 M n-BuLi in hexanes (54 ml, 135 mmol) at such a rate as to maintain the internal temperature below −55° C. and the mixture was stirred at −72° C. for an hour. A solution of 2-(S)-t-butyl-5-(R)-ethyl-5-methyl-1,3-dioxolan-4-one (16.8 g, 90 mmol, *Tetrahedron,* 1894, 40, 1313) in 50 ml of THF was added dropwise and the mixture was stirred at −72° C. for 15 minutes. Acetic acid (13 ml) was then added slowly and the mixture stirred for another 10 min. at −72° C. The reaction was quenched with 25% aq. NH$_4$OAc at −72°

C. and allowed to warm up to r.t. the title product was extracted in i-PrOAc, dried over $Na_2SO_4$ and purified by flash chromatography on silica with EtOAc/hexane 2.5 and 5% to yield 22.4 g (80%) of a white solid.

$^1$H NMR ($CDCl_3$, mixture of 2 diastereoisomers 1.8:1) d 0.58, 1.52, 1.68 and 2.05 (2 H, 4 m), 0.70 and 1.36 (3 H, 2 s), 0.73 and 0.98 (3 H, 2 T), 1.00 (9 H, 2 s), 2.47 (3 H, 2 s), 2.47 and 2.57 (1 H, 2 s,)H), 4.80 and 5.00 (1 H, 2 s), 7.20 (2 H, 2 d), 7.45 (2 H, 2 d).

Step 2: 2-(R)-hydroxy-2-methyl-1-(4-(methylthio)phenyl)-1-butanone

A mixture of the product of step 1 (32.0 g, 103 mmol), p-toluenesulfonic acid (900 mg) and 35 ml of water was heated to reflux for an hour. The title product was extracted in 200 mL of EtOAc and the solution used as such in the next step.

Step 3: 2-(R)-hydroxy-2-methyl-1-(4-(methylsulfonyl)phenyl)-1-butanone-1-one

To the product of Step 2 in 200 ml of EtOAc in an ice bath (to maintain the temperature of the reaction below 25° C.) was added 100 ml of t-BuOH, 2.3 g of Aliquat 336® and a solution of 73.1 g of Oxone® (238 mmol $KHSO_5$) in 450 ml of water and the mixture was stirred at r.t. overnight. It was then neutralized with 10N NaOH. The title product was extracted in i-PrOAc, dried over $Na_2SO_4$, and purified by flash chromatography on silica with EtOAc/toluene 20 & 40% to yield 23.8 g of a colorless oil. NMR experiments with the chiral shift reagent Eu (hfc)$_3$ indicated an enantiomeric excess superior than 94%. $[\alpha]_D^{25}=-11.2°$ (c=0.8, $CHCl_3$).

$^1$H NMR ($CDCl_3$) δ 0.87 (3 H, t), 1.57 (3H, s), 1.93 (2 H, m), 3.07 (3 H, s), 3.53 (1 H, s), 8.00 (2 H, d), 8.13 (2 H, d).

Step 4: (5R)-3-(3,4-Difluorophenoxy)-5-ethyl-5-methyl-4-(4-methylsulfonyl)phenyl-5H-furan-2-one Following the procedure described for Example 1, step 4, the title compound was prepared from 3,4-difluorophenoxyacetic acid and (2R)-2-hydroxy-2-methyl-1-(4-methylsulfonyl)phenyl-butan-1-one. $[\alpha]_D=+9.4°$ (c 0.9, acetone).

$^1$H NMR ($CD_3COCD_3$) δ 0.95 (3 H, t), 1.80 (3 H, s), 2.12 (2 H, q), 3.18 (3 H, s), 6.95 (1 H, m), 7.14 (1 H, m), 7.30 (1 H, m), 7.95 (2 H, d), 8.06 (2 H, d).

EXAMPLE 118

(5R)-3-(4-Chlorophenoxy)-5-ethyl-5-methyl-4-(4-methylsulfonyl)phenyl-5H-furan-2-one Following the procedure described for Example 117, the title compound was prepared from 4-chlorophenoxyacetic acid and (2R)-2-hydroxy-2-methyl-1-(4-methylsulfonyl)phenyl-butan-1-one.

$^1$H NMR ($CD_3COCD_3$) δ 0.93 (3 H, t), 1.78 (3 H, s), 2.12 (2 H, q), 3.15 (3 H, s), 7.11 (2 H, d), 7.35 (2 H, d), 7.92 (2 H, d), 8.03 (2 H, d).

EXAMPLE 119

3-(2-Methyl-3-pyridyloxy)-5,5-dimethyl-4-(4-methylsulfonyl)phenyl-5H-furan-2-one Following the procedure described for Example 25, the title compound was prepared from 3-hydroxy-2-methylpyridine.

$^1$H NMR ($CD_3COCD_3$) δ 1.77 (6 H, s), 2.48 (3 H, s), 3.14 (3 H, s), 7.08 (1 H, m), 7.33 (1 H, d), 7.93 (2 H, d), 8.02 (2 H, d), 8.16 (1 H, m).

EXAMPLE 120

3-(4-Methyl-5-nitro-2-pyridyloxy)-5,5-dimethyl-4-(4-methylsulfonyl)-phenyl-5H-furan-2-one A mixture of 3-hydroxy-5,5-dimethyl-4-(4-methylsulfonyl)phenyl-5H-furan-2-one (1.5 g, 5.3 mmol, Example 109 step 1), 2-chloro-4-methyl-5-nitropyridine (1.0 g, 5.8 mmol) and powdered KOH (300 mg, 5.4 mmol) in DMF (20 mL) was heated at 100° C. for 12 h. After cooling to r.t., the mixture was diluted with $H_2O$, extracted with EtOAc. The EtOAc extract was washed with brine, dried (anhydrous $MgSO_4$) and concentrated in vacuo. The residue was swished with EtOH to give the title compound as a pale yellow solid (1.7 g, 77%).

$^1$H NMR ($CD_3COCD_3$) δ 1.80 (6 H, s), 2.68 (3 H, s), 3.16 (3 H, s), 7.20 (1 H, s), 7.90 (2 H, d), 8.05 (2 H, d), 8.85 (1 H, s).

EXAMPLE 121

3-(5-Chloro-4-methyl-2-pyridyloxy)-5,5-dimethyl-4-(4-methylsulfonyl)-phenyl-5H-furan-2-one Step 1: 3-(5-Amino-4-methyl-2-pyridyloxy)-5,5-dimethyl-4-(4-methylsulfonyl)phenyl-5H-furan-2-one A mixture of 3-(4-methyl-5-nitro-2-pyridyloxy)-5,5-dimethyl-4-(4-methylsulfonyl)phenyl-5H-furan-2one (1.4 g, 3.3 mmol), iron powder (1.5 g, 27 mmol) and $NH_4Cl$ (150 mg) in 67% aqueous EtOH (45 mL) was refluxed for 1 h. The hot mixture was filtered through celite. Volatile solvent was evaporated in vacuo. The residue was suspended in water, filtered and dried under vacuum to give the title compound as a brown powder (1.2 g, 94%).

$^1$H NMR ($CD_3COCD_3$) δ 1.72 (6 H, s), 2.20 (3 H, s), 3.15 (3 H, s), 4.42 (2 H, brs), 675 (1 H, s), 7.50 (1 H, s), 7.90 (2 H, d), 8.00 (2 H, d).

Step 2: 3-(5-Chloro-4-methyl-2-pyridyloxy)-5,5-dimethyl-4-(4-methylsulfonyl)phenyl-5H-furan-2-one To a suspension of 3-(5-amino-4-methyl-2-pyridyloxy)-5,5-dimethyl-4-(4-methylsulfonyl)phenyl-5H-furan-2-one (600 mg, 1.6 mmol) in 6M aqueous HCl (3 mL) at 0° C. was added dropwise a solution of 4M aqueous $NaNO_2$ (450 mL, 1.8 mmol). The solution became clear and then precipitate formed. After stirring for 30 min, the diazotization mixture was added to a solution of CuCl (300 mg, 3.0 mmol) in concentrated HCl (2 mL) at 0° C., then heated to 70–80° C. for 10 min, cooled to r.t. and diluted with $H_2O$ and dried under vacuum. Recrystallization from EtOH-Acetone yielded the title compound as a light yellow solid (360 mg, 57%).

$^1$H NMR ($CD_3COCD_3$) δ 1.76 (6 H, s), 2.40 (3 H, s), 3.16 (3 H, s), 7.10 (1 H, s), 7.90 (2 H, d), 8.05 (2 H, d), 8.10 (1 H, s).

EXAMPLE 122

3-(5-Fluoro-4-methyl-2-pyridyloxy)-5,5-dimethyl-4-(4-methylsulfonyl)phenyl-5H-furan-2-one To a suspension of 3-(5-amino-4-methyl-2pyridyloxy)-5,5-dimethyl-4-(4-methylsulfonyl)phenyl-5H-furan-2-one (650 mg, 1.68 mmol, Example 121 step 1) in 6M aqueous HCl (4 mL) at 0° C. was added dropwise a solution of 4M aqueous $NaNO_2$ (450 mL, 1.8 mmol). After stirring at 0° C. for 30 min, 60% aqueous $HPF_6$ (2 mL) was added and the mixture was further stirred for 30 min. The precipitate was collected, washed with $H_2O$ and dried under vacuum to give 850 mg of diazonium salt.

The diazonium salt was then heated with a propane torch until the compound started to decompose. The dark brown residue was dissolved in acetone and chromatographed over silica gel, eluted with hexanes:EtAOc (2:3) to provide the title compound as a pale yellow solid (100 mg, 17%).

$^1$H NMR ($CD_3COCD_3$) δ 1.72 (6 H, s), 2.34 (3 H, s), 3.16 (3 H, s), 7.02 (1 H, m), 7.90 (2 H, d), 7.94 (1 H, s), 8.02 (2 H, d).

EXAMPLE 123

3-(3-Chloro-2-pyridyloxy)-5,5-dimethyl-4-(4-methylsulfonyl)phenyl-5H-furan-2-one Step 1: 3-(3-Nitro-2-pyridyloxy)-5,5-dimethyl-4-(4-methylsulfonyl)phenyl-5H-furan-2one A mixture of 3-hydroxy-5,5-dimethyl-4-(4-methylsulfonyl)phenyl-5H-furan-2-one (1.5 g, 5.3 mmol), 2-chloro-3-nitropyridine (1.0 g, 6.3 mmol) and powdered KOH (320 mg, 5.7 mmol) in DMF (20 mL) was heated at 100° C. for 12 h. After cooling to r.t., the mixture was diluted with H$_2$O, extracted with EtOAc. The EtOAc extract was washed with brine, dried (anhydrous MgSO$_4$) and concentrated in vacuo. chromatorgraphy over silica gel and elution with hexanes:EtOAc (1:1) gave a solid residue. The residue was swished with EtOH to provide 1.6 g (73%) of title compound.

$^1$H NMR (CD$_3$COCD$_3$) δ 1.82 (6 H, s), 3.18 (3 H, s), 7.50 (1 H, m), 8.00 (4 H, m), 8.50 (1 H, m), 8.60 (1 H, d).

Step 2: 3-(3-Amino-2-pyridyloxy)-5,5-dimethyl-4-(4-methylsulfonyl)phenyl-5H-furan-2-one A mixture of 3-(4-methyl-4-nitro-2-pyridyloxy)-5,5-dimethyl-4-(4-methylsulfonyl)phenyl-5H-furan-2-one (1.5 g, 3.7 mmol), iron powder (1.5 g, 27 mmol) and NH4Cl (150 mg) in 67% aqueous EtOH (45 mL) was refluxed for 1 h. The hot mixture was filtered through celite. Volatile solvent was evaporated in vacuo. The residue was suspended in water, filtered and dried under vacuum to give the title compound as a brown powder (1.4 g, quantitative).

$^1$H NMR (CD$_3$COCD$_3$) δ 1.76 (6 H, s), 3.18 (3 H, s), 4.88 (2 H, brs), 6.86 (1 H, m), 7.10 (1 H, m), 7.35 (1 H, m), 7.98 (4 H, m).

Step 3: 3-(3-Chloro-2-pyridyloxy)-5,5-dimethyl-4-(4-methylsulfonyl)phenyl-5H-furan-2-one To a suspension of 3-(3-amino-2-pyridyloxy)-5,5-dimethyl-4-(4-methylsulfonyl)phenyl-5H-furan-2-one (700 mg, 1.7 mmol) in 6M aqueous HCl (3 mL) at 0° C. was added dropwise a solution of 4M aqueous NaNO$_2$ (500 mL, 2.0 mmol). After stirring for 30 min, the diazotization mixture was added to a solution of CuCl (400 mg, 4.0 mmol) in concentrated HCl (2 mL) at 0° C., then heated to 70–80° C. for 10 min, cooled to r.t., diluted with H$_2$O and extracted with EtOAc. Chromatography over silica gel and elution with hexanes:EtOAc (1:1) to give a solid residue (100 mg). Recrystallization from EtOH provided the pure title compound (90 mg, 13%).

$^1$H NMR (CD$_3$COCD$_3$) δ 1.80 (6 H, s), 3.16 (3 H, s), 7.20 (1 H, m), 7.94 (2 H, d), 7.98 (1 H, m), 8.05 (2 H, d), 8.10 (1 H, m).

EXAMPLE 124

3-(4-Fluorophenoxy)-5-methyl-4-4-methylsulfonyl)phenyl-5-propyl-5H-furan-2-one

Following the procedure described for Example 25, the title compound was prepared from 2-hydroxy-2-methyl-1-(4-methylsulfonyl)phenyl-1-pentanone and 4-fluorophenol.

$^1$H NMR (CD$_3$COCD$_3$) δ 0.94 (3 H, t), 1.38 (2 H, m), 1.78 (3 H, s), 2.05 (2 H, m) 3.14 (3 H, s), 7.08 (4 H, m), 7.92 (2 H, d), 8.02 (2 H, d).

EXAMPLE 125

3-(Diethylamino)-5,5-dimethyl-4-(4-(methylsulfonyl)phenyl)-5H-furan-2-one

Step 1
2-(diethylamino)acetic acid 2-methyl-2-(4-(methylsulfonyl)phenyl)propan-1-one-2-yl ester To a room temperature solution of 2-chloroacetic acid 2-methyl-1-(4-methylsulfonyl)phenyl)propan-1-one-2-yl ester (2.00 g, 6.27 mmol) in acetonitrile (10 mL) was added diethyl amine (1.62 mL, 15.7 mmol). The resulting solution was heated to 60° C. for 16 hours. The reaction mixture was cooled to room temperature and partitioned between dichloromethane and water. The organic layer was separated, washed with brine, filtered through cotton and the solvent was evaporated under vacuum. Purification by silica gel chromatography (80% EtOAC/Hex.) provided 1.70 g of the title compound.

$^1$H NMR (CD$_3$COCD$_3$) δ 0.85 (6H,t), 1.70 (6H,s), 2.37 (4H,q), 3.15 (3H,s) 3.27 (2H,s), 8.00–8.07 (2H,m), 8.15–8.22 (2H,m).

Step 2
3-(Diethylamino)-5,5-dimethyl-4-(4-(methylsulfonyl)phenyl)-5H-furan-2-one Sodium hydride, 60% dispersion (0.478 g, 11.96 mmol) was washed in hexane and suspended in DMF (5 mL). This suspension was added to a 0° C. solution of 2-(diethylamino) acetic acid 2-methyl-1-(4-(methylsulfonyl)phenyl)propan-1-one-2-yl ester (1.70 g, 4.78 mmol) in DMF (20 mL). The resulting mixture was warmed to RT for 15 minutes. The mixture was diluted with ethyl acetate and quenched with water. The organic layer was washed with brine, dried over MgSO$_4$ and concentrated to dryness. The residue was purified by swishing in ether/hexanes to give 500 mg of crystalline solid on filtration.

$^1$H NMR (CD$_3$COCD$_3$) δ 0.95 (6H,t), 1.45 (6H,s), 3.07 (4H,q), 3.17 (3H,s), 7.65–7.70 (2H,m), 7.97–8.05 (2H,m).

EXAMPLE 127

5,5-dimethyl-4-(4-methylsulfonyl-phenyl)-3-(3,5-dichloro-pyridin-2-yloxy)-5H-furan-2-one To a R.T. solution of 2-chloroacetic acid 2-methyl-1-(4-(methylsulfonyl)phenyl)propan-1-one ester (954 mg, 3 mmol, example 25) in acetonitrile (15 mL) was added 3,5-dichloro-2-pyridone (656 mg, 4.0 mmol) followed by DBU (2.28 g, 15 mmol) and the mixture was slowly warmed up to gentle reflux for 2 hours. The mixture was cooled to 25° C. the volatiles were removed in vacuo. The residue was purified on silica gel chromatography (1/1, EtOAc/Hexanes then 100% EtOAc)) to provide the title compound.

Analysis calculated for C$_{18}$H$_{15}$Cl$_2$NO$_5$S; C, 50.48; H, 3.53; N, 3.27. Found: C, 50.53; H, 3.49; N, 3.21.

EXAMPLE 128

(5R)-3-(4-Bromophenoxy)-5-ethyl-5-methyl-4-(4-methylsulfonyl)phenyl-5H-furan-2-one Following the procedure described for Example 117, the title compound was prepared from 4-bromophenoxyacetic acid and (2R)-2-hydroxy-2-methyl-1-(4-methylsulfonyl) phenylbutan-1-one.

$^1$H NMR (CD$_3$COCD$_3$) δ 0.93 (3H,t), 1.78 (3H,s), 2.12 (2H,q), 3.15 (3H,s), 7.05 (2H,d), 7.50 (2H,d), 7.94 (2H,d), 8.05 (2H,d).

EXAMPLE 129

(5R)-3-(4-Methoxyphenoxy)-5-ethyl-5-methyl-4-(4-methylsulfonyl)phenyl-5H-furan-2-one Following the procedure described for Example 25, the title compound was prepared from (2R)-2-chloroacetoxy-2-methyl-1-(4 -methylsulfonyl)phenylbutan-1-one (prepared similarly to the compound of Example 5 step 1) and 4-methoxyphenol.

$^1$H NMR (CD$_3$COCD$_3$) δ 0.92 (3H,t), 1.75 (3H,s), 2.08 (2H,q), 3.14 (3H,s), 3.74 (3H,s), 6.83 (2H,d), 6.97 (2H,d), 7.89 (2H,d), 7.99 (2H,d).

EXAMPLE 130

(5R)-3-(5-Chloro-2-pyridyloxy)-5-methyl-4-(4-methylsulfonyl)phenyl-5-(2,2,2-trifluoroethyl)-5H-furan-2-one Step 1
2-(S)-t-butyl-5-(R)-methyl-5-(2,2,2-trifluoroethyl)-1,3-dioxolan-4-one To a solution of lithium diiospropylamide (prepared from 13 ml of diisopropylamine and 54 ml of 1.6 M n-BuLi in hexanes in 200 ml of anhydrous THF at 0° C.) at −72° C. was added slowly 2-(s)-t-butyl-5-(s)-methyl-1,3-dioxolan-4-one (12.95 g, 81.9 mmol, Tetrahedron, 1984, 40, 1313) at such a rate as to maintain the internal temperature below −60° C. and the mixture was aged at −72° C. for an hour. 1,1,1-Trifluoro-2-iodoethane (25 g, 119 mmol) was added quickly, the reaction temperature increased to −45° C. and the mixture was aged at −72° C. for 45 min. and then allowed to warm up to −20° C. over 20 min. Saturated aq. $NH_4Cl$ was then added and the product was extracted in i-PrOAc, dried over $Na_2SO_4$, concentrated and distilled under reduced pressure to afford 7.51 g of a brown oil BP 90° C./20 mm Hg.

$^1$H NMR (CDCl$_3$, mixture of distereoisomers 3.2:1) d 0.97 (9H, 2s), 1.50 and 1.54 (3H, 2s), 2.59 (2H,m), 5.22 (1H, 2d).

Step 2
2-(R)-hydroxy-2-methyl-1-(4-(methylsulfonyl)phenyl-4,4,4-trifluoro-1-butanone Using the procedures of Example 117 step 1, 2 and 3, the product of Step 1 was converted to the title compound.

$^1$H NMR (CDCl$_3$) δ 1.68 (3H,s), 2.72 (1H,m), 2.98 (1H,m), 3.08 (3H,s), 3.35 (1H, br s, OH), 8.03 (2H,d), 8.14 (1H,d).

Step 3
(2R)-2-Chloroacetoxy-2-methyl-1-(4-methylsulfonyl)phenyl-4,4,4-trifluoro-butan-1-one A mixture of (2R)-2-hydroxy-2-methyl-1-(4-methylsulfonyl)phenyl-4,4,4-trifluoro-1-butanone (5.2 g, 16.8 mmol), chloroacetic acid (2.0 g, 21 mmol), CMC (9.5 g, 22 mmol) and DMAP (100 mg) in CH$_2$Cl$_2$ (50 mL) was stirred at r.t. for 2 h. TLC showed the esterification completed. The mixture was washed with H$_2$O (2×), dried (anhydrous MgSO$_4$) and concentrated in vacuo. Chromatography over silica gel and elution with hexanes:EtOAc (1:1) gave 6.0 g (92%) of the title compound as an oil.

$^1$H NMR (CD$_3$COCD$_3$) δ 1.98 (3H,s), 3.18 (3H,s), 3.28 (2H,m), 4.35 (2H,m), 8.08 (2H,d), 8.28 (2H,d).

Step 4
(5R)-3-(5-Chloro-2-pyridyloxy)-5-methyl-4-(4-methylsulfonyl)phenyl-5-(2,2,2-trifluoroethyl)-5H-furan-2-one Following the procedure described for Example 25, the title compound was prepared from (2R)-2-chloroacetoxy-2-methyl-1-(4-methylsulfonyl)phenyl-4,4,4-trifluoro-butan-1-one and 5-chloro-2-pyridinol.

$^1$H NMR (CD$_3$COCD$_3$) δ 1.94 (3H,s), 3.16 (3H,s), 3.24 (2H,q), 7.20 (1H,d), 7.95 (1H,m), 7.98 (2H,d), 8.04 (2H,d), 8.16 (1H,m).

EXAMPLE 133

3-(5-Chloro-2-pyridyloxy)-5-methyl-4-(4-methylsulfonyl)phenyl-5-propyl-5H-furan-2-one Following the procedure described for Example 25, the title compound was prepared from 2-chloroacetoxy-2-methyl-1-(4-methylsulfonyl)phenyl-1-pentanone (prepared in a fashion similar to that of the compound in example 1 step 1, 2 and 3) and 5-chloro-2-pyridinol.

$^1$H NMR (CD$_3$COCD$_3$) δ 0.93 (3H,t), 1.42 (2H,m), 1.76 (3H,s), 2.05 (2H,m) 3.15 (3H,s), 7.16 (1H,d), 7.90 (3H,m), 8.02 (2H,d), 8.16 (1H,m).

EXAMPLE 134

3-(1-Cyclopropyl-ethoxy)-5,5-dimethyl-4-(4-methylsulfonyl)phenyl)-5H-furan-2-one Step 1
(1-cyclopropyl-ethoxy)acetic acid To a suspension of NaH (80% in oil) (15.7 g, 523 mmol) in THF (180 mL) at 0° C. were added bromoacetic acid (28.0 g, 203 mmol) and a-methylcyclopropane methanol (10.0 g, 116 mmol). The resulting mixture was then stirred at 70° C. After a period of 18 h, the reaction mixture was poured over cold H$_2$O and the H$_2$O phase was extracted once with Et$_2$O. The water phase was acidified with HCl and extracted twice with Et$_2$O. The ether was dried over MgSO$_4$, filtered and evaporated under reduced pressure. The crude oil was then purified by flash chromatography (40% EtOAc in hexane to 40% EtOAc in Hexane+AcOH) to provide 5.0 g of the title compound.

Step 2
2-(1-Cyclopropylethoxy)acetic acid 2-methyl-1-(4-methylsulfonyl)phenyl)propan-1-one-2-yl ester A mixture of (1-cyclopropyl)-ethoxy) acetic acid (1.0 g, 6.90 mmol; Example 134, Step 1) 2-hydroxy-2-methyl-1-(4-(methylsulfonyl)phenyl)propan-1-one (1.37 g, 5.76 mmol; Example 1, Step 3), CMC (8.90 g, 20.8 mmol) and DMAP (100 mg, 0.820 mmol) in CH$_2$Cl$_2$ (100 ml) was left at r.t. for a period of 18 h. The resulting mixture was partitioned between NH$_4$OAc (20%) and CH$_2$Cl$_2$. The organic phase was dried over MgSO$_4$, filtered and evaporated under reduced pressure. The resulting mixture was purified by flash chromatography (35% EtOAc in hexane) to provide 590 mg of the title compound.

Step 3
3-(1-Cyclopropylethoxy)-5,5-dimethyl-4-(4-methylsulfonyl)phenyl)-5H-furan-2-one To a solution of 2-(1-cyclopropyl-ethoxy)acetic acid 2-methyl-1-(4-(methylsulfonyl)phenyl)propan-1-one-2yl ester (590 mg, 1.60 mmol; Example 134, Step 2) CH$_3$CN (20 mL) were added isopropyl trifluoro acetate (294 mL, 2.07 mmol) and DBU (782 mg, 5.14 mmol). After a period of 18 h at 70° C. The reacting mixture was evaporated under reduced pressure and purified by flash chromatography (30% EtOAc in toluene) to provide 270 mg of the title compound.

$^1$H NMR (CD$_3$COCD$_3$) δ 0.20 to 0.50 (5H,m), 0.90 (1H,m), 1.35 (3H,d), 1.65 (6H,s), 3.20 (3H,s), 4.35 (1H, quintet), 8.10 (4H,m).

EXAMPLE 136

5-Methyl-4-(4-(methylsulfonyl)phenyl)-3-(2-(propoxy)-5-(2,2,2-trifluoroethyl)-5H-furan-2-one Following the procedure described for Example 109, using 2-hydroxy-2-methyl-1-(4-(methylsulfonyl)phenyl)-4-trifluorobutan-1-one the title compound was obtained.

Step 2
3-hydroxy-5-methyl-4-(4-(methylsulfonyl)phenyl-5-(2-trifluoroethyl)-5H-furan-2-one $^1$H NMR (CD$_3$COCD$_3$) δ 1.30 (6H, 2d), 1.80 (3H,s), 3.15 (3H,s), 3.15 to 3.40 (2H,m), 5.30 (1H, quintet), 8.10 (4H,m).

EXAMPLE 140

5(R)-5-ethyl-5-methyl-4-(4-(methylsulfonyl)phenyl-3-(2-propoxy)-5H-furan-2-one

The title compound was prepared as described in Example 109, Step 2 using (5R)-5-ethyl-3-hydroxy-5-methyl-4-(4- methylsulfonyl)phenyl-5H-furan-2-one, which was prepared from the compound of Example 117, Step 3 following the procedure of Example 109, Step 1.

$^1$H NMR (CD$_3$COCD$_3$) δ 0.80 (6H, 2d), 1.60 (3H,s), 2.00 (2H,m), 3.15 (3H,s), 5.20 (1H, quintet), 8.00 (4H,s).

EXAMPLE 141

5,5-Dimethyl-3-(2,2-dimethylpropyloxy)-4-(4-(methylsulfonyl)phenyl)-5H-furan-2-one To a mixture of 5,5-dimethyl-3-hydroxy-4-(4-(methylsulfonyl)phenyl-5H-furan-2-one (500 mg, 1.77 mmol, Example 109, Step 1) in DMF (6 mL) were added NaH (65 mg, 1.2 eq.), and neopentyl iodide (585 μL). After a period of 18 h at 70° C., the reaction mixture was diluted with EtOAc. The mixture was washed with H$_2$O and the organic phase separated, dried over MgSO$_4$ and evaporated under reduced pressure. The resulting oil was purified by flash chromatography to provide the title compound (124 mg) as a white solid after precipitation with Et$_2$O.

$^1$H NMR (CD$_3$COCD$_3$) δ 0.95 (9H,s), 1.65 (6H,s), 3.15 (3H,s), 4.00 (2H,s), 8.00 (4H,m).

EXAMPLE 143

5(R) 3-(1-cyclopropyl-ethoxy)-5-ethyl-5-methyl-4-(4-(methylsulfonyl)phenyl-5H-furan-2-one Step 1
(1-cyclopropylethoxy)acetic acid 2(R)-methyl-1-(4-(methylsulfonyl)phenyl)butan-1-one-2yl ester The title compound was prepared as described in Example 134 Step 2 using (1-cyclopropylethoxy)acetic acid and 2(R) 2-hydroxy-2-methyl-1-(4-(methylsulfonyl)phenyl)butan-1-one from Example 117, Step 3.

Step 2
5(R) 3-(1-cyclopropylethoxy)-5-ethyl-5-methyl-4(4-(methylsulfonyl)phenyl-5H-furan-2-one The title compound was prepared as described in Example 134 Step 3.

$^1$H NMR (CD$_3$COCD$_3$) δ 0.1–0.4 (4H,m), 0.75 (2H,m), 1.00 (1H,m), 1.40 (3H,dd), 1.70 (3H,s), 2.05 (2H,m), 3.20 (3H,s), 4.50 (1H,m), 8.05 (m,4H).

EXAMPLE 144

5(S) 5-Ethyl-5-methyl-4-(4-(methylsulfonyl)phenyl-3-(2-propoxy)-5H-furan-2-one

Step 1
(±) 2-Methyl-1-(4-methylsulfonylphenyl)-prop-2-en-1-ol

To a solution of 4-bromothioanisole (51 g) in THF (600 mL) cooled to −72° C. was added dropwise a solution of n-BuLi (120 mL, 2.4 M in hexane) over a period of 30 min. The mixture was stirred at −78° C. for 2 h and then a solution of methacrolein (20.3 g) in THF (50 mL) was added over a period of 5 min. The reaction mixture was warmed to −20° C. over a period of 20 min. and then quenched with saturated NH$_4$Cl (200 mL) and H$_2$O (200 mL). The product was extracted with 500 mL of 1:1 hexane/EtOAc, and dried over MgSO$_4$. The extract was filtered and concentrated to give the title compound as a yellow oil (55 g).

Step 2
(±) 2-Methyl-1-(4-methylsulfonylphenyl)-prop-2-en-1-ol

To a solution of the product from Step 1 (55 g., crude) in MeOH (1 L) cooled to 0° C. was added a solution of Oxone® (190 g in 700 mL H$_2$O) over a period of 2 h. The mixture was stirred at 5° C. for an additional 3 h and then filtered. The filtrate was concentrated to remove MeOH and the remaining aqueous mixture was extracted with 1 L of 2:1 EtOAc/hexane. The extract was dried over MgSO$_4$ filtered and concentrated. The residue was purified by silica gel chromatography eluted with 3:2 hexane/EtOAc to give the title compound (22 g) as a colorless oil.

Step 3
(S)-2-Methyl-1-(4-methylsulfonylphenyl)-prop-2-en-1-ol

To a solution of dry 4 molecular sieves (20 g), and Ti (O$_2$Pr)$_4$ (24.8 mL) in CH$_2$Cl$_2$ (1 L) cooled to −25° C. was added dropwise (+)-diisopropyltartrate (22.4 mL). After stirring at −25° C. for 30 min., a solution of (±)-2-methyl-1-(4-methylsulfonylphenyl)-prop-2-en-1-ol (21 g) in 500 mL of CH$_2$Cl$_2$ was added dropwise, followed by a solution of t-butyl hydroperoxide (20 mL, 5 M in decane). The reaction mixture was stirred at −25° C. for 5 h and then quenched with 500 mL of 10% aqueous solution of tartaric acid. After stirring for 1 h, the CH$_2$Cl$_2$ layer was separated, dried over MgSO$_4$ and concentrated. The residue was purified by silica gel chromatography eluted first with 3:1 hexane/EtOAc followed by 1:2 hexane/EtOAc to give the title compound as a white solid (9 g).

Step 4
(R)-(2-Methyloxiran-2-yl)-(4-methanesulfonylphenyl) methanol

Following the same procedure described in Step 3 using 15 g of 4 A molecular sieves, 500 mL of CH$_2$Cl$_2$, 12.4 mL of Ti(OiPr)$_4$, 11.2 mL of (−)-diisopropyl tartrate, 20 mL of 5 M tBuOOH in decane and 9.8 g of the product from Step 3, the title compound (7.6 g, white solid) was obtained.

Step 5
(R)-[(1-Ethoxy-ethoxy)-(4-methanesulfonylphenyl)-methyl]-2-methyloxirane

To a solution of the product from Step 4 (7.2 g) and ethylvinyl ether (50 mL) in 200 mL of CH$_2$Cl$_2$ cooled to 0° C. was added 50 mg of camphorsulfonic acid. The reaction mixture was stirred at r.t. for 20 min. and then treated with 1 mL of Et$_3$N, concentrated to give the crude title compound (9 g).

Step 6
(R,S)-1-(1-Ethoxy-ethoxy)-2-methyl-1-(4-methylsulfonylphenyl)-butan-2-ol

To a suspension of CuI (20 g) in EtO (450 mL) cooled at −40° C. was added dropwise a solution of MeLi (150 mL, 1.4 M in Et$_2$O). After stirring at −40° C. for 20 min., a solution of the crude product from Step 7 (9 g) in 50 mL of Et$_2$O was added. The reaction mixture was stirred at −40° C. for 30 min. and then quenched with 20 mL of MeOH and 300 mL of saturated NH$_4$Cl solution. Air was bubbled into the mixture with stirring at r.t. for 1 h. The resulting mixture was then extracted with 400 mL of Et$_2$O and the Et$_2$O extract was dried over MgSO$_4$ and concentrated to give the crude title compound (10 g) which was used for next step without further purification.

Step 7
(R,S)-2-Methyl-1-(4-methylsulfonylphenyl)-butane-1,2-diol

A solution of the crude product from Step 8 (10 g) in 200 mL of THF, 50 mL of AcOH and 50 mL of H$_2$O was heated at 50° C. for 15 h. The mixture was then concentrated to give the crude title compound (7 g) which was used for next step with further purification.

Step 8
(S)-2-Hydroxy-2-methyl-1-(4-methylsulfonylphenyl)-butan-1-one

To a solution of the crude product from Step 7 (7 g) and (Bu$_3$Sn)$_2$O (30 mL) in 150 mL of CH$_2$Cl$_2$ cooled at 10° C. was added a solution of Br$_2$ (9.3 g in 30 mL of CH$_2$Cl$_2$). After stirring at r.t. for 30 min. the mixture was diluted with a solution of KF (500 mL, 3 N) and 500 mL of Et$_2$O. The solid generated was removed by filtration and the filtrate was separated. The organic layer was dried over MgSO$_4$ and concentrated. The residue was purified by silica gel chromatography eluted with 1:1 hexane/EtOAc to give 5 g of the title compound as a yellow oil.

$^1$H NMR (acetone-d$_6$) δ 8.31 (2H,d), 8.00 (2H,d), 4.67 (1H,s), 3.18 (3H,s), 2.00 (1H,m), 1.30 (1H,m), 1.50 (3H,s), 0.90 (3H,t).

Step 9

5(S) 5-ethyl-S-methyl-4-(4-(methylsulfonyl)phenyl)-3-(2-propoxy)-5H-furan-2-one

The title compound was prepared as described in Example 1 Step 4 using 2-propoxyacetic acid and 2(S) 2-hydroxy-2-methyl-1-(4-(methylsulfonyl)phenyl)butan-1-one.

$^1$H NMR M(CD$_3$COCD$_3$) δ 0.80 (3H,t), 1.30 (6H,t), 1.70 (3H,s), 2.10 (2H,m), 3.20 (3H,s), 5.25 (1H,m), 8.05 (4H,m).

EXAMPLE 146 AND 147

3-(1-cyclopropylethoxy)-5,5-dimethyl-4-(4-(methylsulfonyl)phenyl)-5H-furan-2-one (146) and 3-(1-cyclopropylethoxy)-5,5-dimethyl-4-(4-(methylsulfonyl)phenyl)-5H-furan-2-one (147)

The racemate of Example 134 was separated on a HPLC CHIRALPAK AD (Daicel) column with 10% isopropanol in hexane.

EXAMPLE 148

3-(cyclopropylmethoxy)-5,5-dimethyl-4-(4-(methylsulfonyl)phenyl-5H-furan-2-one

Step 1
3-(cyclopropylmethoxy)-5,5-dimethyl-4-(4-(methylsulfonyl)phenyl-5H-furan-2-one The title compound was prepared as described in Example 141 using 5,5-dimethyl-3-hydroxy-4-(4-(methylsulfonyl)phenyl-5H-furan-2-one and (bromomethyl)cyclopropane.

$^1$H NMR (CD$_3$COCD$_3$) δ 0.30 (2H,m), 0.55 (2H,m), 1.15 (1H,m), 1.60 (6H,s), 3.20 (3H,s), 4.20 (2H,d), 8.00 (4H,s).

EXAMPLE 149

5,5-dimethyl-3-(isobutoxy)-4-(4-(methylsulfonyl)phenyl)-5H-furan-2-one

The title compound was prepared as described in Example 141 using 5,5-dimethyl-3-hydroxy-4-(4-(methylsulfonyl)phenyl-5H-furan-2-one and 1-bromo-2-methylpropane.

$^1$H NMR (CD$_3$COCD$_3$) δ 0.90 (6H,d), 1.65 (6H,d), 1.95 (1H,m), 3.20 (3H,s), 4.10 (2H,d), 8.00 (4H,m).

EXAMPLE 150

3-(4-Bromophenoxy)-5,5-dimethyl-4-(4-(methylsulfonyl)phenyl)-5H-furan-2-one

Following the procedure described for Example 1, the title compound was prepared from bromophenoxy acetic acid.

M.P.: 150–152° C. $^1$H NMR (CD$_3$COCD$_3$) δ 1.77 (6H,s), 3.15 (3H,s), 7.07 (2H,d), 7.46 (2H,d), 7.92 (2H,d), 8.02 (2H,d).

EXAMPLE 53

3-(6-Amino-2-pyridyloxy)-5,5-dimethyl-4-(4-(methylsulfonyl)phenyl)-5H-furan-2-one Following the procedure described for Example 25, the title compound was prepared from 2-hydroxy-6-aminopyridine.

M.P.: 165–166° C. $^1$H NMR (CD$_3$COCD$_3$) δ 1.74 (6H,s), 3.14 (3H,s), 5.52 (2H,s,br), 6.17 (1H,d), 6.24 (1H,d), 7.41 (1H,t), 7.90 (2H,d), 8.02 (2H,d).

EXAMPLE 31

3-(2-Quinolinoxy)-5,5-dimethyl-4-(4-(methylsulfonyl)phenyl)-5H-furan-2-one

Following the procedure described for Example 25, the title compound was prepared from 2-hydroxyquinoline.

M.P.: 141–142° C. $^1$H NMR (CD$_3$COCD$_3$) δ 1.83 (6H,s), 3.11 (3H,s), 7.26 (1H,m), 7.52 (1H,m), 7.70 (1H,m), 7.77 (1H,m), 7.93–8.02 (5H,m), 8.39 (1H,s).

EXAMPLE 50

3-(2-Chloro-5-pyridyloxy)-5,5-dimethyl-4-(4-(methylsulfonyl)phenyl)-5H-furan-2-one Following the procedure described for Example 25, the title compound was prepared using 2-chloro-5-hydroxypyridine.

M.P.: 196–197° C. $^1$H NMR (CD$_3$COCD$_3$) δ 1.78 (6H,s), 3.16 (3H,s), 7.33 (1H,m), 7.68 (1H,m), 7.94 (2H,d), 8.04 (2H,d), 8.14 (1H,m).

EXAMPLE 159

3-(6-benzothiazolyloxy)-5,5-dimethyl-4-(4-(methylsulfonylphenyl)-5H-furan-2-one

Following the procedure described for Example 25, the title compound was prepared from 6-hydroxybenzothiazole M.P.: 212° C. $^1$H NMR (CD$_3$COCD$_3$) δ 1.79 (6H,s), 3.10 (3H,s), 7.34 (1H,s), 7.86 (1H,d), 7.93–8.00 (5H,m), 9.15 (1H,s).

EXAMPLE 160

3-(6-Chloro-2-pyridiloxy)-5,5-dimethyl-4-(4-(methylsulfonyl)phenyl)-5H-furan-2-one Following the procedure described in Example 25, the title compound was prepared from 6-chloro-2-hydroxypyridine M.P.: 119–121° C. $^1$H NMR (CD$_3$COCD$_3$) d 1.78 (6H,s), 3.15 (3H,s), 7.10 (1H,d), 7.25 (1H,d), 7.89–8.06 (5H,m).

EXAMPLE 161

3-(4-Quinazolyloxy)-5,5-dimethyl-4-(4-(methylsulfonyl)phenyl)-5H-furan-2-one

Following the procedure described in Example 25, the title compound was prepared from 4-hydroxyquinazoline.

M.P.: 174–177° C.

$^1$H NMR (CD$_3$COCD$_3$) δ 1.76 (6H, s), 3.12 (3H, s), 7.58 (1H, t), 7.67 (1H, d), 7.76 (2H, d), 7.85 (1H, t), 8.03 (2H, d), 8.16 (1H, d), 8.22 (1H, s).

EXAMPLE 162

(5R)-3-(5-Fluoro-2-pyridyloxy)-5-ethyl-5-methyl-4-(4-methylsulfonyl)-phenyl-5H-furan-2-one Following the procedure described for Example 25, the title compound was prepared from (2R)-2-chloroacetoxy-2-methyl-1-(4-methylsulfonyl)phenylbutan-1-one (prepared similarly to the compound of Example 5, Step 1 but using the 2-(R) compound of Example 117, Step 3) and 5-fluoro-2-hydroxy-pyridine. M.S.: (CI, CH4) m/z 392 (M+H)$^+$ $^1$H NMR (CD$_3$COCD$_3$) δ 0.95 (3H, t), 1.76 (3H, s), 2.12 (2H, m), 3.15 (3H, s), 7.18 (1H, m), 7.73 (1H, m), 7.91 (2H, d), 8.02–8.07 (3H, m).

EXAMPLE 163

(5R)-3-(4-Fluorophenoxy)-5-ethyl-5-methyl-4-(4-methylsulfonyl) phenyl-5H-furan-2-one Following the procedure described in Example 1, Step 4, the title compound was prepared using (2R)-2-hydroxy-2- methyl-1-(4-methylsulfonyl)phenylbutan-1-one (Example 117, Step 3) and 4-fluorophenoxy acetic acid. M.P.: 968–97.4° C.
$^1$H NMR (CD$_3$COCD$_3$) δ 0.92 (3H, t), 1.77 (3H, s), 2.11 (2H, q), 3.14 (3H, s), 7.08–7.11 (4H, m), 7.9 (2H, d), 8.02 (2H, d).

EXAMPLE 164

(5R)-3-(5-Fluoro-2-pyridyloxy)-5-methyl-4-(4-methylsulfonyl) phenyl-5-(2,2,2-trifluoroethyl)-5H-furan-2-one Following the procedure described for Example 25, the title compound was prepared from (2R)-2)chloroacetoxy-2-methyl-1-(4-methylsulfonyl)phenyl-4,4,4-trifluorobutan-1-one (Example 130, Step 3) and 5-fluoro-2-hydroxypyridine.
$^1$H NMR (CD$_3$COCD$_3$) δ 1.94 (3H, s), 3.15 (3H, s), 3.24 (2H, q), 7.20 (1H, m), 7.75 (1H, m), 7.73–8.07 (5H, m).

EXAMPLE 165

3-(1-Isoquinolinyloxy)-5,5-dimethyl-4-(methylsulfonyl)phenyl-5H-furan-2-one

Following the procedure described for Example 25, the title compound was prepared using 1-hydroxyisoquinoline. M.P.: 193.5–194.5
$^1$H NMR (CD$_3$COCD$_3$) δ 1.75 (6H, s), 3.12 (3H, s), 6.57 (1H, d), 7.27 (1H, d), 7.50–7.76 (5H, m), 8.02 (2H, d), 8.24 (1H, d).

EXAMPLE 166

(5R)-3-(4-fluorophenoxy)-5-methyl-4-(4-methylsulfonyl)phenyl-5-(2,2,2-trifluoroethyl)-5H-furan-2-one Following the procedure described in Example 1, Step 4, the title compound was prepared using 2-(R)-hydroxy-2-methyl-1-(4-(methylsulfonyl)phenyl)-4,4,4-trifluoro-1-butanone (Example 130, Step 2) and 4-fluorophenoxyacetic acid. M.P.: 104.7–107.0° C.
$^1$H NMR (CD$_3$COCD$_3$) δ 1.94 (3H, s), 3.15 (3H, s), 3.27 (2H, m), 7.07–7.13 (4H, m), 7.98–8.04 (4H, m), M.S.: (CI, CH$_4$) m/z 463 (M+H)$^+$

EXAMPLE 167

3-(3-Fluoro-2-pyridyloxy)-5,5-dimethyl-4-(4-methylsulfonyl) phenyl-5H-furan-2-one Following the procedure described for Example 5, the title compound was prepared using 3-fluoro-2-hydroxypyridine M.P.: 156–157° C.
$^1$H NMR (CD$_3$COCD$_3$) δ 1.78 (6H, s), 3.14 (3H, s), 7.23 (1H, m), 7.72 (1H, m), 7.91 (2H, d), 7.96 (1H, d), 8.03 (2H, d).

EXAMPLE 168

(5R)-3-(3,4-difluorophenoxy)-5-methyl-4-(4-methylsulfonyl) phenyl-5-(2,2,2-trifluoroethyl)-5H-furan-2-one Following the procedure described for Example 25, the title compound was prepared from (2R)-2-chloroacetoxy-2-methyl-1-(4-methylsulfonyl)phenyl-4,4,4-trifluorobutan-1-one (Example 130, Step 3) and 3,4-difluorophenol.

EXAMPLE 169

(5R)-3-(5-chloro-2-pyridyloxy)-5-ethyl-5-methyl-4-(4-methylsulfonyl) phenyl-5H-furan-2-one To a solution of 2(R)-hydroxy-2-methyl-1-(4-(methylsulfonyl)phenyl)-1-butanone (800 mg, 30 mmol), Example 117, Step 3, in 24 mL of acetonitrile was added chloroacetic acid (383 mg), CMC (1.7 g) and DMAP (20 mg). The mixture was then stirred at r.t. for 4 hours. Then 5-chloro-2-hydroxypyridine (602 mg) and DBU (1.85 mL) were added and the mixture was stirred for 18 hours. Water was then added to the mixture which was extracted with CH$_2$Cl$_2$, then washed with 1N Hcl, brine, dried over MgSO4, filtered and the solvent evaporated under vacuum purification by flash chromatography on silica gel 40% EtOAc/Hexane afforded the title compound. M.P.: 191° C.
$^1$H NMR (CD$_3$COCD$_3$) δ 0.95 (3H, t), 1.76 (3H, s), 2.11 (2H, m), 3.15 (3H, s), 7.18 (1H, d), 7.89–7.93 (3H, m), 8.03 (2H, d), 8.16 (1H, d).

EXAMPLE 170

3-(3,4-difluorophenoxy)-5-methyl-5-trifluoromethyl-4-(4-methylsulfonyl)phenyl-5H-furan-2-one Step 1

2-Trifluoromethyl-2-trimethylsiloxypropionitrile

A mixture of 1,1,1-trifluoroacetone (8.9 mL, 0.1 mmol), trimethylsilylcyanide (13.3 mL, 0.1 mmol) and zinc iodide (5 mg) was stirred for 18 hours, to afford the title compound.

Step 2

2-Hydroxy-1-(4-methylthio)phenyl-2-trifluromethyl propanone

To a solution of 4-bromothioanisole (19 g, 94 mmol) in THF (200 mL) at −78° C. was added 1.33 M n-Butyl lithium (71 mL, 94 mmol). The mixture was stirred for 1 hr at −78° C. then 10 g (47 mmol) of the compound from Step 1 was added and the mixture was left to warm to r.t. The reaction mixture was quenched with 25% NH4OAc extracted with EtOAc, washed with brine, dried over MgSO4, filtered and the solvent evaporated to afford 9.7 g of the title compound.

Step 3

2-Hydroxy-1-(4-methylsulfonyl)phenyl-2-trifluoromethyl propanone

Following the procedure described in Example 117, Step 3, and using the compound from the previous step, the title compound was obtained.

Step 4

3-(3,4-difluorophenoxy)-5-methyl-5-trifluoromethyl-4-(4-methylsulfonyl)phenyl-5H-furan-2-one Following the procedure described in Example 1, Step 4, and using the compound obtained in the previous step, the title compound was obtained. M.P.: 154.1° C.
$^1$H NMR (CD$_3$COCD$_3$) δ 2.06 (3H, s), 3.15 (3H, s), 6.98 (1H, s), 7.7 (1H, m), 7.26 (1H, dd), 7.77 (2H, d), 8.02 (2H, d).

EXAMPLE 171

3-(3,4-Difluorophenoxy)-5-methyl-4-(4-methylsulfonyl)phenyl)-5-propyl-5H-furan-2-one Step 1

2-Methyl-1-(4-methylthiophenyl)-pentan-1-one

Following the procedure described for Example 1, Step 1, the title compound was prepared from 2-methyvaleryl chloride and thioanisole.

Step 2

2-Hydroxy-2-methyl-1-(4-methylthiophenyl)-pentan-1-one

Following the procedure described for Example 1, Step 2, the title compound was prepared from the produce obtained in Step 1.

Step 3

(3,4-Difluorophenoxy)-acetic acid 1-methyl-1-(4-methythiobenzoylbutyl)ester

A solution of 3,4-difluorophenoxyacetic acid (0.38 g), the product from Step 2 (0.24 g), CMC (1.0 g), and DMAP (100 mg) in 5 mL of $CH_2Cl_2$ was stirred at r.t. for 15 h. The reaction mixture was then treated with saturated solution of $NaHCO_3$ (20 mL) and extracted with 1:1 EtOAc/hexane (100 mL). The organic layer was dried over $MgSO_4$ filtered and concentrated to give the crude product which was used for next step without further purification.

Step 4

(3,4-Difluorophenoxy)-acetic acid 1-methyl-1-(4-methysulfonylbenzoylbutyl ester A solution of the crude product from Step 3 in 50 mL of 10:1 $CH_2Cl_2$/MeOH (v/v) was treated with MMPP (1.0 g). The mixture was stirred at r.t. for 30 min. and then diluted with saturated $NaHCO_3$ solution (50 mL). The mixture was extracted with EtOAc (50 mL) and the organic layer was dried over $MgSO_4$, filtered and concentrated to give the title compound as a white solid.

Step 5

3-(3,4-Difluorophenoxy)-5-methy-4-(4-(methylsulfonyl) phenyl)-5-propyl-5H-furan-2-one A solution of the product from Step 4, $CF_3CO_2iPr$ (0.5 mL) and DBU (0.2 mL) in $CH_3CN$ (30 mL) was heated to reflux for 30 min. The mixture was then cooled to r.t. treated with ACOH (1 mL) and concentrated. The residue was dissolved in 2:1 EtOAc/hexane (20 mL) and filtered through a pad of silica gel. The filtrate was concentrated and the residue was stirred at 5° C. 5:1 hexane/EtOAc (10 mL) for 15 h. The title compound was isolated by filtration as a white solid (380 mg).

$^1$H NMR (acetone-$d_6$) δ 8.04 (2H, d), 7.93 (2H, d), 7.28 (1H, m), 7.12 (1H, m), 6.92 (1H, m)(, 3.15 (3H, s), 2.06 (2H, m), 1.79 (3H, s), 1.80–1.96 (2H, m), 0.92 (3H,t).

EXAMPLE 174

3-Cyclobutyloxy-5,5-dimethyl-4-(4-methylsulfonylphenyl-5H-furan-2-one

Following the procedure described for Example 14, the title compound was obtained using cyclobutyloxyacetic acid. M.P. 111–112° C.; Ms (Cl, $CH_4$) m/z 337 (M+H)$^+$; anal, calcd for $C_{17}H_{20}O_5S$: C, 60.70; H, 5.99; S, 9.53; found: C, 60.39; H, 6.05; S, 9.60.

EXAMPLE 175

3-(1-Indanyloxy)-5,5-dimethyl-4-(4-methylsulfonyl) phenyl)-5H-furan-2-one

Following the procedure described for Example 14, the title compound was obtained using 1-indanyloxyacetic acid. M.p. 128–129° C.; MS (Cl, $CH_4$) m/z 398 (M+H)$^+$; and anal. calcd. for $C_{22}H_{22}O_5S$: C, 66.31; H, 5.56; S, 8.05; found: C, 66.27; H, 5.47; 5, 8.34.

EXAMPLE 176

3-(2-Indanyloxy)-5,5-dimethyl-4-(4-methylsulfonyl) phenyl)-5H-furan-2-one

Following the procedure described for Example 14, the title compound was obtained using 2-indanyloxyacetic acid. M.p. 142–143° C.; Ms (Cl, $CH_4$) m/z 3.99 (M+H)$^+$; anal. calcd. for $C_{22}H_{22}O_5S$: C, 66.31; H, 5.56; found: C, 66.50; H, 5.64.

EXAMPLE 177

3-Cycopentyloxy-5,5-dimethyl-4-(4-methysulfonylphenyl)5H-furan-2-one

Following the procedure described for Example 109 the title compound was prepared from cyclopentyl bromide. M.P.: 121–122° C.

$^1$H NMR (CD$_3$COCD$_3$) δ 1.55–1.85 (8H, m), 1.65 (6H, s), 3.15 (3H, s), 5.43 (1H, m), 7.98–8.07 (4H, m).

EXAMPLE 178

3-(3,3-Dimethylcyclopentloxy)-5,5-dimethyl-4-(4-methylsulfonyl-phenyl)-5H-furan-2-one Step 1

3,3-Dimethylcyclopentanol

To a solution of 4,4-Dimethyl-2-cyclopenten-1-one (1.65 g, 15 mmol) in EtOAc (50 mL) was added palladium on activated carbon (270 mg). The resulting suspension was vigorously stirred under an hydrogen atmosphere for 22 hours. The reaction was diluted with $CH_2Cl_2$ (150 mL) and filtered on a pad of silica gel washed with EtOAc. The solvents were removed by distillation under atmospheric pressure using a 15 cm Vigreux column. The distillation residue was dissolved in MeOH (50 mL) cooled to 0° C. and sodium borohydride (304 mg, 8 mmol) was added and the reaction mixture was stirred at r.t. for 24 h. The reaction was diluted with NH4OAc eq. 25% w/r and extract with EtOAc. The organic layer was separated, dried over $MgSO_4$ and concentrated. Purification by silica gel chromatography (50% Et2O/pentane) provided 1.14 g of the title compound as a colorless liquid.

$^1$H NMR (CD$_3$COCD$_3$) δ 0.94 (3H, s), 1.07 (3H, s), 1.24–1.4 (2H, m), 1.55–1.63 (2H, m), 1.67 (1H, dd), 1.85–1.95 (1H, m), 3.42 (1H, d), 4.27 (1H, m).

Step 2

3-Iodo-1,1-dimethylcyclopentane

To a 0° C. solution of 3,3-Dimethylcyclopentanol (Step 1) (1.14 g, 10 mmol) and triethylamine (2.0 mL, 14.3 mmol) in dichloromethane was added dropwise methanesulfonyl chloride (1.0 mL, 12.9 mmol). The reaction was allowed to proceed for 30 min. at 0° C., then it was diluted with water and extracted twice with $CH_2Cl_2$. The combined organic layers were dried over MgSO4 and concentrated in vacuo. The resulting residue was dissolved in acetone (50 mL), cooled to 0° C. and lithium iodide (6.68, 50 mmol) was added). The resulting suspension was stirred at r.t. for 20 hours. Most of the solvent was removed in vacuo, the residue was taken in EtOAc and washed twice with water. The organic layer was dried over $MgSO_4$ and concentrated. This crude product was purified by flash chromatography eluted with 40 Et$_2$O/pentane to give the title compound as a colorless oil.

$^1$H NMR (CD$_3$COCD$_3$) δ 0.98 (3H, s), 1.14 (3H, s), 1.38–1.46 (1H, m), 1.57–1.64 (1H, m), 1.93 (1H, dd), 2.06–2.16 (2H, m), 2.29 (1H, m), 4.38 (1H, quintet)

Step 3

Following the procedure described for Example 109, the title compound was prepared from 3-iodo-1,1-dimethylcyclopentanol (Step 2), M.P.: 99–100° C.
$^1$H NMR (CD$_3$COCD$_3$) δ 0.93 (3H, s), 0.99 (3H, s), 1.32–1.40 (1H, m), 1.48–1.62 (2H, m), 1.65 (6H, s), 1.74 (1H, dd), 1.78–1.88 (1H, m), 1.93–2.02 (1H, m), 3.17 (3H, s), 5.90 (1H, m), 8.02 (4H, dm).

EXAMPLE 179

3-Isopropoxy-5-methyl-4-(4-methylsulfonylphenyl)-5-propyl-5H-furan-2-one

Following the procedure described for Example 171, the title compound was prepared from isopropoxyphenyl acetic acid. M.P.: 95–96° C.
$^1$H NMR (CD$_3$COCD$_3$) δ 0.88 (3H, t), 1.12–1.323 (2H, m), 1.28 (6H, 2d), 1.67 (3H, s), 2.00 (2H, m), 3.17 (3H, s), 5.22 (1H, heptet), 8.04 (4H, s).

EXAMPLE 180

3-(2-Methoxy-5-pyridyloxy)-5,5-dimethyl-4-(4-methylsulfonyl)phenyl-5H-furan-2-one Step 1

5-Hydroxy-2-methoxypyridine

To 6M aqueous HCl(20 mL) at 00 C was added 5-amino-2-methoxypyridine(3.1 g, 25 mmol), stirred for 10 min and a solution of 4M aqueous NaNO2(7 mL, 28 mmol) was added dropwise over a period of 10 min. After further stirring for 30 min, 60% HPF6(2 mL) was added and precipitate formed immediately. The mixture was stirred for 15 min, H2O(50 mL) was added. The precipitate was collected, washed with H2O(3 x) and dried under vacuum to give the corresponding diazonium salt as brown powders (6.5 g, 92%).

The above diazonium salt in acetic anhydride(25 mL) was heated at 100–1100 C. for 1 h. Solvent was evaporated in vacuo. The residue was diluted with H2O and extracted with Et2O. Solid residue was filtered and the ethereal layer was separated, washed with saturated aq. NaHCO3 brine, dried (anhydrous MgSO4) and concentrated to provide the 5-acetoxy-2-methoxypyridine as a brown oil(600 mg).
$^1$H NMR (CD3COCD3) δ 2.26(3H, s), 3.85(3H, s), 6.78(1H, d), 7.48(1H, dd), 7.92(1H, d).

To a solution of the 5-acetoxy-2-methoxypyridine(600 mg, 3.59 mmol) in MeOH(10 mL) was added 1M aq. NaOH(10 mL, 10 mmol). After stirring at r.t. for 30 min, volatile solvent was removed in vacuo, acidified with HOAc and extracted with CHCl3(3 x). The combined CHCl3 extracts were washed with H2O, dried(anhydrous MgSO4) and evaporated to give the title compound as a brown oil(240 mg, solidified on standing).
$^1$H NMR (CD3COCD3) δ 3.78 (3H, s), 6.60(1H, d), 7.20 (1H, dd), 7.70(1H, d), 8.20(1H, br s).

Step 2

3-(2-Methoxy-5-pyridyloxy)-5,5-dimethyl-4-(4-methylsulfonyl)phenyl-5H-furan-2-one Following the procedure described for Example 25, the title compound was prepared from 5-hydroxy-2-methoxypyridine.
$^1$H NMR (CD$_3$COCD$_3$) δ 1.75(6H, s), 3.16(3H, s), 3.85(3H, s), 6.66(1H, d), 7.47(1H, dd), 7.90(2H, d), 7.95(1H, d), 8.04(2H, d).

EXAMPLE 181

3-(5-Methyl-2-pyridyloxy)-5,5-dimethyl-4-(4-methylsulfonyl)phenyl-5H-furan-2-one Step 1

2-Hydroxy-5-methylpyridine

Following the procedure described for Example 48, step 1, the title compound was prepared from 2-amino-5-picoline.
$^1$H NMR (CD$_3$COCD$_3$) δ 2.05(3H, s), 6.36(1H, d), 7.24(1H, d), 7.35(1H,dd).

Step 2

3-(5-Methyl-2-pyridyloxy)-5,5-dimethyl-4-(4-methylsulfonyl)phenyl-5H-furan-2-one Following the procedure described for Example 25, the title compound was prepared from 2-hydroxy-5-methylpyridine.
$^1$H NMR (CD$_3$COCD$_3$) δ 1.75(6H, s), 2.28, 3.16(3H, s), 6.98(1H, d), 7.68(1H, dd), 7.90(2H, d), 7.96(1H, d), 8.04 (2H, d).

EXAMPLE 184

(5RS)-3-(3,4-Difluorophenoxy)-5-methyl-4-(4-methylsulfonyl)phenyl-5-(2,2,2-trifluoroethyl)-5H-furan-2-one Step 1

2(RS)-2-Methyl-1-(4-(methylthio)phenyl)-4,4,4-trifluoro-1-butanone

Following the procedure described for example 1, step 1, the title compound was prepared from 2 (RS)-2-methyl-4,4,4-trifluoro-butryl chloride(GB 2238790-A) and thioanisole.
$^1$H NMR (CD3COCD3) δ 1.22(3H, d), 2.30(1H, m), 2.52 (3H, s), 2.82(1H, m), 3.88(1H, m), 7.35(2H, d), 7.92(2H, d), 7.92(2H, d).

Step 2

2(RS)-2-Hydroxy-2-methyl-1-(4-(methylthio)phenyl)-4,4,4-trifluoro-1-butanone

To 2-(RS)-2-hydroxy-2-methyl-1-(4-(methylthio)phenyl)-4,4,4-trifluoro-1-butanone(12 g, 45.8 mmol) and triethyl phosphite(16 mL) in DMF(250 mL) at −10° C. was added 1M t-BuOK(46 mL, 46 mmol) in t-BuOH and air was bubbled through the mixture for 3 h. After quenching with 2.5M aq. HOAc(20 mL), the mixture was diluted with H$_2$O, extracted with Et$_2$O. The etheral extract was washed with H$_2$O(2 x), 0.5M aq. NaOH, dried(anhydrous MgSO$_4$) and concentrated. Chromatography over silica gel and elution with hexanes:EtOAc(4:1) gave the title compound as a yellow oil(6.0 g, ~90% pure).
$^1$H NMR(CD$_3$COCD$_3$) δ 1.62(3H, s), 2.54(3H, s), 2.70–3.20 (2H, m), 7.32(2H, d), 8.15(2H,d).

Step 3

2-(RS)-2-Hydroxy-2-methyl-1-(4-(methylsulfonyl)phenyl)-4,4,4-trifluoro-1-butanone To a solution of 2-(RS)-2-hydroxy-2-methyl-1-(4-(methylthio)phenyl)-4,4,4-trifluoro-1-butanone(6.0 g, 21.6 mmol) in CH$_3$Cl(200 mL) was added mCPBA(12 g, Aldrich 27,303-1, 57–86%) at 0° C. The mixture was slowly warmed to r.t. over a period of 1 h, washed with 1M aq. NaOH(2 x), brine, dried(anhydrous MgSO$^4$) and concentrated. Chromatography over silica gel and elution with hexanes:EtOAc (2:1) provided the title compound(4.0 g, 60%).

¹H NMR(CD³COCD³) δ 1.66(3H, s), 2.70–3.20(2H, m), 3.18(3H, s),5.35(1H,s), 8.04(2H, d), 8.30(2H, d).

Step 4

(5RS)-3-(3,4-Difluorophenoxy)-5-methyl-4-(4-methylsulfonyl)phenyl)-5-(2,2,2-trifluoroethyl)-5H-furan-2-one Following the procedure described for example 1, step 4, the title compound was prepared from 3,4-difluorophenoxyacetic acid and 2-(RS)-2-hydroxy-2-methyl-1-(4-(methylsulfonyl)phenyl)-4,4,4-trifluoro-1-butanone. NMR of the title compound is the same as Example 168.

EXAMPLE 185

3-(3-Chloro-4-methoxyphenoxy)-5,5-dimethyl-4-(4-methylsulfonyl)-phenyl-5H-furan-2-one Step 1

3-Chloro-4-methoxyphenoxyacetic acid

To a mixture of hydroquinone(24 g, 0.22 mol) and ethyl bromoacetate(24 mL, 0.22 mol) in DMF(300 mL) was added 10 M aq. NaOH(22 mL, 0.22 mol). The mixture was stirred at 0° C. for 1 h, diluted with H2O, acidified with 6M aq. HCl and extracted with EtOAc. The EtOAc extract was dried(anhydrous $MgSO_4$) and concentrated in vacuo. The residue was swished with Et2O to give ethyl 4-hydroxyphenoxy-acetate(5.8 g) as a white powder.

Ethyl 4-hydroxyphenoxyacetate (1.5 g, 7.6 mmol) was reacted with $SO_2Cl_2$(1.5 mL) to give ethyl 3-chloro-4hydroxyphenoxyacetate (700 mg, ~80% pure) as a white powder. To a solution of ethyl 3-chloro-4-hydroxyphenoxyacetate (700 mg, 3.0 mmol) and MeI(0.28 mL, 4.5 mmol) in DMF(5 mL) at 0° C. was added 10M aq.NaOH(0.320 mL, 3.2 mmol). The mixture was stirred at r.t. for 12 h, then diluted with $H_2O$ and extracted with EtOAc to give ethyl 3-chloro-4-methoxyphenoxy-acetate (700 mg).

The above ethyl 3-chloro-4-methoxyphenoxyacetate (700 mg) was hydrolysed with 1M aq. NaOH in THF-MeOH (30 mL, 2:1) to provide the title compound as a white powder. ¹NMR(CD3COCD3) δ 3.84(3H, s), 4.70(2H, s), 6.85–7.10 (3H, m).

Step 2

3-(3-Chloro-4-methoxytphenoxy)-5,5-dimethyl-4-(4-methylsulfonyl)phenyl-5H-furan-2-one Following the procedure described for example 1, step 4, the title compound was prepared from 3-chloro-4-methoxyphenoxyacetic acid and 2-hydroxy-2-methyl-1-(4-methylsulfonyl)phenyl)propan-1-one(example 1, step 3).

¹H NMR(CD3COCD3) δ 1.75(6H, s), 3.14(3H, s), 3.84(3H, s), 6.95–7.20(3H, m), 7.86(2H, d), 8.00(2H, d).

EXAMPLE 186

(5R)-3-(3-Chloro-4-methoxyphenoxy)-5-ethyl-5-methyl-4-(4-methylsulfonyl)phenyl-5H-furan-2-one Following the procedure described for Example 1, step 4, the title compound was prepared from 3-chloro-4-methoxyphenoxyacetic acid and (2R)-2-hydroxy-2-methyl-1-(4-methylsulfonyl)phenyl-butan-1-one (Example 117, Step 3).

¹H NMR(CD3COCD3) δ 0.94(3H, t), 1.76(3H, s), 2.10(2H, q), 3.15(3H, s), 3.85(3H, s), 6.95–7.20(3H, m), 7.90(2H, d), 8.00(2H, d).

EXAMPLE 188

(5R)-3-(4-Chlorophenoxy)-5-(2,2,2-trifluoroethyl)-5-methyl-4-(4-methylsulfonyl)phenyl-5H-furan-2-one Following the procedure described for Example 1, Step 4, the title compound was prepared form 4-chlorophenoxyacetic acid and (2R)-2-hydroxy-2methyl-1 (4-methylsulfonyl)phenyl-4,4,4-trifluoro-butan-1-one (Example 130, Step 2).

¹H NMR(CD$_3$COCD$_3$) δ 1.95 (3H, s), 3.15 (3H, s), 3.25 (2H, m), 7.12 (2H, d), 7.36 (2H, d), 8.02 (4H, m).

Analysis calculated for $C_{20}H_{16}ClF_3O_5S$: C, 52.13; H, 3.50 Found: C, 52.27; H, 3.63.

EXAMPLE 189

(5R)-3-(4-Bromophenoxy)-5-(2,2,2-trifluoroethyl)-5-methyl-4-(4-methylsulfonyl)phenyl-5H-furan-2-one Following the procedure described for Example 1, step 4, the title compound was prepared from 4-bromophenoxyacetic acid and (2R)-2-hydroxy-2-methyl-1-(4-methylsulfonyl)phenyl-4,4,4-trifluorobutan-1-one (Example 130, Step 2).

¹H NMR (CD$_3$COCD$_3$) δ 1.94 (3H,s), 3.15 (3H,s), 3.25 (2H,m), 7.07 (2H,d), 7.50 (2H,d), 8.02 (4H,m).

EXAMPLE 195

5-Cyclopropylmethyl-3-(3,4-difluorophenoxy)-5-methyl-(4-methylsulfonyl)phenyl-5H-furan-2-one Step 1: 2-cyclopropylmethyl-2-methyl-1-(4-thiomethyl) phenyl-propan-1-one To a cold (−78° C.) solution of 1-(4-thiomethyl)phenyl-propan-1-one (900 mg, 5 mmol) in dry THF (15 mL) was added a solution of KHMDS (5.5 mmol, 11 mL). The mixture was warmed to r.t. for 5 min and then cooled to 0° C. Bromomethylcyclopropane (810 mg, 6 mmol) was added. The mixture was warmed to r.t. and stirred for 20 h. Aqueous $NH_4Cl$ solution was added. The mixture was extracted with EtOAc and the concentrated crude extract was purified by chromatography on silica gel (eluted with 20% EtOAc/hexane) to give 435 mg (37%) of the title compound.

Step 2: 2-Cyclopropylmethyl-2-methyl-1-(4-methylsulfonyl)phenyl-propan-1-one

To a solution of the product of step 1 (435 mg, 1.87 mmol) in a mixture of $CH_2ClCH_2Cl$ (10 mL) and methanol (10 mL) was added MMPP (2.3 g 3.7 mmol) in 2 portions. The mixture was stirred at r.t. for 6 h. $H_2O$ was added and the product was extracted with EtOAc. The extracts were washed with $H_2O$ and brine, dried and concentrated to an oil. The crude oil was purified by chromatography on silica gel (eluted with 30% EtOAc/hexane) to give 363 mg (83%) of the title compound.

Step 3: -Cyclopropylmethyl-2-hydroxy-2-methyl-1-(4-methylsulfonyl)phenyl-propan-1-one To a mixture of the product of step 2 (310 mg, 1.16 mmol), $CCl_4$ (268 mg, 1.74 mmol), Aliquat 336® (75 mg, 0.185 mmol) and toluene (293 mg, 3.19 mmol) was added powered NaOH (102 mg, 2055 mmol) in portions. Aqueous $NH_4Cl$ solution was added. The mixture was neutralized with 1N HCl and extracted with EtOAc and the concentrated crude extract was purified by chromatography on silica gel (eluted with 30% EtOAc/hexane) to give 124 mg (38%) of the title compound.

Step 4: 5-Cyclopropylmethyl-3-(3,4-difluorophenoxy)-5-methyl-4-(4-methylsulfonyl)phenyl-5H-furan-2-one Following the procedure described for Example 117, the title compound was prepared from the product of step 3 and 3,4-difluorophenoxyacetic acid.

¹H NMR (CD$_3$COCD$_3$) δ-0.01 (1H,m), 0.19 (1H,m), 0.42 (1H,m), 0.51 (1H,m), 0.71 (1H,m), 1.82 (3H,s), 1.87 (1H,dd), 2.26 (1H,dd), 3.15 (3H,s), 6.95 (1H,m), 7.14 (1H,m), 7.29 (1H,q), 8.05 (4H,q).

EXAMPLE 196

(5R)-3-(3-Fluorophenoxy)-5-ethyl-5-methyl-4-(4-methylsulfonyl)phenyl-5H-furan-2-one Following the procedure described for Example 25, the title compound was prepared from 3-fluorophenol and (2R)-2-chloroacetoxy-2-methyl-1-(4-methylsulfonyl)phenyl-butan-1-one, prepared as in Example 162.

$^1$H NMR (CD$_3$COCD$_3$) δ 0.93 (3H,t), 1.79 (3H,s), 2.13 (2H,q), 3.15 (3H,s), 6.89 (3H,m), 7.46 (1H,q), 7.93 (2H, d), 8.05 (2H,d).

EXAMPLE 197

(5R)-3-(4-Chloro-3-fluorophenoxy)-5-ethyl-5-methyl-4-(4-methylsulfonyl)phenyl-5H-furan-2-one Following the procedure described for Example 25, the title compound was prepared from 4-chloro-3-fluorophenoxyacetic acid and (2R)-2-chloroacetoxy-2-methyl-1-(4-methylsulfonyl)phenyl-butan-1-one.

$^1$H NMR (CD$_3$COCD$_3$) δ 0.94 (3H,t), 1.80 (3H,s), 2.13 (2H,q), 3.15 (3H,s), 6.95 (1H,m), 7.10 (1H,m), 7.48 (1H,t), 7.94 (2H,d), 8.04 (2H,d).

EXAMPLE 198

(5R)-3-(3-Phenoxy)-5-ethyl-5-methyl-4-(4-methylsulfonyl)phenyl-5H-furan-2-one

Following the procedure described for Example 25, the title compound was prepared from phenol and (2R)-2-chloroacetoxy-2-methyl-1-(4-methylsulfonyl)phenylbutan-1-one, prepared as in Example 162.

$^1$H NMR (CD$_3$COCD$_3$) δ 0.94 (3H,t), 1.78 (3H,s), 2.15 (2H,q), 3.14 (3H,s), 7.09 (3H,m), 7.33 (2H,m), 7.93 (2H,d), 8.01 (2H,d).

Analysis calculated for C$_{20}$H$_{20}$O$_5$S: C, 64.50; H,5.41. Found: C, 63.94; H, 5.48.

EXAMPLE 199

(5R)-3-(4-Chloro-3-methylphenoxy)-5-ethyl-5-methyl-4-(4-methylsulfonyl)phenyl-5H-furan-2-one Following the procedure described for Example 25, the title compound was prepared from 4-chloro-3-methylphenol and (2R)-2-chloroacetoxy-2-methyl-1-(4-methylsulfonyl)phenyl-butan-1-one, prepared as in Example 162.

$^1$H NMR (CD$_3$COCD$_3$) δ 0.93 (3H,t), 1.78 (3H,s), 2.12 (2H,q), 2.30 (3H,s), 3.15 (3H,s), 6.91 (1H,dd), 7.04 (1H,d), 7.30 (1H,d), 7.92 (2H, d) 8.02 (2H,d).

Analysis calculated for C$_{21}$H$_{21}$ClO$_5$S: C, 59.93; H, 5.03. Found: C, 59.59; H, 5.02.

EXAMPLE 200

3-(4-Chloro-3-methylphenoxy)-5-5-dimethyl-4-(4-methylsulfonyl)phenyl-5H-furan-2-one Following the procedure described for Example 108, the title compound was prepared from 4-chloro-3-methylphenoxyacetic acid and 2-chloroacetoxy-2-methyl-1-(4-(methylsulfonyl)phenyl)propan-1-one.

$^1$H NMR (CD$_3$COCD$_3$) δ 1.76 (6H,s), 2.79 (3H,s), 3.15 (3H,s), 6.92 (1H,dd), 7.06 (1H,d), 7.28 (1H,d), 7.92 (2H,d), 8.02 (2H,d).

Analysis calculated for C$_{21}$H$_{19}$ClO$_5$S: C, 59.04; H, 4.71. Found: C, 59.18; H, 4.78.

EXAMPLE 201

(5R)-3-(5-bromo-2-pyridyloxy)-4-(4-methylsulfonylphenyl)-5-methyl-5-(2,2,2-trifluoroethyl)-5H-furan-2-one Step 1: (5R)-4-methyl-4-(2,2,2-trifluoroethyl)-5-(4-methylsulfonylphenyl)-3,6-dioxabicyclo[3,1,0]hexan-2-one To a 0° C. solution of the chloroacetate (1.16 g, 3 mmol) from step 3, Example 130, in acetonitrile (15 mL) was added DBU (0.491 mL, 3.3 mmol) and the mixture was warmed up to 25° C. After 2 hours, the mixture was poured on icy 1N HCl and ethyl acetate; the organic layer was separated and the aquous further extracted once with ethyl acetate. The combined organic layers were washed with brine, dried with MgSO$_4$ and the solvents were removed in vacuo to yield the essentially pure title compound (0.930 g).

$^1$H NMR (CD$_3$COCD$_3$) δ 1.60–1.70 (3H,2s), 2.50–3.05 (2H,m), 3.13 (3H,s), 4.40–4.30 (1H,2s), 7.95–8.05 (4H, 2d).

Step 2: (5R)-3-(5-bromo-2-pyridyloxy)-4-(4-methylsulfonylphenyl)-5-methyl-5-(2,2,2-trifluoroethyl)-5H-furan-2-one To a 0° C. mixture of the epoxide (0.930 g) from step 1 in dimethylformamide (3 mL) and isopropanol (12 mL) was added the potassium salt of 5-bromo-2-hydroxypyridine, prepared from 5-bromo-2-hydroxypyridine and one equivalent of 8N KOH followed by evaporation to dryness with toluene and high vacuum drying, (0.742 g, 3.5 mmol) and the mixture was warmed up slowly to reflux for 16 hrs. It was then cooled to room temperature and poured on icy dilute ammonium chloride and ethyl acetate; the organic layer was separated and the aquous further extracted ounce with ethyl acetate. The combined organic layers were washed with brine, dried with MgSO$_4$ and the solvents were removed in vacuo to yield after purification on silica gel (10% acetone/toluene) the title compound (0.380 g).

$^1$H NMR (CD$_3$COCD$_3$) δ 1.90 (3H,s), 3.15 (3H,s), 3.15–3.30 (2H,AB), 7.15 (1H,d), 7.95–8.10 (5H,m), 8.25 (1H,d).

EXAMPLE 202

(5R)-3-(5-bromo-2-pyridyloxy)-4-(4-methylsulfonylphenyl)-5-ethyl-5-methyl-5H-furan-2-one Step 1:

To a 25° C. mixture of (2R)-chloroacetic acid 2-methyl-1-(4-(methylsulfonyl)phenyl)butan-1-one ester (0.896 g, 2.7 mmol prepared as in Example 162) and 5-bromo-2-hydroxypyridine (0.560 g, 3.2 mmol) in acetonitrile (20 mL) was added DBU (1.5 mL) and the mixture was warmed up to 70–80° C. for 2 hrs. The volatils were then removed in vacuo and the mixture purified on silica gel (10% acetone/toluene) to yield the title compound (0.587 g)

$^1$H NMR (CD$_3$COCD$_3$) δ 0.90–1.0 (3H,t), 1.75 (3H,s), 2.00–2.15 (2H,m), 3.15 (3H,s), 7.10–7.15 (1H,d), 7.85–8.05 (4H,2d), 8.20–8.30 (1H,d).

EXAMPLE 203

3-(5-Chloro-6-methyl-2-pyridyloxy)-5,5-dimethyl-4-(4-methylsulfonyl)phenyl-5H-furan-2-one Step 1: 3-(5-Nitro-6-methyl-2-pyridyloxy)-5,5-dimethyl-4-(4-methylsulfonyl)phenyl-5H-furan-2-one A suspension made of the alcohol (2.82 g, 10 mmol) from step 1 Example 109, 3-nitro-6-chloro-2-picoline [C.A.70:114970s](2.06 g, 12 mmol) and 10N NaOH (1.1 mL) in DMF (35 mL) was warmed up to to 105° C. for 8 hrs. It was then cooled to room temperature and poured on icy H$_2$O and ethyl acetate. The pH was adjusted to c.a. 8 then the organic layer was separated and the aqueous further extracted ounce with ethyl acetate. The combined organic layers were washed with brine, dried with MgSO$_4$ and the solvents were removed in vacuo to yield after purification on silica gel (10% acetone/toluene) the title compound (4.180 g).

$^1$H NMR (CD$_3$COCD$_3$) δ 1.75 (6H,s), 2.70 (3H,s), 3.15 (3H,s), 7.15–7.20 (1H,d), 7.85–8.05 (4H,2d), 8.45–8.55 (1H,d).

Step 2: 3-(5-Amino-6-methyl-2-pyridyloxy)-5,5-dimethyl-4-(4-methylsulfonyl)phenyl-5H-furan-2-one A mixture of the compound from the previous step (3.19 g, 7.6 mmol), ammonium chloride (0.250 g) and iron powder (3 g) in ethanol (50 mL) and H$_2$O (20 mL) was warmed up to reflux for 1.5 hrs after what it was filtered quickly, while hot, over celite. To the filtrate was added water (250 mL) and ethyl acetate. The organic layer was separated and the aquous further extracted ounce with ethyl acetate. The combined organic layers were washed with brine, dried with MgSO$_4$ and the solvents were removed in vacuo to yield after purification by swish in diethyl ether the title compound (3.0 g).
$^1$H NMR (CD$_3$COCD$_3$) δ 1.75 (6H,s), 2.10 (3H,s), 3.25 (3H,s), 4.75–4.85 (2H,bs), 6.65–6.70 (1H,d), 7.00–7.05 (1H,d), 7.80–8.00 (4H,2d).

Step 3: 3-(5-chloro-6-methyl-2-pyridyloxy)-5,5-dimethyl-4-(4-methylsulfonyl)phenyl-5H-furan-2-one Sodium nitrite (0.152 g, 2.2 mmol) in H$_2$O (1 mL) was added dropwise to a 0° C. suspension of the compound (0.776 g) from the previous step in 6N HCl (4 mL) and the mixture was stirred at 0° C. for 0.5 hr. It was then transfered dropwise into a Cucl (0.396 g, 4 mmol) solution in 12N HCl (3 mL). The reaction mixture was warmed up to 80° C. for c.a. 10 min. then cooled to 25° C. The mixture was poured on icy H$_2$O and the pH adjusted to c.a. 4–5 then ethyl acetate was added. The organic layer was separated and the aquous further extracted ounce with ethyl acetate. The combined organic layers were washed with brine, dried with MgSO$_4$ and the solvents were removed in vacuo to yield after purification by swish in diethyl ether the title compound (0.310 g).
$^1$H NMR (CD$_3$COCD$_3$) δ 1.75 (6H,s), 2.40 (3H,s), 3.15 (3H,s), 6.90–7.00 (1H,d), 7.75–7.85 (1H,d), 7.85–8.05 (4H,2d).

EXAMPLE 207

3-(1-Cyclopropylethoxy)-4-(4-methylsulfonyl)phenyl)-5H-furan-2-one

Step 1: 3-Diazo-2,4-(3H, 5H)-furandione

To tetronic acid (5.00 g, 49.9 mmol) in CH2Cl2 (250 mL) at 0° C. were added Et3N (8.3 mL, 59.6 mmol) and tosyl azide (7.37 g, 37.4 mmol). After a period of 2 h at r.t., the reaction mixture was partitioned between NH4OAc (25%) and CH2Cl2. The organic phase was dried over Na2SO4, filtered and evaporated under reduced pressure. The resulting mixture was purified by flash chromatography (20% to 35% EtOAc in Hexane) to provide 1.4 g of the title compound as a white solid.

Step 2: 3-(1-cyclopropylethoxy)-4-hydroxy-2(5H)-furanone

To the mixture of 3-diazo-2,4-(3H, 5H)-furandione (300 mg, 2.38 mmol; Example 207, Step 1) and α-methylcyclopropanemethanol (2.0 mL) was added rhodium acetate (30 mg). The mixture was heated at 130° C. for a period of 18 h. The excess of alcohol was evaporated under reduced pressure and the resulting crude mixture was purified by flash chromatography (10% to 20% MeOH in CH2Cl2) to provide 50 mg of the title compound.

Step 3: 3-(1-cyclopropylethoxy)-4-(4-methylthio)phenyl)-5H-furan-2-one

To a mixture of 3-(1-cyclopropylethoxy)-4-hydroxy-2-(5H) furanone (50 mg, 0.27 mmol; Example 207, Step 2) and diisopropylethylamine (0.066 mL, 0.38 mmol) in CH2Cl2 (2.0 mL) at −20° C. was added trifluoromethanesulfonic anhydride (0.060 mL, 0.36 mmol). After a period of 5 min. at −20° C., the reaction mixture was brought to 0° C. then to r.t. The reaction mixture was partitioned between NH4OAc (25%) and CH2Cl2. The organic phase was dried over Na2SO4, filtered and evaporated under reduced pressure. The title compound was purified by flash chromatography to provide 30 mg of material.

Step 4: 3-(1-cyclopropylethoxy)-4-(4-methylsulfonyl)phenyl)-5H-furan-2-one

To a mixture of 3-(1-cyclopropylethoxy)-4-(4-methylthio)phenyl)-5H-furan-2-one (30 mg, 0.10 mmol; Example 207, Step 3) in CH2Cl2((1.0 mL) MeOH (3.0 mL) were added an excess of OXONE® (150 mg). After the TLC showed completion, the reaction mixture was extracted with EtOAc. The organic phase was dried over Na2SO4 filtered and evaporated under reduced pressure. The title compound was purified by flash chromatography to provide 6 mg of material.
$^1$H NMR (CD3COCD3) δ 0.20–0.60 (4H,m), 1.10 (1H,m), 1.45 (3H,d), 3.20 (3H,s), 4.50 (1H,m), 5.30 (2H,s), 8.10 (4H,m).

EXAMPLE 208

3-(1-Cyclopropylmethoxy)-4-(4-methylsulfonyl)phenyl)-5H-furan-2-one

The title compound was prepared as described in Example 207.
$^1$H NMR (CD3COCD3) δ 0.40–0.65 (4H,m), 1.30 (1H,m), 3.20 (3H,s), 4.30 (2H,d), 5.30 (2H,s), 8.05 (4H,m).

PREPARATION OF THE PRECURSOR FOR EXAMPLE 40

3-(4-(Methylsulfonyl)phenyl)-2-(3-pyridinyl)-2-cyclopenten-1-one

Step 1: 2-Bromo-2-cyclopenten-1-one

To a 0°0 C. solution of 2-cyclopenten-1-one (125 g, 1.52 mol) in CCl$_4$ (1.2 L) in a three-neck flask equipped with an overhead stirrer was added a solution of bromine (269 g, 1.68 mol) in CCl$_4$ (400 mL) dropwise over 4 h, maintaining an internal temperature <2° C. A solution of Et$_3$N (310 mL, 2.22 mol) in CCl$_4$ (200 mL) was then added dropwise over 1.5 h, maintaining an internal temperature <10° C. The resulting suspension was warmed to r.t. for 1 h, then cooled to 0° C. and filtered. The filtrate was washed with two 700 mL portions of 3M HCl and 500 mL of brine, then filtered through cotton. Concentration provided 228 g of an orange oil which was crystalized from 150 mL of 2:1 hexane:ether to provide 191 g of the title compound.
$^1$H NMR (CD$_3$COCD$_3$) δ 7.94 (1H,t), 2.72 (2H,m), 2.46 (2H,m).

Step 2: 2-Bromo-3-(4-(methylthio)phenyl)-2-cyclopenten-1-one

To a −78° C. solution of 4-bromothioanisole (35.1 g, 173 mmol) in THF (500 mL) was added nBuLi (1.6 M in hexanes, 107.5 mL, 172 mmol). The solution was stirred for 45 min, then a solution of 2-bromo-2-cyclopenten-1-one (25.4 g, 158 mmol) in THF (150 mL was added and the mixture was allowed to warm to 0° C. and was quenched with saturated aqueous NH$_4$Cl. The majority of the solvent was removed in vacuo and the residue was suspended in water and extracted with two portions of EtOAc. The organic layers were washed with brine, dried over MgSO$_4$, filtered and concentrated. This material was dissolved in DMF (300 mL), cooled to 0° C. and treated with PDC (72.4 g, 192 mmol). The resulting mixture was warmed to r.t. and stirred for 2 h, then poured into H$_2$O (1.2 L) and extracted with two 500 mL portions of EtOAc. The organic layers were washed with brine, dried over MgSO$_4$, filtered and concentrated to give the title compound as a light brown solid which was used directly in the next step.

Step 3: 2-Bromo-3-(4-(methylsulfonyl)phenyl)-2-cyclopenten-1-one

To a 0° C. solution of 2-bromo-3-(4-(thiomethyl)phenyl)-2-cyclopenten-1-one in 2:1 CH$_2$Cl$_2$/MeOH (500 mL) was added MMPP (100 g). The mixture was stirred at r.t. overnight, then concentrated and partitioned between saturated NaHCO$_3$, 1M Na$_2$S$_2$O$_3$ and CH$_2$Cl$_2$. The aqueous layer was extracted with CH$_2$Cl$_2$, and the combined organics were washed with brine, filtered through cotton and evaporated. The resulting solid was swished in $CH_2Cl_2/Et_2O$ to provide 23 g of the title compound.

$^1H$ NMR $(CD_3COCD_3)$ δ 8.12 (4H,m), 3.22 (2H,m), 3.20 (3H,s), 2.69 (2H,m).

Step 4: Lithium 3-pyridinyltrimethyl boronate

To a −88° C. solution of 3-bromopyridine (10.1 mL, 104.8 mmol) in $Et_2O$ (450 mL) was added a 1.6 M hexane solution of n-BuLi (66 mL, 105.6 mmol). The reaction mixture was warmed to −78° C. for 1 h to give a thick yellow slurry. Triisopropyl borate (26 mL, 112.7 mmol) was then added to give a slight exotherm (−78° C. to −63° C.) and a clear solution. The mixture was stirred at −78° C. for 15 min, then warmed to r.t. and concentrated to dryness. The residue was dissolved in MeOH and concentrated three times to give 27.2 g of pyridin-3-yl-trimethyl lithium boronate. This material was used in the next step without further purification.

$^1H$ NMR $(CD_3OD, 400$ MHz$)$ δ 7.15 (1H,m), 7.85 (1H,m), 8.15 (1H, m), 8.50 (1H,m)

Step 5: 3-(4-Methylsulfonyl)phenyl)-2-(3-pyridinyl)-2-cyclopenten-1-one

To a mixture of 2-bromo-3-(4-(methylsulfonyl)phenyl)-2-cyclopenten-1-one (3.37 g, 10.7 mmol), lithium 3-pyridinyltrimethyl boronate (3.43 g, 18.2 mmol), $Pd_2(dba)_3$ (0.196 g, 0.214 mmol), and $PPh_3$ (0.224 g, 0.855 mmol) was added toluene (75 mL), n-propanol (25 mL), and $H_2O$ (25 mL). The mixture was degassed and stirred under $N_2$ for 15 min then heated to reflux. After 4 h, the reaction mixture was cooled to r.t., diluted with 100 mL of $CH_2Cl_2$ and washed with $H_2O$. The aqueous layer was separated and washed 3 times with 100 mL of $CH_2Cl_2$. The organic layers were combined, washed with brine and filtered through cotton. The filtrate was concentrated to dryness and the residue was purified by flash chromatography (100% EtOAc) followed by swishing in a mixture of $CH_2Cl_2$ and $Et_2O$ to provide 2.6 g of the title compound.

$^1H$ NMR $(CDCl_3)$ δ 8.55 (1H,m), 8.34 (1H,m), 7.40 (2H,m), 7.65 (1H,m), 7.49 (2H,m), 7.33 (1H,m), 3.12 (2H,m), 3.05 (3H,s), 2.80 (2H,m).

What is claimed is:

1. A compound of Formula I

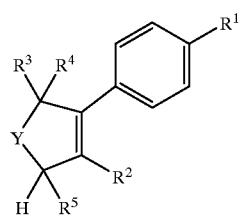

I or a pharmaceutically acceptable salt thereof wherein:

Y is $C(R^6)(R^7)$;

$R^1$ is selected from the group consisting of:
(a) $S(O)_2CH_3$ and
(b) $S(O)_2NH^8$;

$R^2$ is selected from the group consisting of:
(a) $NR^{10}R^{11}$,
(b) $SR^{11}$,
(c) $OR^{11}$,
(d) $R^{11}$,
(e) C1–10alkenyl,
(f) C1–10alkynyl,
(g) unsubstituted, mono-, di-, tri- or tetra-substituted $C_3$–$C_{10}$cycloalkenyl wherein the substituents are independently selected from the group consisting of:
(1) halo,
(2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl-$CO_2$—$R^{12}$,
(13) benzyloxy,
(14) —O—($C_{1-10}$alkyl)—$CO_2R^{12}$, and
(15) —O—($C_{1-10}$alkyl)—$NR^{12}R^{13}$, (h) a mono-, di-, tri- or tetra-substituted heterocycloalkyl group of 5, 6 or 7 members or a benzoheterocycle wherein said heterocycloalkyl or benzoheterocycle contains 1 or 2 heteroatoms selected from O, S, or N and optionally contains a carbonyl group or a sulfonyl group, and wherein said substituents are independently selected from the group consisting of:
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —$C(R^{12})(R^{13})$—OH, and
(9) —$C(R_{12})(R^{13})$—O—$C_{1-10}$alkyl, (i) styryl or mono or di-substituted styryl wherein the substituent are independently selected from the group consisting of:
(1) halo,
(2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl-$CO_2$—$R^{12}$,
(13) benzyloxy,
(14) —O—($C_{1-10}$alkyl)—$CO_2R^{12}$, and
(15) —O—($C_{1-10}$alkyl)—$NR^{12}R^{13}$, (j) phenylacetylene or mono- or di-substituted phenylacetylene wherein the substituents are independently selected from the group consisting of:
(1) halo,
(2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl-$CO_2$—$R^{12}$,
(13) benzyloxy,
(14) —O—($C_{1-10}$alkyl)—$CO_2R^{12}$,
(15) —O—($C_{1-10}$alkyl)—$NR^{12}R^{13}$, (k) $C_{1-10}$fluoroalkenyl, and
(l) mono- or di-substituted bicyclic heteroaryl of 8, 9 or 10 members, containing 2, 3, 4 or 5 heteroatoms, wherein at least one heteroatom resides on each ring of said bicyclic heteroaryl, said heteroatoms independently selected from O, S and N and said substituents are independently selected from the group consisting of:
(1) hydrogen,
(2) halo,
(3) $C_{1-10}$alkyl,
(4) $C_{1-10}$alkoxy,
(5) $C_{1-6}$alkylthio,
(6) CN,
(7) $C_{1-6}$fluoroalkyl, including $CF_3$,
(8) $N_3$,
(9) —C($R^5$)($R^6$)—OH,
(10) —C($R^5$)($R^6$)—O—$C_{1-10}$alkyl;

$R^3$ and $R^4$ are independently selected from the group consisting of hydrogen and $C_{1-10}$alkyl;

$R^5$ is $OR^{17}$;

$R^6$ and $R^7$ are independently
(a) hydrogen,
(b) unsubstituted or mono- or di-substituted phenyl or unsubstituted or mono- or di-substituted benzyl or unsubstituted or mono- or di-substituted heteroaryl or mono- or di-substituted heteroarylmethyl, wherein said substituents are independently selected from the group consisting of:
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —C($R^{14}$)($R^{15}$)—OH, and
(9) —C($R^{14}$)($R^{15}$)—O—$C_{1-10}$alkyl, and
(c) $C_{1-10}$alkyl, $CH_2OR^8$, CN, $CH_2CN$, $C_{1-10}$fluoroalkyl, $CONR^8{}_2$, F or $OR^8$, or $R^6$ and $R^7$ together with the carbon to which they are attached form a saturated monocyclic carbon ring of 3, 4, 5, 6 or 7 atoms;

each $R^8$ is independently selected from the group consisting of:
(a) hydrogen and
(b) $R^9$;

each $R^9$ is independently selected from the group consisting of:
(a) $C_{1-10}$alkyl,
(b) —$C_{1-10}$alkyl-$CO_2H$,
(c) $C_{1-10}$alkyl—$NH_2$,
(d) phenyl or mono-, di- or tri-substituted phenyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
(e) benzyl or mono-, di- or tri-substituted benzyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
(f) $C_{3-10}$cycloalkyl,
(g) $C_{1-10}$alkanoyl, and
(h) benzoyl or mono-, di-, or trisubstituted benzoyl wherein the substituents are independently selected from halo, $C_{1-10}$alkyl, $C_{1-10}$alkoxy, $C_{1-10}$alkylthio, $C_{1-10}$alkyl$CO_2H$, —$C_{1-10}$alkyl$NH_2$, CN, $CO_2H$ and $CF_3$, each $R^{10}$ is independently selected from the group consisting of:
(a) hydrogen and
(b) $R^{11}$;

$R^{11}$ is selected from the group consisting of:
(a) $C_{1-10}$alkyl,
(b) $C_{3-10}$cycloalkyl,
(c) unsubstituted, mono-, di- or tri-substituted phenyl or naphthyl wherein the substituents are independently selected from the group consisting of:
(1) halo,
(2) $C_{1-10}$alkoxy,
(3) $C_{1-10}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —C($R^{12}$)($R^{13}$)—OH,
(11) —C($R^{12}$)($R^{13}$)—O—$C_{1-4}$alkyl,
(12) —$C_{1-6}$alkyl-$CO_2$—$R^{12}$,
(13) benzyloxy,
(14) —O—($C_{1-10}$alkyl)—$CO_2R^{12}$, and
(15) —O—($C_{1-10}$alkyl)—$NR^{12}R^{13}$,
(d) unsubstituted mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of:
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —C($R^{12}$)($R^{13}$)—OH, and
(9) —C($R^{12}$)($R^{13}$)—O—$C_{1-10}$alkyl,
(e) unsubstituted, mono- or di-substituted benzoheterocycle in which the benzoheterocycle is a 5, 6, or 7-membered ring which contains 1 or 2 heteroatoms independently selected from O, S, or N and optionally a carbonyl group or a sulfonyl group, wherein said substituents are selected from the group consisting of:
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —C($R^{12}$)($R^{13}$)—OH, and
(9) —C($R^{12}$)($R^{13}$)—O—$C_{1-10}$alkyl,
(f) unsubstituted, mono- or di-substituted benzocarbocycle in which the carbocycle is a 5, 6, or 7-membered ring which optionally contains a carbonyl group, wherein said substituents are independently selected from the group consisting of:
(1) halo,
(2) $C_{1-10}$alkyl,
(3) $C_{1-10}$alkoxy, (4) $C_{1-10}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-10}$alkyl;

each $R^{12}$ or $R^{13}$ is independently selected from the group consisting of:
(a) hydrogen, and
(b) $C_{1-10}$alkyl, or $R^{12}$ and $R^{13}$ together with the atom to which they are attached form a saturated monocyclic ring of 3, 4, 5, 6 or 7 atoms;

$R^{14}$ and $R^{15}$ are independently selected from the group consisting of:
(a) hydrogen, and
(b) $C_{1-10}$alkyl, or $R^{14}$ and $R^{15}$ together with the carbon to which they are attached form a carbonyl, —C(=S)—, or a saturated monocyclic carbon ring of 3, 4, 5, 6, or 7 atoms;

each $R^{17}$ is independently selected from the group consisting of:
(a) hydrogen and
(b) $R^{18}$; and each $R^{18}$ is independently selected from the group consisting of:
(a) $C_{1-10}$alkyl,
(b) —$C_{1-10}$alkyl-$CO_2H$,
(c) $C_{1-10}$alkyl-$NH_2$,
(d) phenyl or mono-, di- or tri-substituted phenyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
(e) benzyl or mono-, di- or tri-substituted benzyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$CN, $CO_2H$ and $CF_3$,
(f) $C_{3-10}$cycloalkyl,
(g) H-(oxyethyl)n wherein n is 1 to 6,
(h) $C_{1-10}$alkanoyl, and
(i) benzoyl or mono-, di-, or trisubstituted benzoyl wherein the substituents are independently selected from halo, $C_{1-10}$alkyl, $C_{1-10}$alkoxy, $C_{1-10}$alkylthio, $C_{1-10}$alkyl$CO_2H$, —$C_{1-10}$alkyl$NH_2$, CN, $CO_2H$ and $CF_3$.

2. A compound according to claim 1 wherein $R^5$ is selected from the group conssiting of
(a) $OR^{17}$,
(b) $SR^{18}$, and
(c) $NHS(O)_2R^{18}$.

3. A compound according to claim 1 wherein:
Y is $CR^6R^7$;
$R^1$ is selected from the group consisting of
(a) $S(O)_2CH_3$,
(b) $S(O)_2NH^8$,
(c) $S(O)_2NHC(O)CF_3$; and
(d) $S(O)(NH)NH_2$;

$R^2$ is selected from the group consisting of
(a) $SR^{11}$,
(b) $OR^{11}$,
(c) $R^{11}$,
(d) unsubstituted, mono-, di-, tri- or tetra-substituted $C_{3-6}$cycloalkenyl wherein the substituents are independently selected from the group consisting of
(1) halo,
(2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-6}$alkyl,
(10) —$C(R^{12})(R^{13})$—OH,
(11) —$C(R^{12})(R^{13})$—O—$C_{1-4}$alkyl,
(12) —$C_{1-6}$alkyl-$CO_2$—$R^{12}$;
(13) benzyloxy,
(14) —O—($C_{1-10}$alkyl)—$CO_2R^{12}$, and
(15) —O—($C_{1-10}$alkyl)—$NR^{12}R^{13}$;

(e) a mono-, di-, tri- or tetra-substituted heterocycloalkyl group of 5, 6 or 7 members or a benzoheterocycle wherein said heterocycloalkyl or benzoheterocycle contains 1 or 2 heteroatoms selected from O, S, or N and optionally contains a carbonyl group or a sulfonyl group, and wherein said substituents are independently selected from the group consisting of
(1) halo,
(2) $C_{1-6}$alkyl,
(3) $C_{1-6}$alkoxy,
(4) $C_{1-6}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-6}$alkyl;

(f) phenylacetylene or mono- or di-substituted phenylacetylene wherein the substituents are independently selected from the group consisting of
(1) halo,
(2) $C_{1-6}$alkoxy,
(3) $C_{1-6}$alkylthio,
(4) CN,
(5) $CF_3$,
(6) $C_{1-6}$alkyl,
(7) $N_3$,
(8) —$CO_2H$,
(9) —$CO_2$—$C_{1-6}$alkyl,
(10) —$C(R^{12})(R^{13})$—OH,
(11) —$C(R^{12})(R^{13})$—O—$C_{1-4}$alkyl,
(12) —$C_{1-6}$alkyl—$CO_2$—$R^{12}$,
(13) benzyloxy,
(14) —O—($C_{1-6}$alkyl)—$CO_2R^{12}$,
(15) —O—($C_{1-6}$alkyl)—$NR^{12}R^{13}$, and $R^3$ is hydrogen, $C_{1-10}$alkyl, $CH_2OR^8$, CN, $CH_2CN$, or $C_{1-6}$fluoroalkyl, F, $CONR^8{}_2$;

$R^4$ is
(a) hydrogen,
(b) $C_{1-6}$alkyl,
(c) $C_{1-6}$alkoxy,
(d) $C_{1-6}$alkylthio,
(e) —OH,
(f) —$OCOR^8$,
(g) —SH, or $R^3$ and $R^4$ together with the carbon to which they are attached form a monocyclic ring of 3, 4, 5, 6, or 7 members which ring optionally contains one or two heteroatoms selected from O, S or N;

$R^5$ is selected from the group consisting of
(a) $OR^{17}$,
(b) $SR^{18}$, and
(c) $NHS(O)_2R^{18}$;

$R^6$ and $R^7$ are independently
(a) hydrogen,
(b) $C_{1-10}$alkyl, $CH_2OR^8$, CN, $CH_2CN$, $C_{1-10}$fluoroalkyl, $CONR^8_2$, F or $OR^8$,
or $R^6$ and $R^7$ together with the carbon to which they are attached form a saturated monocyclic carbon ring of 3, 4, 5, 6 or 7 atoms;
each $R^8$ is independently selected from the group consisting of
(a) hydrogen and
(b) $R^9$;
each $R^9$ is independently selected from the group consisting of
(a) $C_{1-10}$alkyl,
(b) —$C_{1-10}$alkyl-$CO_2H$
(c) $C_{1-10}$alkyl—$NH_2$
(d) phenyl or mono-, di- or tri-substituted phenyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
(e) benzyl or mono-, di- or tri-substituted benzyl wherein the substituents are independently selected from halo, $C_{1-10}$alkyl, $C_{1-10}$alkyl$NH_2$, CN, $CO_2H$ and $CF_3$,
(f) $C_{3-10}$cycloalkyl,
(g) $C_{1-10}$alkanoyl, and
(h) benzoyl or mono-, di-, or trisubstituted benzoyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
$R^{11}$ is selected from the group consisting of
(a) $C_{1-10}$alkyl,
(b) $C_{3-10}$cycloalkyl,
(c) unsubstituted, mono-, di- or tri-substituted phenyl or naphthyl wherein the substituents are independently selected from the group consisting of
(1) halo,
(2) $C_{1-6}$alkoxy,
(3) $C_{1-6}$alkylthio,
(4) CN,
(5) $CF_3$,
(6) $C_{1-6}$alkyl,
(7) $N_3$,
(8) —$CO_2H$,
(9) —$CO_2$—$C_{1-6}$alkyl,
(10) —$C(R^{12})(R^{13})$—OH,
(11) —$C(R^{12})(R^{13})$—O—$C_{1-4}$alkyl,
(12) —$C_{1-6}$alkyl-$CO_2$—$R^{12}$,
(13) benzyloxy,
(14) —O—$(C_{1-6}$alkyl)—$CO_2R^{12}$, and
(15) —O—$(C_{1-6}$alkyl)—$NR^{12}R^{13}$,
(d) unsubstituted, mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
(1) halo,
(2) $C_{1-6}$alkyl,
(3) $C_{1-6}$alkoxy,
(4) $C_{1-6}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-6}$alkyl;
(e) unsubstituted, mono- or di-substituted benzoheterocycle in which the benzoheterocycle is a 5, 6, or 7-membered ring which contains 1 or 2 heteroatoms independently selected from O, S, or N and optionally a carbonyl group or a sulfonyl group, wherein said substituents are selected from the group consisting of
(1) halo,
(2) $C_{1-6}$alkyl,
(3) $C_{1-6}$alkoxy,
(4) $C_{1-6}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-10}$alkyl;
(f) unsubstituted, mono- or di-substituted benzocarbocycle in which the carbocycle is a 5, 6, or 7-membered ring which optionally contains a carbonyl group, wherein said substituents are independently selected from the group consisting of
(1) halo,
(2) $C_{1-6}$alkyl,
(3) $C_{1-6}$alkoxy,
(4) $C_{1-6}$alkylthio,
(5) CN,
(6) $CF_3$,
(7) $N_3$,
(8) —$C(R^{12})(R^{13})$—OH, and
(9) —$C(R^{12})(R^{13})$—O—$C_{1-10}$alkyl;
each $R^{12}$ or $R^{13}$ is independently selected from the group consisting of
(a) hydrogen, and
(b) $C_{1-6}$alkyl,
each $R^{17}$ is independently selected from the group consisting of
(a) hydrogen and
(b) $R^{18}$; and
each $R^{18}$ is independently selected from the group consisting of
(a) $C_{1-6}$alkyl,
(b) —$C_{1-10}$alkyl-$CO_2H$
(c) $C_{1-6}$alkanoyl, and
(d) H-(oxyethyl)n wherein n is 1 to 6.

4. A compound according to claim 3 wherein:
Y is $CR^6R^7$;
$R^1$ is selected from the group consisting of
(a) $S(O)_2CH_3$, and
(b) $S(O)_2NH^8$;
$R^2$ is selected from the group consisting of
(a) $OR^{11}$,
(b) $R^{11}$,
(c) a mono-, di-, tri- or tetra-substituted heterocycloalkyl group of 5, 6 or 7 members or a benzoheterocycle wherein said heterocycloalkyl or benzoheterocycle contains 1 or 2 heteroatoms selected from O, S, or N and optionally contains a carbonyl group or a sulfonyl group, and wherein said substituents are independently selected form the group consisting of
(1) halo,
(2) $C_{1-4}$alkyl,
(3) $C_{1-4}$alkoxy, (4) $C_{1-4}$alkylthio,
(5) $CF_3$, and
(6) —$C(R^{12})(R^{13})$—OH;
(d) phenylacetylene or mono- or di-substituted phenylacetylene wherein the substituents are independently selected from the group consisting of
(1) halo,
(2) $C_{1-4}$alkyl,
(3) $C_{1-4}$alkoxy,
(4) $C_{1-4}$alkylthio,
(5) $CF_3$, and
(6) —$C(R^{12})(R^{13})$—OH;
$R^3$ is hydrogen, $C_{1-4}$alkyl, $CH_2OH$, or $C_{1-6}$fluoroalkyl, F, $CONH_2$;
$R^4$ is
(a) hydrogen,
(b) $C_{1-4}$alkyl,
(c) $C_{1-4}$alkoxy,
(d) $C_{1-4}$alkylthio,
(e) —OH,
or $R^3$ and $R^4$ together with the carbon to which they are attached form a monocyclic ring of 3, 4, 5, 6, or 7 members which ring optionally contains one or two heteroatoms selected from O, S or N;
$R^5$ is selected from the group consisting of
(a) $OR^{17}$, and
(b) $SR^{18}$;
$R^6$ and $R^7$ are independently
(a) hydrogen,
(b) $C_{1-4}$alkyl, $CH_2OH$, CN, $CH_2CN$, $C_{1-4}$fluoroalkyl, $CONH_2$, F or OH,
or $R^6$ and $R^7$ together with the carbon to which they are attached form a saturated monocyclic carbon ring of 3, 4, 5, 6 or 7 atoms;
each $R^8$ is independently selected from the group consisting of
(a) hydrogen and
(b) $R^9$;
each $R^9$ is independently selected from the group consisting of
(a) $C_{1-4}$alkyl,
(b) —$C_{1-4}$alkyl-$CO_2H$
(c) phenyl or mono-, di- or tri-substituted phenyl wherein the substituents are independently selected from halo, $C_{1-4}$-alkyl, $C_{1-4}$alkoxy, $C_{1-4}$alkylthio, $C_{1-4}$alkyl$CO_2H$, $C_{1-4}$alkyl$NH_2$, CN, $CO_2H$ and $CF_3$,
(f) $C_{3-6}$cycloalkyl,
(g) $C_1$-$C_4$alkanoyl, and
(h) benzoyl or mono-, di-, or trisubstituted benzoyl wherein the substituents are independently selected from halo, $C_{1-4}$alkyl, $C_{1-4}$alkoxy, $C_{1-4}$alkylthio, $C_{1-4}$alkyl$CO_2H$, —$C_{1-4}$alkyl$NH_2$, CN, $CO_2H$ and $CF_3$,
$R^{11}$ is selected from the group consisting of
(a) unsubstituted, mono- or di-substituted phenyl wherein the substituents are independently selected from the group consisting of
(1) halo,
(2) $C_{1-4}$alkoxy,
(3) $C_{1-4}$alkylthio,
(5) $CF_3$,
(6) $C_{1-4}$alkyl,
(7) —$CO_2H$,
(8) —$CO_2$—$C_{1-6}$alkyl,
(9) —$C(R^{12})(R^{13})$—OH,
(d) unsubstituted mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
(1) halo,
(2) $C_{1-4}$alkoxy,
(3) $C_{1-4}$alkylthio,
(4) $CF_3$,
(5) $C_{1-4}$alkyl,
(6) —$CO_2H$,
(7) —$CO_2$—$C_{1-6}$alkyl,
(8) —$C(R^{12})(R^{13})$—OH,
(e) unsubstituted, mono- or di-substituted benzoheterocycle in which the benzoheterocycle is a 5, 6, or 7-membered ring which contains 1 or 2 heteroatoms independently selected from O, S, or N and optionally a carbonyl group or a sulfonyl group, wherein said substituents are selected from the group consisting of
(1) halo,
(2) $C_{1-4}$alkoxy,
(3) $C_{1-4}$alkylthio,
(4) $CF_3$,
(5) $C_{1-4}$alkyl,
(6) —$CO_2H$,
(7) —$CO_2$—$C_{1-6}$alkyl,
(8) —$C(R^{12})(R^{13})$—OH,
(f) unsubstituted, mono- or di-substituted benzocarbocycle in which the carbocycle is a 5, 6, or 7-membered ring which optionally contains a carbonyl group, wherein said substituents are independently selected from the group consisting of
(1) halo,
(2) $C_{1-4}$alkoxy,
(3) $C_{1-4}$alkylthio,
(4) $CF_3$,
(5) $C_{1-4}$alkyl,
(6) —$CO_2H$,
(7) —$CO_2$—$C_{1-6}$alkyl,
(8) —$C(R^{12})(R^{13})$—OH,
each $R^{12}$ or $R^{13}$ is independently selected from the group consisting of
(a) hydrogen, and
(b) $C_{1-6}$alkyl,
each $R^{17}$ is independently selected from the group consisting of
(a) hydrogen and
(b) $R^{18}$; and
each $R^{18}$ is independently selected from the group consisting of
(a) $C_{1-4}$alkyl,
(b) —$C_{1-4}$alkyl-$CO_2H$
(c) $C_{1-6}$alkanoyl, and
(d) H-(oxyethyl)n wherein n is 1 to 4.
5. A compound according to claim 4 wherein:
Y is $CR^6R^7$;
$R^1$ is selected from the group consisting of
(a) $S(O)_2CH_3$, and
(b) $S(O)_2NH_2$;
$R^2$ is selected from the group consisting of
(a) $OR^{11}$,
(b) $R^{11}$,
(c) a mono- or di-substituted heterocycloalkyl group of 5 or 6 members or a benzoheterocycle wherein said heterocycloalkyl or benzoheterocycle contains 1 or 2 heteroatoms selected from O, S, or N and optionally contains a carbonyl group or a sulfonyl group, and wherein said substituents are independently selected form the group consisting of
- (1) halo,
- (2) $C_{1-3}$alkyl,
- (3) $C_{1-3}$alkoxy,
- (4) $C_{1-3}$alkylthio, and
- (5) $CF_3$, (d) phenylacetylene or mono- or di-substituted phenylacetylene wherein the substituents are independently selected from the group consisting of
- (1) halo,
- (2) $C_{1-3}$alkyl,
- (3) $C_{1-3}$alkoxy,
- (4) $C_{1-3}$alkylthio, and
- (5) $CF_3$, $R^3$ is hydrogen, $C_{1-4}$alkyl, $C_{1-6}$fluoroalkyl or F;

$R^4$ is
- (a) hydrogen,
- (b) $C_{1-3}$alkyl,
- (c) $C_{1-3}$alkoxy,
- (d) $C_{1-3}$alkylthio,
- (e) —OH, or $R^3$ and $R^4$ together with the carbon to which they are attached form a monocyclic ring of 3, 4, 5 or 6 members which ring optionally contains one or two heteroatoms selected from O, S or N;

$R^5$ is selected from the group consisting of
- (a) $OR^{17}$, and
- (b) $SR^{18}$;

$R^6$ and $R^7$ are independently
- (a) hydrogen,
- (b) $C_{1-3}$alkyl, $CH_2OH$, $C_{1-3}$fluoroalkyl, $CONH_2$, F or OH, or $R^6$ and $R^7$ together with the carbon to which they are attached form a saturated monocyclic carbon ring of 3, 4, 5 or 6;

each $R^8$ is independently selected from the group consisting of
- (a) hydrogen and
- (b) $R^9$;

each $R^9$ is independently selected from the group consisting of
- (a) $C_{1-4}$alkyl,
- (b) —$C_{1-4}$alkyl-$CO_2H$
- (f) $C_{3-6}$cycloalkyl,
- (g) $C_1-C_3$alkanoyl, and $R^{11}$ is selected from the group consisting of
(a) unsubstituted, mono- or di-substituted phenyl wherein the substituents are independently selected from the group consisting of
- (1) F or Cl,
- (2) $C_{1-4}$alkoxy,
- (3) $C_{1-4}$alkylthio,
- (5) $CF_3$,
- (6) $C_{1-4}$alkyl, and
- (7) —$CO_2H$, (d) unsubstituted mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
- (1) F or Cl,
- (2) $C_{1-4}$alkoxy,
- (3) $C_{1-4}$alkylthio,
- (5) $CF_3$,
- (6) $C_{1-4}$alkyl, and
- (7) —$CO_2H$, (e) unsubstituted, mono- or di-substituted benzoheterocycle in which the benzoheterocycle is a 5, or 6-membered ring which contains 1 or 2 heteroatoms independently selected from O, S, or N and optionally a carbonyl group or a sulfonyl group, wherein said substituents are selected from the group consisting of
- (1) F or Cl,
- (2) $C_{1-4}$alkoxy,
- (3) $C_{1-4}$alkylthio,
- (5) $CF_3$,
- (6) $C_{1-4}$alkyl, and
- (7) —$CO_2H$, (f) unsubstituted, mono- or di-substituted benzocarbocycle in which the carbocycle is a 5 or 6-membered ring which optionally contains a carbonyl group, wherein said substituents are independently selected from the group consisting of
- (1) F or Cl,
- (2) $C_{1-4}$alkoxy,
- (3) $C_{1-4}$alkylthio,
- (5) $CF_3$,
- (6) $C_{1-4}$alkyl, and
- (7) —$CO_2H$, each $R^{17}$ is independently selected from the group consisting of
- (a) hydrogen and
- (b) $R^{18}$; and each $R^{18}$ is independently selected from the group consisting of
- (a) $C_{1-4}$alkyl,
- (b) —$C_{1-4}$alkyl-$CO_2H$
- (c) $C_{1-6}$alkanoyl, and
- (d) H-(oxyethyl)n wherein n is 1, 2, 3 or 4.

6. A compound according to claim 5 wherein:

Y is $CR^6R^7$;

$R^1$ is selected from the group consisting of
- (a) $S(O)_2CH_3$, and
- (b) $S(O)_2NH_2$;

$R^2$ is selected from the group consisting of
- (a) $OR^{11}$,
- (b) $R^{11}$,
- (c) a mono- or di-substituted heterocycloalkyl group of 5 or 6 members wherein said heterocycloalkyl contains 1 or 2 heteroatoms which is N and optionally contains a carbonyl group, and wherein said substituents are independently selected form the group consisting of
  - (1) Cl or F,
  - (2) $C_{1-2}$alkyl, and
  - (3) $C_{1-2}$alkoxy,
- (d) phenylacetylene or mono- or di-substituted phenylacetylene wherein the substituents are independently selected from the group consisting of
  - (1) Cl or F,
  - (2) $C_{1-2}$alkyl, and
  - (3) $C_{1-2}$alkoxy, $R^3$ is hydrogen, $C_{1-3}$alkyl;

$R^4$ is hydrogen, $C_{1-3}$alkyl;

or $R^3$ and $R^4$ together with the carbon to which they are attached form a monocyclic ring of 3, 4, 5 or 6 carbon atoms;

$R^5$ is selected from the group consisting of
- (a) $OR^{17}$, and
- (b) $SR^{18}$;

$R^6$ and $R^7$ are independently
- (a) hydrogen,
- (b) $C_{1-3}$alkyl, $CH_2OH$, $C_{1-3}$fluoroalkyl, $CONH_2$, F or OH, or $R^6$ and $R^7$ together with the carbon to which they are attached form a saturated monocyclic carbon ring of 3, 4, 5 or 6;

each $R^8$ is independently selected from the group consisting of
- (a) hydrogen and
- (b) $R^9$;

each $R^9$ is independently selected from the group consisting of
- (a) $C_{1-4}$alkyl,
- (b) $-C_{1-4}$alkyl-$CO_2H$
- (f) $C_{3-6}$cycloalkyl, and
- (g) $C_{1-3}$alkanoyl, $R^{11}$ is selected from the group consisting of
- (a) unsubstituted, mono- or di-substituted phenyl wherein the substituents are independently selected from the group consisting of
  - (1) F or Cl,
  - (2) $C_{1-4}$alkoxy,
  - (3) $C_{1-4}$alkylthio,
  - (5) $CF_3$,
  - (6) $C_{1-4}$alkyl, and
  - (7) $-CO_2H$,
- (d) unsubstituted mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
  - (1) F or Cl,
  - (2) $C_{1-4}$alkoxy,
  - (3) $C_{1-4}$alkylthio,
  - (5) $CF_3$,
  - (6) $C_{1-4}$alkyl, and
  - (7) $-CO_2H$,
- (e) unsubstituted, mono- or di-substituted benzoheterocycle in which the benzoheterocycle is a 5 or 6-membered ring which contains 1 or 2 heteroatoms independently selected from O, S, or N and optionally a carbonyl group or a sulfonyl group, wherein said substituents are selected from the group consisting of
  - (1) F or Cl,
  - (2) $C_{1-4}$alkoxy,
  - (3) $C_{1-4}$alkylthio,
  - (5) $CF_3$,
  - (6) $C_{1-4}$alkyl, and
  - (7) $-CO_2H$,
- (f) unsubstituted, mono- or di-substituted benzocarbocycle in which the carbocycle is a 5 or 6-membered ring which optionally contains a carbonyl group, wherein said substituents are independently selected from the group consisting of
  - (1) F or Cl,
  - (2) $C_{1-4}$alkoxy,
  - (3) $C_{1-4}$alkylthio,
  - (5) $CF_3$,
  - (6) $C_{1-4}$alkyl, and
  - (7) $-CO_2H$, each $R^{17}$ is independently selected from the group consisting of
- (a) hydrogen and
- (b) $R^{18}$; and each $R^{18}$ is independently selected from the group consisting of
- (a) $C_{1-4}$alkyl,
- (b) $-C_{1-4}$alkyl-$CO_2H$
- (c) $C_{1-6}$alkanoyl, and
- (d) H-(oxyethyl)n wherein n is 1 to 4.

7. A compound according to claim 6 wherein:

Y is $C(R^6)(R^7)$;

$R^1$ is selected from the group consisting of
- (a) $S(O)_2CH_3$, and
- (b) $S(O)_2NH_2$;

$R^2$ is selected from the group consisting of
- (a) $OR^{11}$,
- (b) $R^{11}$,
- (c) a mono- or di-substituted heterocycloalkyl group of 5 or 6 members wherein said heterocycloalkyl contains 1 or 2 heteroatoms which is N and optionally contains a carbonyl group, and wherein said substituents are independently selected form the group consisting of
  - (1) Cl or F,
  - (2) $C_{1-2}$alkyl, and
  - (3) $C_{1-2}$alkoxy;

$R^3$ is hydrogen, methyl or ethyl;

$R^4$ is hydrogen, methyl or ethyl;

$R^5$ is $OR^{17}$;

$R^{11}$ is selected from the group consisting of
- (a) unsubstituted, mono- or di-substituted phenyl wherein the substituents are independently selected from the group consisting of
  - (1) F or Cl,
  - (2) $C_{1-4}$alkoxy,
  - (3) $C_{1-4}$alkylthio,
  - (5) $CF_3$,
  - (6) $C_{1-4}$alkyl, and
  - (7) $-CO_2H$,
- (d) unsubstituted mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
  - (1) F or Cl,
  - (2) $C_{1-4}$alkoxy,
  - (3) $C_{1-4}$alkylthio,
  - (5) $CF_3$,
  - (6) $C_{1-4}$alkyl, and
  - (7) $-CO_2H$, each $R^{17}$ is independently selected from the group consisting of
- (a) hydrogen and
- (b) $R^{18}$; and each $R^{18}$ is independently selected from the group consisting of (a) $C_{1-4}$alkyl,
(b) —$C_{1-4}$alkyl-$CO_2H$
(c) $C_{1-6}$alkanoyl, and
(d) H-(oxyethyl)n wherein n is 2, 3 or 4.

8. A compound according to claim 7 wherein:

Y is $C(R^6)(R^7)$;

$R^1$ is selected from the group consisting of
(a) $S(O)_2CH_3$, and
(b) $S(O)_2NH_2$;

$R^2$ is selected from the group consisting of
(a) $OR^{11}$,
(b) $R^{11}$,
(c) a mono- or di-substituted heterocycloalkyl group of 5 or 6 members wherein said heterocycloalkyl contains 1 or 2 heteroatoms which is N and optionally contains a carbonyl group, and wherein said substituents are independently selected form the group consisting of
(1) Cl or F,
(2) $C_{1-2}$alkyl, and
(3) $C_{1-2}$alkoxy;

$R^3$ is hydrogen, methyl or ethyl;

$R^4$ is hydrogen, methyl or ethyl;

$R^5$ is $OR^{17}$;

$R^{11}$ is selected from the group consisting of
(a) unsubstituted, mono- or di-substituted phenyl wherein the substituents are independently selected from the group consisting of
(1) F or Cl,
(2) $C_{1-4}$alkoxy,
(3) $C_{1-4}$alkylthio,
(5) $CF_3$,
(6) $C_{1-4}$alkyl, and
(7) —$CO_2H$,
(d) unsubstituted mono- or di-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of
(1) F or Cl,
(2) $C_{1-4}$alkoxy,
(3) $C_{1-4}$alkylthio,
(5) $CF_3$,
(6) $C_{1-4}$alkyl, and
(7) —$CO_2H$, each $R^{17}$ is independently selected from the group consisting of
(a) hydrogen and
(b) $R^{18}$; and each $R^{18}$ is independently selected from the group consisting of
(a) $C_{1-4}$alkyl,
(b) —$C_{1-4}$alkyl-$CO_2H$
(c) $C_{1-6}$alkanoyl, and
(d) H-(oxyethyl)n wherein n is 2, 3 or 4.

9. A compound according to claim 8 wherein:

Y is $C(R^6)(R^7)$;

$R^1$ is selected from the group consisting of
(a) $S(O)_2CH_3$, and
(b) $S(O)_2NH_2$;

$R^2$ is selected from the group consisting of
(a) $OR^{11}$,
(b) $R^{11}$, $R^3$ is hydrogen, methyl or ethyl;

$R^4$ is hydrogen, methyl or ethyl;

$R^5$ is $OR^{17}$;

$R^{11}$ is an unsubstituted, mono- or di-substituted phenyl wherein the substituents are independently selected from the group consisting of
(1) F or Cl,
(2) $C_{1-4}$alkoxy,
(3) $C_{1-4}$alkylthio,
(5) $CF_3$,
(6) $C_{1-4}$alkyl, and
(7) —$CO_2H$, each $R^{17}$ is independently selected from the group consisting of
(a) hydrogen and
(b) $R^{18}$; and each $R^{18}$ is independently selected from the group consisting of
(a) $C_{1-3}$alkyl,
(b) —$C_{1-3}$alkyl-$CO_2H$
(c) $C_{1-3}$alkanoyl, and
(d) H-(oxyethyl)n wherein n is 2 to 4.

10. A compound according to claim 8 wherein $R^2$ is a mono- or di-substituted heteroaryl wherein heteroaryl is selected from the group consisting of
(1) furanyl,
(2) diazinyl,
(3) imidazolyl,
(4) isooxazolyl,
(5) isothiazolyl,
(6) oxadiazolyl,
(7) oxazolyl,
(8) pyrazolyl,
(9) pyridyl,
(10) pyrrolyl,
(11) tetrazinyl,
(12) tetrazolyl,
(13) thiadiazolyl,
(14) thiazolyl,
(15) thenyl,
(16) triazinyl, or
(17) triazolyl, and the substituents are selected from the group consisting of
(1) hydrogen,
(2) halo,
(3) $C_{1-4}$alkyl,
(4) $C_{1-4}$alkoxy,
(5) $C_{1-4}$alkylthio,
(6) CN, and
(7) $CF_3$.

11. A compound according to claim 10 wherein $R^2$ is a mono- or di-substituted heteroaryl wherein heteroaryl is selected from the group consisting of
(1) furanyl,
(2) diazinyl,
(3) imidazolyl,
(4) isooxazolyl,
(5) isothiazolyl,
(6) oxadiazolyl,
(7) oxazolyl,
(8) pyrazolyl,
(9) pyridyl,
(10) pyrrolyl,

(11) thiazolyl,
(12) thienyl, wherein the substituents are selected from the group consisting of
  (1) hydrogen,
  (2) halo,
  (3) $C_{1-3}$alkyl,
  (4) $C_{1-3}$alkoxy,
  (7) $CF_3$.

12. A compound according to claim 11 wherein $R^2$ is a mono- or di-substituted heteroaryl wherein heteroaryl is selected from the group consisting of
(1) furanyl,
(2) diazinyl,
(3) imidazolyl,
(4) oxadiazolyl,
(5) pyrazolyl,
(6) pyridyl,
(7) pyrrolyl,
(8) thiazolyl,
(9) thienyl, wherein the substituents are selected from the group consisting of
  (1) hydrogen,
  (2) halo,
  (3) methyl,
  (4) methoxy, and
  (5) $CF_3$.

13. A compound according to claim 12 wherein $R^2$ is a mono- or di-substituted heteroaryl wherein heteroaryl is selected from the group consisting of
(1) furanyl,
(2) diazinyl,
(3) imidazolyl,
(4) oxadiazolyl,
(5) pyrazolyl,
(6) pyridyl,
(7) thiazolyl,
(8) thienyl, wherein the substituents are selected from the group consisting of
  (1) hydrogen,
  (2) Cl or F,
  (3) methyl,
  (4) methoxy,
  (5) $CF_3$.

14. A pharmaceutical composition for treating an inflammatory disease susceptible to treatment with a non-steroidal anti-inflammatory agent comprising:
a non-toxic therapeutically effective amount of a compound according to claim 1, and a pharmaceutically acceptable carrier.

15. A method of treating an inflammatory disease susceptable to treatment with an non-steroidal anti-inflammatory agent comprising:
administration to a patient in need of such treatment of a non-toxic therapeutically effective amount of a compound according to claim 1 and a pharmaceutically acceptable carrier.

16. A method of treating cyclooxygenase mediated diseases advantageously treated by an active agent that selectively inhibits COX-2 in preference to COX-1 comprising:
administration to a patient in need of such treatment of a non-toxic therapeutically effective amount of a compound according to claim 1.

17. An anti-inflammatory pharmaceutical formulation comprising an acceptable, anti-inflammatory amount of a compound of formula (I), as defined in claim 1, or a pharmaceutically acceptable salt thereof, in association with a pharmaceutically acceptable carrier.

18. A compound of Formula I

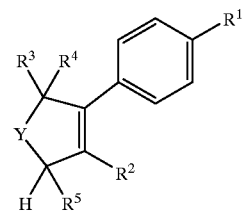

or a pharmaceutically acceptable salt thereof wherein:
Y is $C(R^6)(R^7)$;
$R^1$ is selected from the group consisting of:
  (a) $S(O)_2CH_3$ and
  (b) $S(O)_2NH^8$;
$R^2$ is selected from the group consisting of:
  (a) $NR^{10}R^{11}$,
  (b) $SR^{11}$,
  (c) $OR^{11}$,
  (d) $R^{11}$,
  (e) C1–10alkenyl,
  (f) C1–10alkynyl,
  (g) unsubstituted, mono-, di-, tri- or tetra-substituted $C_3$–$C_{10}$cycloalkenyl wherein the substituents are independently selected from the group consisting of:
    (1) halo,
    (2) $C_{1-6}$alkoxy,
    (3) $C_{1-6}$alkylthio,
    (4) CN,
    (5) $CF_3$,
    (6) $C_{1-10}$alkyl,
    (7) $N_3$,
    (8) —$CO_2H$,
    (9) —$CO_2$—$C_{1-10}$alkyl,
    (10) —$C(R^{12})(R^{13})$—OH,
    (11) —$C(R^{12})(R^{13})$—O—$C_{1-4}$alkyl,
    (12) —$C_{1-10}$alkyl-$CO_2$—$R^{12}$,
    (13) benzyloxy,
    (14) —O—($C_{1-10}$alkyl)—$CO_2R^{12}$, and
    (15) —O—($C_{1-10}$alkyl)—$NR^{12}R^{13}$,
  (h) a mono-, di-, tri- or tetra-substituted heterocycloalkyl group of 5, 6 or 7 members or a benzoheterocycle wherein said heterocycloalkyl or benzoheterocycle contains 1 or 2 heteroatoms selected from O, S, or N and optionally contains a carbonyl group or a sulfonyl group, and wherein said substituents are independently selected from the group consisting of:
    (1) halo,
    (2) $C_{1-10}$alkyl,
    (3) $C_{1-10}$alkoxy,
    (4) $C_{1-10}$alkylthio,
    (5) CN,
    (6) $CF_3$,
    (7) $N_3$,
    (8) —$C(R^{12})(R^{13})$—OH, and
    (9) —$C(R_{12})(R^{13})$—O—$C_{1-10}$alkyl,
  (i) styryl or mono or di-substituted styryl wherein the substituent are independently selected from the group consisting of:
    (1) halo,
    (2) $C_{1-6}$alkoxy,
    (3) $C_{1-6}$alkylthio,
    (4) CN,
    (5) $CF_3$, (6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl-$CO_2$—$R^{12}$,
(13) benzyloxy,
(14) —O—($C_{1-10}$alkyl)—$CO_2R^{12}$, and
(15) —O—($C_{1-10}$alkyl)—$NR^{12}R^{13}$, (j) phenylacetylene or mono- or di-substituted phenylacetylene wherein the substituents are independently selected from the group consisting of:
(1) halo,
(2) $C_{1-6}$alkoxy,
(3) $C_{1-6}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-10}$alkyl-$CO_2$—$R^{12}$,
(13) benzyloxy,
(14) —O—($C_{1-10}$alkyl)—$CO_2R^{12}$,
(15) —O—($C_{1-10}$alkyl)—$NR^{12}R^{13}$, (k) $C_{1-10}$fluoroalkenyl, and (l) mono- or di-substituted bicyclic heteroaryl of 8, 9 or 10 members, containing 2, 3, 4 or 5 heteroatoms, wherein at least one heteroatom resides on each ring of said bicyclic heteroaryl, said heteroatoms independently selected from O, S and N and said substituents are independently selected from the group consisting of:
(1) hydrogen,
(2) halo,
(3) $C_{1-10}$alkyl,
(4) $C_{1-10}$alkoxy,
(5) $C_{1-6}$alkylthio,
(6) CN,
(7) $C_{1-6}$fluoroalkyl, including $CF_3$,
(8) $N_3$,
(9) —$C(R^5)(R^6)$—OH,
(10) —$C(R^5)(R^6)$—O—$C_{1-10}$alkyl;

$R^3$ and $R^4$ are independently selected from the group consisting of hydrogen and $C_{1-10}$alkyl;

$R^5$ is $OR^{17}$;

$R^6$ and $R^7$ are independently
(a) hydrogen,
(b) unsubstituted or mono- or di-substituted phenyl or unsubstituted or mono- or di-substituted benzyl or unsubstituted or mono- or di-substituted heteroaryl or mono- or di-substituted heteroarylmethyl, wherein said substituents are independently selected from the group consisting of:
(1) halo,
(2) $C_{1-10}$alkyl,
(3) $C_{1-10}$alkoxy,
(4) $C_{1-10}$alkylthio,
(5) CN,
(6) $CF_3$,
(7) $N_3$,
(8) —$C(R^{14})(R^{15})$—OH, and
(9) —$C(R^{14})(R^{15})$—O—$C_{1-10}$alkyl, and
(c) $C_{1-10}$alkyl, $CH_2OR^8$, CN, $CH_2CN$, $C_{1-10}$fluoroalkyl, $CONR^8_2$, F or $OR^8$, or $R^6$ and $R^7$ together with the carbon to which they are attached form a saturated monocyclic carbon ring of 3, 4, 5, 6 or 7 atoms;

each $R^8$ is independently selected from the group consisting of:
(a) hydrogen and
(b) $R^9$;

each $R^9$ is independently selected from the group consisting of:
(a) $C_{1-10}$alkyl,
(b) —$C_{1-10}$alkyl-$CO_2H$,
(c) $C_{1-10}$alkyl-$NH_2$,
(d) phenyl or mono-, di- or tri-substituted phenyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
(e) benzyl or mono-, di- or tri-substituted benzyl wherein the substituents are independently selected from halo, $C_{1-10}$alkyl, $C_{1-10}$alkoxy, $C_{1-10}$alkylthio, $C_{1-10}$alkyl$CO_2H$, $C_{1-10}$alkyl$NH_2$, CN, $CO_2H$ and $CF_3$,
(f) $C_{3-10}$cycloalkyl,
(g) $C_1$–$C_{10}$alkanoyl, and
(h) benzoyl or mono-, di-, or trisubstituted benzoyl wherein the substituents are independently selected from halo, $C_{1-10}$alkyl, $C_{1-10}$alkoxy, $C_{1-10}$alkylthio, $C_{1-10}$alkyl$CO_2H$, —$C_{1-10}$alkyl$NH_2$, CN, $CO_2H$ and $CF_3$;

each $R^{10}$ is independently selected from the group consisting of:
(a) hydrogen and
(b) $R^{11}$;

$R^{11}$ is selected from the group consisting of:
(a) $C_{1-10}$alkyl,
(b) $C_{3-10}$cycloalkyl,
(c) unsubstituted, mono-, di- or tri-substituted phenyl or naphthyl wherein the substituents are independently selected from the group consisting of:
(1) halo,
(2) $C_{1-10}$alkoxy,
(3) $C_{1-10}$alkylthio,
(4) CN,
(5) $CF_3$,
(6) $C_{1-10}$alkyl,
(7) $N_3$,
(8) —$CO_2H$,
(9) —$CO_2$—$C_{1-10}$alkyl,
(10) —$C(R^{12})(R^{13})$—OH,
(11) —$C(R^{12})(R^{13})$—O—$C_{1-4}$alkyl,
(12) —$C_{1-6}$alkyl-$CO_2$—$R^{12}$,
(13) benzyloxy,
(14) —O—($C_{1-10}$alkyl)—$CO_2R^{12}$, and
(15) —O—($C_{1-10}$alkyl)—$NR^{12}R^{13}$,
(d) unsubstituted mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or said heteroaryl is a monocyclic ring of 6 atoms, said ring having one hetero atom which is N, and optionally 1, 2, or 3 additional N atoms, and wherein said substituents are independently selected from the group consisting of:
(1) halo,
(2) $C_{1-10}$alkyl,
(3) $C_{1-10}$alkoxy,
(4) $C_{1-10}$alkylthio, (5) CN,
(6) CF$_3$,
(7) N$_3$,
(8) —C(R$^{12}$)(R$^{13}$)—OH, and
(9) —C(R$^{12}$)(R$^{13}$)—O—C$_{1-10}$alkyl, (e) unsubstituted, mono- or di-substituted benzoheterocycle in which the benzoheterocycle is a 5, 6, or 7-membered ring which contains 1 or 2 heteroatoms independently selected from O, S, or N and optionally a carbonyl group or a sulfonyl group, wherein said substituents are selected from the group consisting of:
(1) halo,
(2) C$_{1-10}$alkyl,
(3) C$_{1-10}$alkoxy,
(4) C$_{1-10}$alkylthio,
(5) CN,
(6) CF$_3$,
(7) N$_3$,
(8) —C(R$^{12}$)(R$^{13}$)—OH, and
(9) —C(R$^{12}$)(R$^{13}$)—O—C$_{1-10}$alkyl, (f) unsubstituted, mono- or di-substituted benzocarbocycle in which the carbocycle is a 5, 6, or 7-membered ring which optionally contains a carbonyl group, wherein said substituents are independently selected from the group consisting of:
(1) halo,
(2) C$_{1-10}$alkyl,
(3) C$_{1-10}$alkoxy,
(4 C$_{1-10}$alkylthio,
(5) CN,
(6) CF$_3$,
(7) N$_3$,
(8) —C(R$^{12}$)(R$^{13}$)—OH, and
(9) —C(R$^{12}$)(R$^{13}$)—O—C$_{1-10}$alkyl;

each R$^{12}$ or R$^{13}$ is independently selected from the group consisting of:
(a) hydrogen, and
(b) C$_{1-10}$alkyl,
or R$^{12}$ and R$^{13}$ together with the atom to which they are attached form a saturated monocyclic ring of 3, 4, 5, 6 or 7 atoms;

R$^{14}$ and R$^{15}$ are independently selected from the group consisting of:

(a) hydrogen, and
(b) C$_{1-10}$alkyl, or

R$^{14}$ and R$^{15}$ together with the carbon to which they are attached form a carbonyl, —C(=S)—, or a saturated monocyclic carbon ring of 3, 4, 5, 6, or 7 atoms;

each R$^{17}$ is independently selected from the group consisting of:
(a) hydrogen and
(b) R$^{18}$; and each R$^{18}$ is independently selected from the group consisting of:
(a) C$_{1-10}$alkyl,
(b) —C$_{1-10}$alkyl-CO$_2$H,
(c) C$_{1-10}$alkyl-NH$_2$,
(d) phenyl or mono-, di- or tri-substituted phenyl wherein the substituents are independently selected from halo, C$_{1-10}$alkyl, C$_{1-10}$alkoxy, C$_{1-10}$alkylthio, C$_{1-10}$alkylCO$_2$H, C$_{1-10}$alkylNH$_2$, CN, CO$_2$H and CF$_3$,
(e) benzyl or mono-, di- or tri-substituted benzyl wherein the substituents are independently selected from halo, C$_{1-10}$alkyl, C$_{1-10}$alkoxy, C$_{1-10}$alkylthio, C$_{1-10}$alkylCO$_2$H, C$_{1-10}$alkylNH$_2$CN, CO$_2$H and CF$_3$,
(f) C$_{3-10}$cycloalkyl,
(g) H-(oxyethyl)n wherein n is 1 to 6,
(h) C$_{1-10}$alkanoyl, and
(i) benzoyl or mono-, di-, or trisubstituted benzoyl wherein the substituents are independently selected from halo, C$_{1-10}$alkyl, C$_{1-10}$alkoxy, C$_{1-10}$alkylthio, C$_{1-10}$alkylCO$_2$H, —C$_{1-10}$alkylNH$_2$, CN, CO$_2$H and CF$_3$.

19. A compound according to claim 1, which is 2-(3,5-difluorophenyl)-3-(4-methylsulfonyl)phenyl)-2-cyclopenten-1-ol.

20. A compound in accordance with claim 1 selected from the group consisting of: 2-(4-Fluorophenyl)-3-(4-(methylsulfonyl)phenyl)-2-cyclopenten-1-ol, 3-(4-(Methylsulfonyl)phenyl)-2-phenyl-2-cyclopenten-1-ol and 2-(3,5-difluorophenyl)-3-(4-(methylsulfonyl)phenyl)-2-cyclopenten-1-ol.

* * * * *